US006342765B1

(12) United States Patent
Arnould

(10) Patent No.: US 6,342,765 B1
(45) Date of Patent: Jan. 29, 2002

(54) IMIDAZOLE DERIVATIVES AND THEIR USE AS FARNESYL PROTEIN TRANSFERASE INHIBITORS

(75) Inventor: Jean-Claude Arnould, Reims (FR)

(73) Assignees: AstraZeneca UK Limited, London (GB); Zeneca-Pharma SA, Cergy Cedex (FR)

( * ) Notice: Subject to any disclaimer, the term of this patent is extended or adjusted under 35 U.S.C. 154(b) by 0 days.

(21) Appl. No.: 09/509,210

(22) PCT Filed: Oct. 19, 1998

(86) PCT No.: PCT/GB98/03117

§ 371 Date: Mar. 24, 2000

§ 102(e) Date: Mar. 24, 2000

(87) PCT Pub. No.: WO99/20611

PCT Pub. Date: Apr. 29, 1999

(30) Foreign Application Priority Data

Oct. 22, 1997 (FR) .......................... 97 402502
Oct. 22, 1997 (FR) .......................... 97 402505

(51) Int. Cl.$^7$ ...................... A61K 31/44; C07D 213/00; C07D 233/54
(52) U.S. Cl. ........................ 314/341; 514/351; 514/355; 546/1; 548/314.7
(58) Field of Search .................. 548/314.7; 546/1; 514/341, 351, 355

(56) References Cited

U.S. PATENT DOCUMENTS

| 4,100,152 A | | 7/1978 | Fujino et al. | 260/112.5 |
|---|---|---|---|---|
| 4,221,803 A | * | 9/1980 | Nardi et al. | 548/312.7 |
| 4,324,792 A | | 4/1982 | Bradshaw et al. | 424/267 |
| 4,518,607 A | * | 5/1985 | Walker | 548/312.7 |
| 5,238,922 A | | 8/1993 | Graham et al. | 514/18 |
| 5,326,773 A | | 7/1994 | de Solms et al. | 514/330 |
| 5,340,828 A | | 8/1994 | Graham et al. | 514/357 |
| 5,352,705 A | | 10/1994 | Deana et al. | 514/630 |
| 5,478,934 A | | 12/1995 | Yuan et al. | 540/546 |
| 5,534,537 A | * | 7/1996 | Ciccarone et al. | 514/397 |

FOREIGN PATENT DOCUMENTS

| EP | 0 534 546 | | 3/1993 |
|---|---|---|---|
| EP | 0 696 593 | | 2/1996 |
| WO | WO 95/25086 | | 3/1995 |
| WO | 9525086 | * | 9/1995 |
| WO | WO 96/30015 | | 10/1996 |

(List continued on next page.)

OTHER PUBLICATIONS

Nardi D. et al, "New alpha, –ary–, bet. . .ETHERS. .", ARZNEI. FORS., 31/12,2123–6 Dec. 1981.*

(List continued on next page.)

Primary Examiner—Mukund J. Shah
Assistant Examiner—Sudhaker B. Patel
(74) Attorney, Agent, or Firm—Pillsbury Winthrop LLP

(57) ABSTRACT

The present invention relates to compounds of formula (I), wherein $Ar^1$ represents (A) and (B) or (C); $R^{12}$ and $R^{13}$ are independently hydrogen or $C_{1-4}$alkyl; $Ar^2$ is phenyl or heteroaryl; p is 0 or 1; $Ar^3$ is phenyl, pyridinyl, pyridazinyl, pyrimidyl or pyrazynyl, the ring being substituted on ring carbon atoms by $R^2$ and —$(CH_2)_nR^3$, and wherein $Ar^3$ is attached to $Ar^1C(R^{12})R^{13}CH(Ar^2)O$— by a ring carbon atom; $R^2$ is a group of formula (2), or $R^2$ represents a lactone of formula (3), the group of formula (2) or (3) having L or D configuration at the chiral alpha carbon in the corresponding free amino acid; n is 0, 1 or 2; $R^3$ is phenyl or heteroaryl; and $R^5$–$R^9$, m and n are as defined in the specification; or a pharmaceutically acceptable salt, prodrug or solvate thereof. Processes for their preparation, their use as therapeutic agents and pharmaceutical compositions containing them. A particular use in cancer therapy.

18 Claims, No Drawings

FOREIGN PATENT DOCUMENTS

| WO | 96 30015 |   | 10/1996 |
| --- | --- | --- | --- |
| WO | WO 96/37204 |   | 11/1996 |
| WO | WO 97/06138 |   | 2/1997 |
| WO | 9630015 | * | 5/1997 |
| WO | WO 97/17070 |   | 5/1997 |
| WO | 9717070 | * | 5/1997 |
| WO | 97 17070 |   | 5/1997 |
| WO | WO 98/32741 |   | 7/1998 |

OTHER PUBLICATIONS

James et al.; "Benzodiazepine Peptidomimetics: Potent inhibitors of Ras Farnesylation in Animal Cells"; Science, vol. 260, Jun., 1993, pp. 1937–1942.

Leftheris et al.: "Development of highly potent inhibitors of ras farnesyltransferase possessing cellular and in vivo activity"; Journal of Medicinal Chemistry, vol. 39, No. 1, —1996 pp. 224–236, XP002101847.

Lerner et al.; "Ras CAAX Petpidomimetric FTI–277 Selectively Blocks Oncogenic. . .Inactive Ras–Faf Complexes"; The Journal of Biological Chemistry, vol. 270, Nov. 1995, pp. 26802–26806.

Reiss et al.; "Inhition of Purified p21$^{ras}$ Farnesyl:Protein Trasnferase by Cys–AAX Tetrapetpides"; Cell, vol. 62, Jul., 1990, pp. 81–88.

Williams et al.: "2–Substitited piperazines as constrained amino acids. Application to the synthesis of potent, non carboxylic acid inhibitors of farnesyltransferase." Journal of Medicinal Chemistry., vol. 39, No. 7, —1996, pp. 345–1348, XP002101848.

* cited by examiner

IMIDAZOLE DERIVATIVES AND THEIR USE AS FARNESYL PROTEIN TRANSFERASE INHIBITORS

This application is the national phase of international application PCT/GB98/03117 filed Oct. 19, 1998 which designated the U.S.

This invention relates to compounds that inhibit farnesylation of mutant ras gene products through inhibition of the enzyme farnesyl-protein transferase (FPTase). The invention also relates to methods of manufacturing the compounds, pharmaceutical compositions and methods of treating diseases, especially cancer, which are mediated through farnesylation of ras.

Cancer is believed to involve alteration in expression or function of genes controlling cell growth and differentiation. Whilst not wishing to be bound by theoretical considerations the following text sets out the scientific background to ras in cancer. Ras genes are frequently mutated in tumours. Ras genes encode guanosine triphosphate (GTP) binding proteins which are believed to be involved in signal transduction, proliferation and malignant transformation. H-, K- and N-ras genes have been identified as mutant forms of ras (Barbacid M, Ann. Rev. Biochem. 1987, 56: 779–827). Post translational modification of ras protein is required for biological activity. Farnesylation of ras catalysed by FPTase is believed to be an essential step in ras processing. It occurs by transfer of the farnesyl group of farnesyl pyrophosphate (FPP) to a cysteine at the C-terminal tetrapeptide of ras in a structural motif called the CAAX box. After further post-translational modifications, including proteolytic cleavage at the cysteine residue of the CAAX box and methylation of the cysteine carboxyl, ras is able to attach to the cell membrane for relay of growth signals to the cell interior. In normal cells activated ras is believed to act in conjunction with growth factors to stimulate cell growth. In tumour cells it is believed that mutations in ras cause it to stimulate cell division even in the absence of growth factors (Travis J, Science 1993, 260: 1877–1878), possibly through being permanently in GTP activated form rather tan cycled back to GDP inactivated form. Inhibition of farnesylation of mutant ras gene products will stop or reduce activation.

One class of known inhibitors of farnesyl transferase is based on farnesyl pyrophosphate analogues; see for example European patent application EP 534546 from Merck. Inhibitors of farnesyl transferase based on mimicry of the CAAX box have been reported. Reiss (1990) in Cell 6, 81–8 disclosed tetrapeptides such as CVIM (Cys-Val-Ile-Met). James (1993) in Science 260. 1937–1942 disclosed benzodiazepine based peptidomimetic compounds. Lerner (1995) in J. Biol. Chem. 270, 26802 and Eisai in International Patent Application WO 95/25086 disclosed further peptidomimetic compounds based on Cys as the first residue. Bristol-Myers Squibb in European Patent Application EP 696593 disclosed farnesyl transferase inhibitors having a 4-sulfanylpyrrolidine residue in the first position.

According to one aspect of the present invention there is provided a compound of Formula (1):

Formula (1)

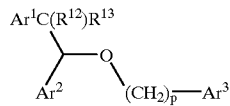

wherein $Ar^1$ represents:

(A)

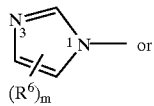

or (B)

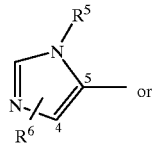

or (C)

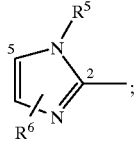

$R^5$ is hydrogen, $C_{1-4}$alkyl, phenyl$C_{1-4}$alkyl;

$R^6$ is hydrogen, $C_{1-4}$alkyl, hydroxy$C_{1-4}$alkyl, halo$C_{1-4}$alkyl, dihalo$C_{1-4}$alkyl, $C_{1-4}$alkoxy, $C_{1-4}$alkoxy$C_{1-4}$alkyl, sulfanyl$C_{1-4}$alkyl, amino$C_{1-4}$alkyl, $\underline{N}$-($C_{1-4}$alkyl)amino$C_{1-4}$alkyl, $\underline{N},\underline{N}$-di($C_{1-4}$alkyl)amino$C_{1-4}$alkyl or phenyl$C_{1-4}$alkyl; m is 0,1 or 2;

$R^{12}$ and $R^{13}$ are independently hydrogen or $C_{1-4}$ alkyl;

$Ar^2$ is phenyl or heteroaryl;

p is 0 or 1;

$Ar^3$ is phenyl, pyridinyl, pyridazinyl, pyrimidyl or pyrazinyl, the ring being substituted on ring carbon atoms by $R^2$ and $-(CH_2)_n R^3$ and wherein $Ar^3$ is attached to $Ar^1 C(R^{12})R^{13}CH(Ar^2)O-$ by a ring carbon atom;

$R^2$ is a group of the Formula (2):

Formula (2)

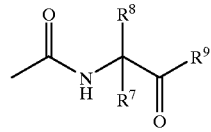

wherein $R^7$ is hydrogen or $C_{1-4}$alkyl, $R^8$ is $-(CH_2)_q-R^{10}$ wherein q is 0–4 and $R^{10}$ is $C_{1-4}$alkylsulfanyl, $C_{1-4}$alkylsulfinyl, $C_{1-4}$alkylsulfonyl, hydroxy, $C_{1-4}$alkoxy, carbamoyl, $\underline{N}$-$C_{1-4}$alkyl carbamoyl, $\underline{N},\underline{N}$-(di$C_{1-4}$alkyl)carbamoyl, $C_{1-4}$alkyl, phenyl, thienyl, or $C_{1-4}$alkanoylamino, $R^9$ is hydroxy, $C_{1-6}$alkoxy, $C_{3-9}$cycloalkyloxy, heterocyclyloxy, heterocyclyl$C_{1-4}$alkoxy or $-NH-SO_2-R^{11}$ wherein $R^{11}$ represents, trifluoromethyl, $C_{1-4}$alkyl, phenyl, heteroaryl, aryl$C_{1-4}$alkyl or heteroaryl$C_{1-4}$alkyl; or $R^2$ represents a lactone of Formula (3)

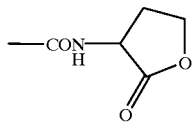

Formula (3)

the group of Formula (2) or (3) having L or D configuration at the chiral alpha carbon in the corresponding free amino acid;

n is 0, 1 or 2;

$R^3$ is phenyl or heteroaryl; phenyl and heteroaryl rings in $R^3$, $R^5$, $R^6$, $R^9$, $R^{11}$ and $Ar^2$ are independently optionally substituted on ring carbon atoms in by up to three substituents selected from $C_{1-4}$alkyl, halogen, hydroxy, $C_{1-4}$alkoxy, $C_{1-4}$alkoxycarbonyl, $C_{1-4}$alkanoyl, $C_{1-4}$alkanoyloxy, amino, $C_{1-4}$alkylamino, di($C_{1-4}$alkyl)amino, $C_{1-4}$alkanoylamino, nitro, cyano, carboxy, thiol, $C_{1-4}$alkylsulfanyl, $C_{1-4}$alkylsulfinyl, $C_{1-4}$alkylsulfonyl, $C_{1-4}$alkanesulphonamido, N-($C_{1-4}$alkylsulphonyl)-N-$C_{1-4}$alkylamino, aminosulfonyl, N-($C_{1-4}$alkyl)aminosulfonyl, N,N-di($C_{1-4}$alkyl)aminosulfonyl, carbamoyl, N-($C_{1-4}$alkyl)carbamoyl, N,N-(di$C_{1-4}$alkyl)carbamoyl, carbamoyl$C_{1-4}$alkyl, N-($C_{1-4}$alkyl)carbamoyl$C_{1-4}$alkyl, N,N-(di$C_{1-4}$alkyl)carbamoyl$C_{1-4}$alkyl, hydroxy$C_{1-4}$alkyl and $C_{1-4}$alkoxy$C_{1-4}$alkyl and on ring NH groups (replacing hydrogen) by $C_{1-4}$alkyl, $C_{1-4}$alkanoyl, $C_{1-4}$alkylsulfonyl, halo$C_{1-4}$alkyl, difluoromethyl or trifluoromethyl;

or a pharmaceutically-acceptable salt, prodrug or solvate thereof.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of Formula (1) defined above may exist in optically active or racemic forms by virtue of one or more asymmetric carbon atoms, the invention includes in its definition any such optically active or racemic form which possesses the property of inhibiting FTPase. The synthesis of optically active forms may be carried out by standard techniques of organic chemistry well known in the art, for example by synthesis from optically active starting materials or by resolution of a racemic form. Similarly, inhibitory properties against FTPase may be evaluated using the standard laboratory techniques referred to hereinafter.

The term "heterocyclyl" refers to a 5- or 6-membered monocyclic ring containing 1 to 3 heteroatoms selected from nitrogen, oxygen and sulfur. The term "heteroaryl" refers to a 5–10 membered monocyclic heteroaryl ring containing up to 3 heteroatoms selected from nitrogen, oxygen and sulphur.

The term "halogen" refers to fluorine, chlorine, bromine and iodine. The term "carbamoyl" refers to —C(O)NH$_2$. The term "BOC" refers to tert-butoxycarbonyl.

Examples of $C_{1-4}$alkyl include methyl, ethyl, propyl, isopropyl, sec-butyl and tert-butyl; examples of $C_{1-4}$alkoxy include methoxy, ethoxy and propoxy; examples of $C_{1-4}$alkanoyl include formyl, acetyl and propionyl; examples of $C_{1-4}$alkanoyloxy include acetyloxy and propionyloxy; examples of $C_{1-4}$alkylamino include methylamino, ethylaminio, propylamino, isopropylamino, sec-butylamino and tert-butylamino; examples of di-($C_{1-4}$alkyl)amino include di-methylamino, di-ethylamino and N-ethyl-N-methylamino; examples of $C_{1-4}$alkanoylamino include acetamido and propionylamino; examples of $C_{1-4}$alkoxycarbonyl include methoxycarbonyl, ethoxycarbonyl and propoxycarbonyl; examples of $C_{1-4}$alkylsulfanyl include methylsulfanyl, ethylsulfanyl, propylsulfanyl, isopropylsulfanyl, sec-butylsulfanyl and tert-butylsulfanyl; examples of $C_{1-4}$alkylsulfinyl include methylsulfinyl, ethylsulfinyl, propylsulfinyl, isopropylsulfinyl, sec-butylsulfinyl and tert-butylsulfinyl; examples of $C_{1-4}$alkylsulfonyl include methylsulfonyl, ethylsulfonyl, propylsulfonyl, isopropylsulfonyl, sec-butylsulfonyl and tert-butylsulfonyl; examples of N-($C_{1-4}$alkyl)carbamoyl include N-methylcarbamoyl and N-ethylcarbamoyl; examples of N,N-(di$C_{1-4}$alkyl)carbamoyl include N,N-dimethylcarbamoyl and N-methyl-N-ethylcarbamoyl; examples of $C_{1-4}$alkanesulfonamido include methanesulfonamido, ethanesulphonamido and propanesulfonamido; examples of $C_{1-4}$alkylsulfonyl-N-$C_{1-4}$alkylamino include methylsulfonyl-N-methylamino, ethylsulfonyl-N-methylamino and propylsulfonyl-N-methylamino; examples of fluoro$C_{1-4}$alkyl include fluoromethyl, 2-fluoroethyl and 3-fluoropropyl; examples of difluoro$C_{1-4}$alkyl include difluoromethyl, 2,2-difluoroethyl and 3,3-difluoropropyl; examples of carbamoyl$C_{1-4}$alkyl include carbamoylmethyl, carbamoylethyl and carbamoylpropyl; examples of N-($C_{1-4}$alkyl)carbamoyl$C_{1-4}$alkyl include N-methyl-carbamoylmethyl and N-ethyl-carbamoylethyl; examples of N,N-(di$C_{1-4}$alkyl)carbamoyl-$C_{1-4}$alkyl include N,N-dimethylcarbamoylethyl and N-methyl-N-ethylcarbamoylethyl; examples of hydroxy$C_{1-4}$alkyl include hydroxymethyl, hydroxyethyl, hydroxypropyl, 2-hydroxypropyl, 2-(hydroxymethyl)propyl and hydroxybutyl; examples of $C_{1-4}$alkoxy$C_{1-4}$alkyl include methoxyethyl, ethoxyethyl and methoxybutyl; examples of sulfanyl$C_{1-4}$alkyl include sulfanylmethyl, sulfanylethyl, sulfanylpropyl; and examples of N-($C_{1-4}$alkyl)amino$C_{1-4}$alkyl include N-methyl-aminomethyl and N-ethyl-aminoethyl.

Examples of 5- or 6-membered heteroaryl ring systems include imidazole, triazole, pyrazine, pyrimidine, pyridazine, pyridine, isoxazole, oxazole, isothiazole, thiazole and thiophene.

Preferably the NH group in imidazole is unsubstituted or substituted by $C_{1-4}$alkyl.

Examples of heterocyclyl rings include pyrrolidinyl, morpholinyl, piperidinyl, dihydropyridinyl and dihydropyrimidinyl.

Preferred heteroatoms are N and S, especially N. In general, attachment of heterocyclic rings to other groups is via carbon atoms.

Examples of values for $R^8$ in Formula (2) are side chains of lipophilic amino acids including such as for example methionine, phenylglycine, phenylalanine, serine, leucine, isoleucine or valine. L configuration in the corresponding free amino acid is preferred. Examples of amino acid side chains are set out below.

| Amino Acid | Side Chain |
|---|---|
| methionine | —$CH_2$—$CH_2$—S—$CH_3$ |
| phenylglycine | Ph |
| phenylalanine | —$CH_2$—Ph |
| thienylalanine | —$CH_2$-thien-2-yl |
| serine | —$CH_2$OH or a $C_{1-4}$alkyl (preferably methyl) ether thereof. |
| Leucine | —$CH_2$—$CHMe_2$ |
| homoserine | —$CH_2$—$CH_2$—OH or a $C_{1-4}$alkyl (preferably methyl) ether thereof |
| N-acetyl-lysine | —$CH_2$—$CH_2$—$CH_2$—$CH_2$—NH—$C_6$—$CH_3$ |

The lactone in Formula (3) can be formed from a group of Formula (2) when $R^9$ is OH to give a carboxyl and $R^8$ is —$CH_2$—$CH_2$—OH where $R^8$ and $R^9$ together lose a water molecule to form part of a dihydrofuran-2-one heterocyclic ring.

Preferably $R^{12}$ and $R^{13}$ are independently hydrogen or methyl.

Most preferably $R^{12}$ and $R^{13}$ are hydrogen.

Preferably $Ar^1$ is of the formula (A) or (B).

Preferably $R^6$ is hydrogen, $C_{1-4}$alkyl, hydroxy$C_{1-4}$alkyl, amino$C_{1-4}$alkyl, fluoro$C_{1-4}$alkyl, difluoro$C_{1-4}$alkyl, $C_{1-4}$alkoxy or $C_{1-4}$alkoxy$C_{1-4}$alkyl.

More preferably $R^6$ is hydrogen, methyl, fluoromethyl, difluoromethyl, methoxy or ethoxymethyl.

Most preferably $R^6$ is hydrogen or methyl.

Preferably m is 0 or 1.

Preferably $R^5$ is hydrogen or methyl.

More preferably $R^5$ is hydrogen.

In a particular aspect $Ar^1$ is 1-methylimidazol-5-yl.

Preferred heteroaryl value for $Ar^2$ are thiazolyl, pyridyl, triazolyl, pyrimidyl, pyrazinyl or pyridazinyl, especially thiazol-2-yl. When $Ar^2$ is phenyl, it is preferably unsubstituted or monosubstituted. In one aspect, when $Ar^2$ is phenyl, it is unsubstituted. In another aspect when $Ar^2$ is phenyl, it is monosubstituted in the para position.

Preferred substituents for ring carbon atoms in $Ar^2$ include $C_{1-4}$alkyl, halo, nitro, cyano and $C_{1-4}$alkoxy$C_{1-4}$alkyl.

More preferred substituents for ring carbon atoms in $Ar^2$ include methyl, ethyl, fluoro, chloro, cyano, methoxymethyl and ethoxyethyl.

When $Ar^2$ is phenyl it is preferably substituents by fluoro.

When $Ar^2$ is thiazolyl it is preferably unsubstituted.

Preferably $Ar^2$ is 4-fluorophenyl or thiazolyl.

Most preferably $Ar^2$ is 4-fluorophenyl or thiazol-2-yl.

Preferably $Ar^3$ is phenyl or pyridyl.

Most preferably $Ar^3$ is phenyl.

Preferably, when n is 0, $Ar^3$ is substituted by $R^2$ in the 4-position and —$(CH_2)_nR^3$ in the 3- or 5-position and when n is 1 or 2, $Ar^3$ is substituted by $R^2$ in the 3- or 5-position and —$(CH_2)_nR^3$ in the 4-position. The positions indicated are relative to the point of attachment of $Ar^3$ to —$(CH_2)_p$—.

Preferably n is 0 or 2.

In a particular aspect n is 0.

In one aspect p is 0.

In another aspect p is 1.

$R^2$ is preferably a group of formula:

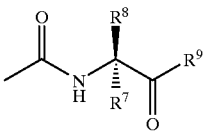

$R^7$ is preferably hydrogen or methyl, especially hydrogen. In $R^8$, q is preferably 1–4, more preferably 1 or 2, especially 2.

Within $R^8$, $R^{10}$ is preferably $C_{1-4}$alkylsulfanyl, $C_{1-4}$alkylsulfinyl, $C_{1-4}$alkylsulfonyl, hydroxy or $C_{1-4}$alkoxy. More preferably $R^{10}$ is methylsulfanyl or methylsulfonyl.

$R^9$ is preferably hydroxy, $C_{1-4}$alkoxy, $C_{3-9}$cycloalkyloxy, heterocyclyloxy or heterocyclyl$C_{1-4}$alkoxy. More preferably $R^9$ is hydroxy, methoxy, propoxy, butoxy, tert-butoxy, cyclopentyloxy, piperidin-4-yloxy or morpholino$C_{1-4}$alkyl. Most preferably, $R^9$ is methoxy, propoxy, butoxy, tert-butoxy or cyclopentyloxy.

Preferably $R^{11}$ in $R^9$ is phenyl.

Preferred substituents for NH groups in heterocyclic groups in $R^9$ include methyl, ethyl, acetyl, propionyl, fluoromethyl, difluoromethyl and trifluoromethyl.

More preferred substituents for NH groups in heterocyclic groups in $R^9$ include methyl and acetyl.

Preferred substituents for ring carbon atoms in phenyl or heteroaryl groups in $R^{11}$ include methyl, halo, $C_{1-4}$alkanoyl, nitro, cyano, $C_{1-4}$alkylsulfinyl, $C_{1-4}$alkylsulfonyl, carbamoyl, $C_{1-4}$alkylcarbamoyl and di$C_{1-4}$alkylcarbamoyl.

Preferably $R^3$ is phenyl, pyridyl or thiazolyl.

Most preferably $R^3$ is phenyl.

Preferred substituents for ring carbon atoms in $R^3$ include $C_{1-4}$alkyl, halo, $C_{1-4}$alkoxy, nitro, cyano and $C_{1-4}$alkoxy$C_{1-4}$alkyl.

More preferred substituents for ring carbon atoms in $R^3$ include methyl, fluoro, chloro, methoxy, nitro, cyano and methoxymethyl.

A preferred substituent for a ring NH group in a heteroaryl group in $R^3$ is $C_{1-4}$alkyl, particularly methyl.

When $R^3$ is phenyl it is preferably substituted in the 4-position.

Preferably n is 0 or 2.

A preferred compound of the invention is a compound of the Formula (I) wherein:

$Ar^1$ is of the formula (A) or (B);

$R^5$ is hydrogen or methyl;

$R^6$ is hydrogen, $C_{1-4}$alkyl, fluoro$C_{1-4}$alkyl, difluoro$C_{1-4}$alkyl, $C_{1-4}$alkoxy or $C_{1-4}$alkoxy$C_{1-4}$alkyl;

m is 0 or 1;

$R^{12}$ and $R^{13}$ are independently hydrogen or methyl;

$Ar^2$ is phenyl or thiazolyl;

$Ar^3$ is phenyl or pyridyl, the ring being substituted on ring carbon atoms by $R^2$ and —$(CH_2)_nR^3$ and wherein $Ar^3$ is attached to $Ar^1C(R^{12})R^{13}CH(Ar^2)O$— by a ring carbon atom; and n is 0, 1 or 2;

$R^2$ is of the formula (2) wherein $R^7$ is hydrogen or methyl;

$R^8$ is —$(CH_2)_qR^{10}$ wherein q is 0–4 and $R^{10}$ is $C_{1-4}$alkylsulfanyl, $C_{1-4}$alkylsulfinyl, $C_{1-4}$alkylsulfonyl, hydroxy or $C_{1-4}$alkoxy;

$R^9$ is hydroxy, $C_{1-4}$alkoxy, $C_{3-9}$cycloalkyloxy, heterocloxy or heterocyclyl$C_{1-4}$alkoxy;

or $R^2$ is of the formula (3);

$R^3$ is phenyl, pyridyl or thiazolyl; and phenyl, heteroaryl and heterocyclyl rings in $R^3$, $R^9$ and $Ar^2$ are independently optionally substituted on Ting carbon atoms by one or two substituents selected from $C_{1-4}$alkyl, halo, $C_{1-4}$alkoxy, $C_{1-4}$alkanoyl, nitro, cyano, $C_{1-4}$alkylsulfinyl, $C_{1-4}$alkylsulfonyl, carbamoyl, $C_{1-4}$alkylcarbamoyl and di$C_{1-4}$alkylcarbamoyl; and optionally substituted on ring NH groups by $C_{1-4}$alkyl, $C_{1-4}$alkanoyl, fluoromethyl, difluoromethyl or trifluoromethyl;

or a pharmaceutically-acceptable salt, prodrug or solvate thereof.

A more preferred compound of the invention is a compound of the formula (I) wherein:

$Ar^1$ is of the formula (A) or (B);

$R^5$ is hydrogen or methyl;

$R^6$ is hydrogen, methyl, fluoromethyl, difluoromethyl, methoxy or methoxymethyl;

m is 0 or 1;

$R^{12}$ and $R^{13}$ are independently hydrogen or methyl;

$Ar^2$ is phenyl or thiazolyl, optionally substituted on ring carbon atoms by one or two substituents selected from $C_{1-4}$alkyl, halo, nitro, cyano and $C_{1-4}$-alkoxy$C_{1-4}$alkyl;

$Ar^3$ is phenyl or pyridyl; the ring being substituted on ring carbon atoms by $R^2$ and —$(CH_2)_nR^3$ and wherein $Ar^3$ is attached to $Ar^1C(R^{12})R^{13}CH(Ar^2)O$— by a ring carbon atom; and n is 0, 1 or 2;

$R^2$ is of formula (2) wherein $R^7$ is hydrogen or methyl;

$R^8$ is —$(CH_2)_qR^{10}$ wherein q is 1 or 2, and $R^{10}$ is methylsulfanyl or methylsulfonyl;

$R^9$ is hydroxy, methoxy, propoxy, butoxy, tert-butoxy, cyclopentyloxy, piperidin-4-yloxy, or morpholino$C_{1-4}$alkyl; or $R^2$ is of the formula (3);

$R^3$ is phenyl optionally substituted by one or two substituents selected from $C_{1-4}$alkyl, halo, $C_{1-4}$alkoxy, nitro, cyano and $C_{1-4}$alkoxy$C_{1-4}$alkyl;

or a pharmaceutically-acceptable salt, prodrug or solvate thereof.

An even more preferred compound of the invention is a compound of the formula (I) wherein:

$Ar^1$ is of the formula (A) or (B);

$R^5$ is hydrogen or methyl;

$R^6$ is hydrogen or methyl;

m is 0 or 1;

$R^{11}$ and $R^{12}$ are hydrogen;

$Ar^2$ is phenyl or thiazol-2-yl wherein the phenyl ring is optionally substituted by fluoro;

$Ar^3$ is phenyl; the ring being substituted on ring carbon atoms by $R^2$ and —$(CH_2)_nR^3$ and wherein $Ar^3$ is attached to $Ar^1(R^{12})R^{13}CH(Ar^2)O$— by a ring carbon atom; and n is 0, 1 or 2;

$R^2$ is of the formula (2) wherein $R^7$ is hydrogen;

$R^8$ is —$(CH_2)_qR^{10}$ wherein q is 2 and $R^{10}$ is methylsulfanyl or methylsulfonyl;

$R^9$ is hydroxy, methoxy, propoxy, butoxy, tert-butoxy, cyclopentyloxy, piperidin-4-yloxy, or 2-morpholinoprop-2-yl;

$R^3$ is phenyl optionally substituted by fluoro;

or a pharmaceutically-acceptable salt, prodrug or solvate thereof.

Particular compounds of the present invention include:

methyl (2S)-2-{2-(4-fluorophenyl)-4-[2-(imidazol-1-yl)-1-(4-fluorophenyl)ethoxymethyl]benzoylamino}-4-methylsulfanylbutyrate;

(2S)-2-{2-(4-fluorophenyl)-4-[2-(imidazol-1-yl)-1-(4-fluorophenyl)ethoxymethyl]benzylamino]-4-methylsulfanylbutyric acid;

tert-butyl (2S)-2-{2-(4-fluorophenyl)-4-[2-(imidazol-1-yl)-1-(4-fluorophenyl)ethoxymethylbenzoylamino}-4-methylsulfanylbutyrate;

methyl (2S)-2-{2-(4-fluorophenyl)-4-[2-(imidazol-1-yl)-1-(thiazol-2-yl)ethoxymethyl]benzoylamino}-4-methylsulfanyl butyric acid;

(2S)-2-{2-(4-fluorophenyl)-4-[2-(imidazol-1-yl)-1-(thiazol-2-yl)ethoxymethyl]benzoylamino}-4-methylsulfanyl butyric acid;

methyl (2S)-2-{2-(4-fluorophenethyl)-5-[2-(imidazol-1-yl)-1-(4-fluorophenyl)-ethoxymethyl]benzoylamino}-4-methylsulfanyl butyrate;

(2S)-2-{2-(4-fluorophenethyl)-5-{2-(imidazol-1-yl)-1-(4-fluorophenyl)ethoxymethyl]benzoylamino}-4-methylsulfanylbutyric acid;

methyl (2S)-2-{2-(4-(fluorobenzyl)-5-[1-(4-fluorophenyl)-2-(imidazol-1-yl)ethoxymethyl]benzoylamino}-4-methylsulfanylbutyrate;

(2S)-2-{2-(4-fluorobenzyl)-5-[1-(4-fluorophenyl)-2-(imidazol-1-yl)ethoxymethyl]benzoylamino}-4-methylsulfanylbutyric acid;

methyl (2S)-2-{2-phenyl-4-[1-(4-fluorophenyl)-2-(imidazol-1-yl)ethoxymethyl]benzoylamino}-4-methylsulfanylbutyrate; or (2S)-2-{2-phenyl-4-[1-(4-fluorophenyl)-2-(imidazol-1-yl)ethoxymethyl]benzoylamino}-4-methylsulfanylbutyric acid;

methyl (2S)-2-{2-(4-fluorophenyl)-4-[1-(4fluorophenyl)-2-(imidazol-1-yl)ethoxymethyl]benzoylamino}-2-methyl-4-methylsulfanylbutyrate;

(2S)-2-{2-(4-fluorophenyl)-4-[1-(4-fluorophenyl)-2-(imidazol-1-yl)ethoxymethyl]benzoylamino}-2-methyl-4-metbylsulfanylbuyric acid;

N-(4-chlorobenzenesulfonyl)-(2S)-2-{2-(4-fluorophenyl)-4-[1-(4-fluorophenyl)-2-(imidazol-1-yl)ethoxymethyl]benzoylamino}-4-methylsulfanylbutyramide;

2-(morpholinomethyl)prop-2-yl (2S)-2-{2-(4-fluorophenethyl)-5-[1-(4-fluorophenyl)-2-(imidazol-1-yl)ethoxymethyl]benzoylamino)}-4-methylsulfanylbutyrate;

methyl (2S)-2-{5-[1-(4-fluorophenyl)-2-(imidazol-1-yl)ethoxy]-2-(4-fluorophenethyl)benzoylamino}-4-methylsulfanylbutyrate;

(2S)-2-{5-[1-(4-fluorophenyl)-2-(imidazol-1-yl)ethoxy]-2(4-fluorophenethyl)benzoylamino}-4-methylsulfanylbutyric acid;

tert-butyl (2S)-2-{5-[1-(4-fluorophenyl)-2-(imidazol-1-yl)ethoxy]-2-(4-fluorophenethyl)benzoylamino)}-4-methylsulfanylbutyrate;

cyclopentyl (2S)-2-{5-[1-(4-fluorophenyl)-2-(imidazol-1-yl)ethoxy]-2-(4-fluorophenethyl)benzoylamino}-4-methylsulfanylbutyrate;

tert-butyl (2S)-2-{5-[1-(4-fluorophenyl)-2-(imidazol-1-yl)ethoxy]-2-(4-fluorophenethyl)benzoylamino}-4-methylsulfonylbutyrate;

2-{5-[1-(4-fluorophenyl)-2-(imidazol-1-yl)ethoxy]-2-(4-fluorophenethyl)benzoylamino}-4-methylsulfonylbutyric acid;

methyl (2S)-2-{5-[1-(thiazol-2-yl) -2-(imidazol-1-yl)ethoxy]-2-(4-fluorophenethyl)benzoylamino}-4-methylsulfanylbutyrate;

(2S)-2-{5-[1-(thiazol-2-yl)-2-(imidazol-1-yl)ethoxy]-2-(4-fluorophenethyl)benzoylamino}-4-methylsulfanylbutyric acid;

tert-butyl (2S)-2-{5-[1-(thiazol-2-yl)-2-(imidazol-1-yl)ethoxy]-2-(4-fluorophenethyl)benzoylanino}-4-methylsulfanylbutyrate;

tert-butyl (2S)-2-{5-[1-(thiazol-2-yl)-2-(imidazol-1-yl)ethoxy]-2-(4-fluorophenethyl)benzoylamino}-4-methylsulfonylbutyrate;

(2S)-2-{5-[1-(thiazol-2-yl)-2-(imidazol-1-yl)ethoxy]-2-(4-fluorophenethyl)benzoylamino}-4-methylsulfonylbutyric acid;

methyl (2S)-2-{5-[1-(4-fluorophenyl)-2-(2-methylimidazol-1-yl)ethoxy]-2-(4-fluorophenethyl)benzoylamino}-4-methylsulfanylbutyrate;

(2S)-2-{5-[1-(4-fluorophenyl)-2-(2-methylimidazol-1-yl)ethoxy]-2-(4-fluorophenethyl)benzoylamino}-4-methylsulfanylbutyric acid;

tert-butyl (2S)-2-{4-[1-(4-fluorophenyl)-2-(imidazol-1-yl)ethoxy]-2-(4-fluorophenyl)benzoylamino}-4-methylsulfanylbutyrate;

tert-butyl (2S)-2-{4-[1-(4-fluorophenyl)-2-(imidazol-1-yl)ethoxy]-2-(4-fluorophenyl)benzoylamino}-4-methylsulfonylbutyrate;

2-{4-[1-(4-fluorophenyl)-2-(imidazol-1-yl)ethoxy]-2-(4-fluorophenyl)benzoylamino}-4-methylsulfonylbutyric acid;

methyl (2S)-2-{5-[2-(4-methylimidazol-1-yl)-1-(thiazol-2-yl)ethoxy]-2-(4-fluorophenethyl)benzoylamino}-4-methylsulfanylbutyrate;

tert-butyl (2S)-2-{5-[2-(4-methylimidazol-1-yl)-1-(thiazol-2-yl)ethoxy]-2-(4-fluorophenethyl)benzoylamino}-4-methylsulfonylbutyrate;

(2S)-2-{5-[2-(4-methylimidazol-1-yl)-1-(thiazol-2-yl)ethoxy]-2-(4-fluorophenethyl)benzoylamino}-4-methylsulfanylbutyric acid;

tert-butyl (2S)-2-{2-(4-fluorophenethyl)-5-[1-(4-fluorophenyl)-2-(1-methylimidazol-5-yl)ethoxy]benzoylamino}-4-methylsulfanylbutyrate;

tert-butyl (2S)-2-{2-(4-fluorophenethyl)-5-[1-(4-fluorophenyl)-2-(1-methylimidazol-5-yl)ethoxy]benzoylamino}-4-methylsulfonylbutyrate;

tert-butyl (2S)-2-{2-(4-fluorophenyl)-4-[1-(4-fluorophenyl)-2-(1-methylimidazol-5-yl)ethoxymethyl]benzoylamino}-4-methylsulfanylbutyrate;

tert-butyl (2S)-2-{2-(4-fluorophenyl)-4-[1-(4-fluorophenyl)-2-(1-methylimidazol-5-yl)ethoxymethyl]benzoylamino}-4-methylsulfonylbutyrate;

(2S)-2-{2-(4-fluorophenyl)-6-[1-(4-fluorophenyl)-2-(imidazol-1-yl)ethoxy]pyrid-3-oylamino}-4-methylsulfanylbutyric acid;

tert-butyl (2S)-2-{2-(4-fluorophenyl)-6-[1-(4-fluorophenyl)-2-(1-methylimidazol-5-yl)ethoxymethyl]pyrid-3-oylamino}-4-methylsulfanylbutyrate;

tert-butyl (2S)-2-{3-(4-fluorophenethyl)-6-[1-(4-fluorophenyl)-2-(1-methylimidazol-5-yl)ethoxy]pyrid-2-oylamino}-4-methylsulfanylbutyrate;

cyclopentyl (2S)-2-{3-(4-fluorophenethyl)-6-[1-(4-fluorophenyl)-2-(1-methylimidazol-5-yl)ethoxy]pyrid-2-oylamino}-4-methylsulfanylbutyrate;

(2S)-2-{2-(4-fluorophenethyl)-5-[1-(thiazol-2-yl)-2-(1-methylimidazol-5-yl)ethoxy]benzoylamino}-4-methylsulfanylbutyric acid;

(2S)-2-{2-(4-fluorophenethyl)-5-[1-(thiazol-2-yl)-2-(1-methylimidazol-5-yl)ethoxy]benzoylamino}-4-methylsulfonylbutyric acid;

tert-butyl (2S)-2-{2-(4-fluorophenethyl)-5-1-(thiazol-2-yl)-2-(1-methylimidazol-5-yl)ethoxymethyl]benzoylamino}-4-methylsulfanylbutyrate;

tert-butyl (2S)-2-{2-(4-fluorophenethyl)-5-[1-(thiazol-2-yl)-2-(1-methylimidazol-5-yl)ethoxymethyl]benzoylamino}-4-methylsulfonylbutyrate;

tert-butyl (2S)-2-{2-(4-fluorophenyl)-4-[1-(thiazol-2-yl)-2-(1-methylimidazol-5-yl)ethoxymethyl]benzoylamino}-4-methylsulfanylbutyrate; and tert-butyl (2S)-2-{2-(4-fluorophenyl)-4-[1-(thiazol-2-yl)-2-(1-methylimidazol-5-yl)ethoxymethyl]benzoylamino}-4-methylsulfonylbutyrate;

and pharmaceutically-acceptable salts thereof.

In another aspect the invention provides an inhibitor of ras farnesylation of Formula (1):

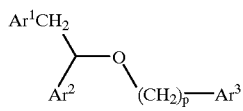

Formula (1)

wherein $Ar^1$ represents:

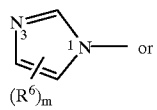

(A)

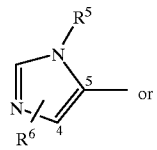

(B)

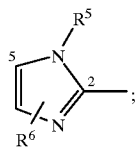

(C)

$Ar^2$ is phenyl or heteroaryl;

p is 0 or 1;

$Ar^3$ is phenyl, pyridinyl, pyridazinyl, pyrimidyl or pyrazinyl, the ring being substituted on ring carbon atoms by $R^2$ and $—(CH_2)_nR^3$ and wherein $Ar^3$ is attached to $Ar^1CH_2CH(Ar^2)O—$ by a ring carbon atom;

$R^2$ is a group of the Formula (2):

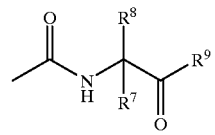

Formula (2)

wherein $R^7$ is hydrogen or $C_{1-4}$alkyl, $R^8$ is $—(CH_2)_q—R^{10}$ wherein q is 0–4 and $R^{10}$ is $C_{1-4}$alkylsulfanyl, $C_{1-4}$alkylsulfinyl, $C_{1-4}$alkylsulfonyl, hydroxy, $C_{1-4}$alkoxy, carbamoyl, $\underline{N}$-$C_{1-4}$alkyl carbamoyl, $\underline{N,N}$-(di$C_{1-4}$alkyl)carbamoyl, $C_{1-4}$alkyl, phenyl, thienyl, or $C_{1-4}$alkanoylamino, $R^9$ is hydroxy, $C_{1-4}$alkoxy, $C_{3-9}$cycloalkyloxy, heterocyclyloxy, heterocyclyl$C_{1-4}$alkoxy or —NH—$SO_2$—$R^{11}$ wherein $R^{11}$ represents, trifluoromethyl, $C_{1-4}$alkyl, phenyl, heteroaryl, aryl$C_{1-4}$alkyl or heteroaryl$C_{1-4}$alkyl;

or $R^2$ represents a lactone of Formula (3)

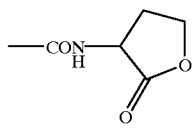

Formula (3)

the group of Formula (2) or (3) having $\underline{L}$ or $\underline{D}$ configuration at the chiral alpha carbon in the corresponding free amino acid;

n is 0, 1 or 2;

$R^3$ is phenyl or heteroaryl;

$R^3$ and $Ar^2$ are independently optionally substituted by up to three substituents selected from $C_{1-4}$alkyl, halogen, hydroxy, $C_{1-4}$alkoxy, $C_{1-4}$alkoxycarbonyl, $C_{1-4}$alkanoyl, $C_{1-4}$alkanoyloxy, amino, $C_{1-4}$alkylamino, di($C_{1-4}$alkyl)amino, $C_{1-4}$alkanoylamino, nitro, cyano, carboxy, $C_{1-4}$alkoxycarbonyl, thiol, $C_{1-4}$alkylsulfanyl, $C_{1-4}$alkylsulfinyl, $C_{1-4}$alkylsulfonyl, $C_{1-4}$alkanesulphonamido, $\underline{N}$-($C_{1-4}$alkylsulphonyl)-$\underline{N}$-$C_{1-4}$alkylamino, aminosulfonyl, $\underline{N}$-($C_{1-4}$alkyl)aminosulfonyl, $\underline{N,N}$-di($C_{1-4}$)aminosulfonyl, carbamoyl, $\underline{N}$-($C_{1-4}$alkyl)carbamoyl, $\underline{N,N}$-(di$C_{1-4}$alkyl)carbamoyl, carbamoyl$C_{1-4}$alkyl, $\underline{N}$-($C_{1-4}$alkyl)carbamoyl$C_{1-4}$alkyl, $\underline{N,N}$-(di$C_{1-4}$alkyl)carbamoyl$C_{1-4}$alkyl, hydroxy$C_{1-4}$alkyl and $C_{1-4}$alkoxy$C_{1-4}$alkyl;

$R^5$ is hydrogen, $C_{1-4}$alkyl, aryl$C_{1-4}$alkyl;

$R^6$ is hydrogen, $C_{1-4}$alkyl, hydroxy$C_{1-4}$alkyl, sulfanyl$C_{1-4}$alkyl, $\underline{N}$-($C_{1-4}$alkyl)amino$C_{1-4}$alkyl or aryl$C_{1-4}$alkyl; m is 0, 1 or 2;

or a pharmaceutically-acceptable salt, prodrug or solvate thereof.

In one aspect p is 0.

In another aspect p is 1.

Compounds of Formula (1) may form salts which are within the ambit of the invention. Pharmaceutically acceptable salts are preferred although other salts may be useful in, for example, isolating or purifying compounds.

When the compound contains a basic moiety it may form pharmaceutically-acceptable salts with a variety of inorganic or organic acids, for example hydrochloric, hydrobromic, sulphuric, phosphoric, trifluoroacetic, citric or maleic acid. A suitable pharmaceutically-acceptable salt of the invention when the compound contains an acidic moiety is an alkali metal salt, for example a sodium or potassium salt, an alkaline earth metal salt, for example a calcium or magnesium salt, an ammonium salt or a salt with an organic base which affords a pharmaceutically-acceptable cation, for example a salt with methylamine, dimethylamine, trimethylamine, piperidine, morpholine or tris-(2-hydroxyethyl)amine.

Solvates, for example hydrates, are also within the ambit of the invention and may be prepared by generally known methods.

Various forms of prodrugs are well known in the art. For examples of such prodrug derivatives, see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Pharm Bull, 32, 692 (1984).

Examples of pro-drugs include in vivo hydrolysable esters of a compound of the Formula I. Suitable pharmaceutically-acceptable esters for carboxy include $C_{1-8}$alkyl esters, $C_{5-8}$cycloalkyl esters, cyclic amine esters, $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl wherein alkyl, cycloalkyl and cyclicamino groups are optionally substituted by, for example, phenyl, heterocyclcyl, alkyl, amino, alkylamino, dialkylamino, hydroxy, alkoxy, aryloxy or benzyloxy, and may be formed at any carboxy group in the compounds of this invention.

According to another aspect of the invention there is provided a pharmaceutical composition comprising a compound as defined in Formula (1) or an individual compound listed above together with a pharmaceutically-acceptable diluent or carrier. A preferred pharmaceutical composition is in the form of a tablet.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 301 or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin ]Hanscb; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula (1) will naturally vary according to the nature and severity of the conditions, the age and sex of the animal or patient and the route of administration, according to well known principles of medicine. As mentioned above, compounds of the Formula (1) are useful in treating diseases or medical conditions which are due alone or in part to the effects of farnesylation of ras.

In using a compound of the Formula (1) for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

Compounds of this invention may be useful in combination with known anti-cancer and cytotoxic agents. If formulated as a fixed dose such combination products employ the compounds of this invention within the dosage range described herein and the other pharmaceutically active agent within its approved dosage range. Sequential use is contemplated when a combination formulation is inappropriate. According to another aspect of the invention there is provided a compound of Formula (1) or a pharmaceutically-acceptable salt thereof, for use as a medicament.

According to another aspect of the invention there is provided a compound of Formula (1) or a pharmaceutically-acceptable salt thereof, for use in preparation of a medicament for treatment of a disease mediated through farnesylation of ras.

According to another aspect of the present invention there is provided a method of treating ras mediated diseases, especially cancer, by administering an effective amount of a compound of Formula (1) or a pharmaceutically-acceptable salt thereof, to a mammal in need of such treatment.

Diseases or medical conditions may be mediated alone or in part by farnesylated ras. A particular disease of interest is cancer. Specific cancers of interest include:
  carcinoma, including that of the bladder, breast, colon, kidney, liver, lung, ovary, pancreas, stomach, cervix, thyroid and skin;
  hematopoietic tumors of lymphoid lineage, including acute lymphocytic leukemia, B-cell lymphoma and Burketts lymphoma;
  hematopoietic tumors of myeloid lineage, including acute and chronic myelogenous leukemias and promyelocytic leukemia;
  tumors of mesenchymal origin, including fibrosarcoma and rhabdomyosarcoma; and
  other tumors, including melanoma, seminoma, tetratocarcinoma, neuroblastoma and glioma.

The compounds of Formula (1) are especially useful in treatment of tumors having a high incidence of ras mutation, such as colon, lung, and pancreatic tumors. By the administration of a composition having one (or a combination) of the compounds of this invention, development of tumors in a mammalian host is reduced.

Compounds of Formula (1) may also be useful in the treatment of diseases other than cancer that may be associated with signal transduction pathways operating through Ras, e.g., neuro-fibromatosis.

Compounds of Formula (1) may also be useful in the treatment of diseases associated with CAAX-containing proteins other than Ras (e.g., nuclear lamins and transducin) that are also post-translationally modified by the enzyme farnesyl protein transferase.

Although the compounds of the Formula (1) are primarily of value as therapeutic agents for use in warm-blooded animals (including man), they are also useful whenever it is required to inhibit the effects of activation of ras by farnesylation. Thus, they are useful as pharmacological standards for use in the development of new biological tests and in the search for new pharmacological agents.

In another aspect the present invention provides a process for preparing a compound of the Formula (1) or a pharmaceutically-acceptable salt prodrug or solvate thereof which process comprises: deprotecting a compound of the formula (4)

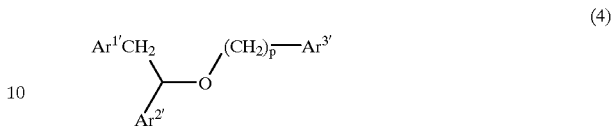

(4)

wherein $Ar^{1'}$ is $Ar^1$ or protected $Ar^1$, $Ar^{2'}$ is $Ar^2$ or protected $Ar^2$ and $Ar^{3'}$ is $Ar^3$ or protected $Ar^3$; wherein at least one protecting group is present; and thereafter if necessary:
  (i) forming a pharmaceutically-acceptable salt,
  (ii) forming a prodrug,
  (iii) forming a solvate.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain $C_{1-12}$alkyl groups (for example isopropyl, t-butyl); lower alkoxy lower alkyl groups (for example methoxymethyl, ethoxymethyl, isobutoxymethyl); lower aliphatic acyloxy lower alkyl groups, (for example acetoxymethyl, propionyloxymethyl, butyryloxymethyl, pivaloyloxymethyl); lower alkoxycarbonyloxy lower alkyl groups (for example 1-methoxycarbonyloxyethyl, 1-ethoxycarbonyloxyethyl); phenyl lower alkyl groups (for example benzyl, p-methoxybenzyl, o-nitrobenzyl, p-nitrobenzyl, benzhydryl and phthalidyl); tri(lower alkyl) silyl groups (for example trimethylsilyl and t-butyldimethylsilyl); tri(lower alkyl)silyl lower alkyl groups (for example trimethylsilylethyl); and $C_{2-6}$alkenyl groups (for example allyl and vinylethyl).

Methods particularly appropriate for the removal of carboxy protecting groups include for example acid-, base-, metal- or enzymically-catalysed hydrolysis.

Examples of hydroxy protecting groups include lower alkyl groups (for example t-butyl), lower alkenyl groups (for example allyl); lower alkanoyl groups (for example acetyl); lower alkoxycarbonyl groups (for example t-butoxycarbonyl); lower alkenyloxycarbonyl groups (for example allyloxycarbonyl); phenyl lower alkoxycarbonyl groups (for example benzoyloxycarbonyl, p-methoxybenzyloxycarbonyl, o-nitrobenzyloxycarbonyl, p-nitrobenzyloxycarbonyl); tri lower alkylsilyl (for example trimethylsilyl, t-butyldimethylsilyl) and phenyl lower alkyl (for example benzyl) groups.

Examples of amino protecting groups include formyl, aralkyl groups (for example benzyl and substituted benzyl, p-methoxybenzyl, nitrobenzyl and 2,4-dimethoxybenzyl, and triphenylmethyl); di-p-anisylmethyl and furylmethyl groups; lower alkoxycarbonyl (for example t-butoxycarbonyl); lower alkenyloxycarbonyl (for example allyloxycarbonyl); phenyl lower alkoxycarbonyl groups (for example benzyloxycarbonyl, p-methoxybenzyloxycarbonyl, o-nitrobenzyloxycarbonyl, p-nitrobenzyloxycarbonyl; tri-alkylsilyl (for example trimethylsilyl and t-butyldimethylsilyl); alkylidene (for example methylidene); benzylidene and substituted benzylidene groups.

Methods appropriate for removal of hydroxy and amino protecting groups include, for example, acid-, base-, metal- or enzymically-catalysed hydrolysis, for groups such as p-nitrobenzyloxycarbonyl, hydrogenation and for groups such as o-nitrobenzyloxycarbonyl, photolytically.

The reader is referred to Advanced Organic Chemistry, 4th Edition, by Jerry March, published by John Wiley & Sons 1992, for general guidance on reaction conditions and reagents. The reader is referred to Protective Groups in Organic Synthesis, 2nd Edition, by Green et al., published by John Wiley & Sons for general guidance on protecting groups.

Compounds of the formula (1) and (4) can be formed by:
(i) reacting a compound of the formula (5) with a compound of the formula (6)

(5)

(6)

or (iii) converting one value of $R^9$ in $R^2$ into another value of $R^9$;

or (iii) reacting a compound in which $R^2$ in $Ar^{3'}$ is carboxy with a compound of the formula (7):

(7)

wherein p, $Ar^{1'}$, $Ar^{2'}$, $Ar^{3'}$, $R^7$ and $R^8$ are as hereinabove defined, $R^{21}$ is $R^9$ or a carboxy protecting group and when p is 1, L is a leaving group, and when p is 0, L is hydroxy; and thereafter if necessary:
(i) removing any protecting groups;
(ii) forming a pharmaceutically-acceptable salt, prodrug or solvate thereof.

When p is 1, compounds of the formula (5) and (6) are conveniently reacted together in the presence of a base such as sodium hydride, butyl lithium or potassium tert-butoxide, in an aprotic solvent such as tetrahydrofuran (THF), dimethyl formamide (DMF) or dimethylacetamide (DMA), at a non-extreme temperature for example 0° C. to ambient temperature. L is preferably halo, mesyloxy or tosyloxy.

When p is 0, a compound of the formula (5) and a compound of the formula (6) are conveniently reacted together under conditions known for the Mitsunobu reaction. This typically involves reacting the reagents together in the presence of di($C_{1-4}$alkyl)azocarboxylate or 1', 1'-(azodicarbonyl)dipiperidine and a phosphorus reagent such as tributylphosphine or triphenylphosphine in an inert solvent such as toluene, benzene, tetrahydrofuran (THF) or diethylether, at non-extreme temperatures such as in the range −20° C. to ambient temperature (see Progress in the Mitsunobu Reaction. A Review, David L. Hughes, Organic Preparations and Procedures Int., 28 (2), 127–164 (1996)).

A compound of the formula (5) can be prepared by reducing a compound of the formula (8):

(8)

wherein $Ar^{1'}$ and $Ar^{2'}$ are as hereinabove defined. Suitable reducing agents include sodium borohydride or lithium aluminum hydride. Typically, when sodium borohydride is the reducing agent, an alcohol is used as solvent in a temperature range of ambient temperature to 60° C., and when lithium hydride is used diethyl ether or THF are used as solvents.

A compound of the formula (8) can be prepared by introducing $Ar^{1'}$ into a compound of the formula (9):

(9)

wherein $Ar^{2'}$ is as hereinabove defined and $L^1$ is a leaving group such as mesyloxy, tosyloxy, triflate or halo, preferably bromo. The reaction is conveniently carried out in the presence of a base such as sodium hydride, sodium hydroxide, butyl lithium or potassium carbonate. In some cases a base may not be necessary.

A compound of the formula (9) is conveniently formed from a compound of the formula (10):

(10)

wherein $Ar^{2'}$ is as hereinabove defined.

The compound of the formula (10) may be converted to a compound in which $L^1$ is bromo by bromination with, for example, N-bromosuccinimide, carbon tetrabromide or bromine or to a compound in which $L^1$ is chloro by chlorination with for example chlorine. When $L^1$ is mesyloxy or tosyloxy by oxidising the compound of the formula (10) to an alcohol and converting the hydroxy group to mesyloxy or tosyloxy using a meyl halide or tosyl halide.

When p is 1, a compound of the formula (6) is typically formed by introducing a leaving group into a compound of the formula $Ar^{3'}$—$CH_3$. When L is bromo $Ar^{3'}$—$CH_3$ can be brominated using for example N-bromosuccinimide, carbon tetrabromide or bromine. When L is chloro, a chlorinating agent such as chlorine could be used and when L is mesyloxy or tosyloxy, the methyl group in Ar³'—CH₃ is generally oxidised to the alcohol (or oxidised to the carboxylic acid and then reduced to the alcohol) and the hydroxy group converted to mesyloxy or tosyloxy with, for example, mesyl chloride or tosyl chloride. The compound of the formula Ar³'—CH₃ could be formed by introducing —(CH₂)$_n$R³ into a compound of the formula (11):

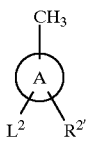
(11)

wherein R²' is as hereinabove defined, A is phenyl, pyridyl, pyrazinyl, pyrimidinyl or pyridazinyl and L² is a leaving group. When n is 0 and R³ is phenyl, the compound of the formula (11) is conveniently reacted with phenyl boronic acid in the presence of a palladium catalyst such as palladium tetrakis (triphenylphosphine) palladium (0) under conditions known for the Suzuki reaction (Synth.Commun. 11, 513 (1981)). An aprotic organic solvent such as dimethyl ether (DME), dimethylsulphoxide (DMSO) or THF is generally used and a base such as sodium bicarbonate, sodium carbonate and sometimes sodium hydroxide. A fluoride such as cesium fluoride could be used instead of the base (J. Org. Chem. 1994, 59, 6095–6097). Preferably L² is bromo or triflate. When n is 1 and R³ is phenyl, the compound of the formula (11), bromo or chloro, is conveniently reacted with a benzylzinc chloride or a benzyl-magnesium bromide in the presence of a nickel or palladium catalyst, such as bis (triphenylphosphine)palladium (11) chloride or Pd₂(dba)₃, in an inert organic solvent such as tetrahydrofurnan (THF). For example see the conditions used for the 'Nagishi' reaction (J. Org. Chem. 42 (10), 1821–1822, 1977).

When n is 2 and R³ is phenyl, the compound of the formula (11) is conveniently reacted with a styrene under conditions known for the Heck reaction. Briefly this involves an inorganic or organic base such as triethylamine, a palladium catalyst such as bis (o-tolylphosphine)palladium (II) chloride in water. (Acc. Chem. Res. 12, 146–151 (1979), J. Organometallic Chem. 486,259–262 (1995)).

The resulting alkene can then be reduced using standard methods known in the art, for example, catalytic hydrogenation.

Alternatively the alkyne could be formed by reacting a compound of the formula (11) wherein L² is triflate or bromo with a phenyl acetylene in the presence of an organic base such as triethylamine and a palladium catalyst such as palladium tetrakis (triphenylphosphine). For example see the conditions used for the Sonogashira reaction (J. Org. Chem. 1993,58, 6614–6619).

The resultant alkyne can be reduced using standard methods known in the art, for example, catalytic hydrogenation.

When p is 0, the compound of the formula (6) can be formed by introducing —(CH₂)$_n$R³ into a compound of the formula (12).

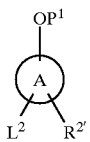
(12)

wherein R²', A and L² are as hereinbefore defined, and P¹ is a hydroxy-protecting group.

When n is 0 and R³ is phenyl, the compound of the formula (12) is conveniently reacted with phenyl boronic acid in the presence of a palladium catalyst as described above for when p is 1.

When p is 0, L² is preferably bromo.

When n is 1, and R³ is phenyl, the compound of the formula (12) wherein L² is preferably bromo or chloro, is conveniently reacted with benzylzinc chloride or benzyl-magnesiumn bromide under similar conditions to those described above for when p is 1. When n is 2, the compound of the formula (12) is conveniently reacted with styrene under conditions know for the Heck reaction.

The resulting alkene can then be reduced using standard methods known in the art, for example, catalytic hydrogenation.

Alternatively, the alkyne could be formed by reacting a compound of the formula (12) wherein L² is triflate or bromo with a phenyl acetylene in the presence of an organic base such as triethylene and a palladium catalyst such as palladium tetrakis (triphenylphosphine). For example see the conditions used for the Sonogashira reaction (J. Org. Chem. 1993, 58, 6614–6619).

The resultant alkyne can be reduced using standard methods known in the art, for example, catalytic hydrogenation.

The protecting group P¹ can then be removed to leave a compound of the formula (6).

A compound of the formula (1) or (4) could be prepared via a sequence of steps from a compound of the formula (12).

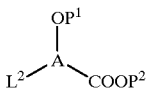
(12)

When p is 1, a compound of the formula (1) or (4) could be prepared via a sequence of steps from a compound of the formula (13):

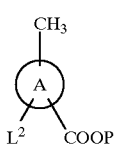
(13)

wherein L² and A are as hereinabove defined and P is a carboxy protecting group.

L² can be replaced with the group —(CH₂)$_n$R³ using the methodology described above. The methyl group could then be converted to a —CH₂L group and the resultant compound reacted with a compound of the formula (5). The carboxy group in the resultant product can then be deprotected and reacted with the appropriate amino acid derivative to form R², under conditions described hereinbelow, and hence a compound of the formula (1) or (4).

When p is 0, a compound of the formula (1) or (4) could be prepared from a compound similar to that of formula (13) but wherein the methyl group is replaced by a protected-hydroxy group. $L^2$ can then be converted to —$(CH_2)_nR^3$, the hydroxy group removed and the resultant compound reacted with a compound of the formula (5). Subsequent steps are also similar to those described above for when p is 1.

A compound of the formula (1) in which $R^9$ in $R^2$ is alkoxy can conveniently be hydrolysed to another compound of the formula (1) in which $R^9$ is hydroxy using standard methods known in the art. For example, the alkoxy group could be subjected to acid or base hydrolysis with, for example, in the case of base hydrolysis, aqueous sodium hydroxide solution in an organic solvent such as an alcohol in a temperature range of ambient temperature to 60° C. When $R^9$ is a hydroxy group the carboxy group in a compound of the formula (1) can be converted to an acylsulphonamide by reacting the carboxy group with the appropriate sulphonamido group in the presence of an organic base such as triethylamine or dimethylaminopyridine, in an inert organic solvent such as dimethylformamide (DMF), in temperature range of −20° C. to ambient temperature.

The reaction between a compound in which $R^2$ in $Ar^{3'}$ is carboxy and a compound of the formula (7) is generally carried out in the presence of a reagent that converts the carboxy group into a reactive ester, for example a carbodiimide such as 1-(3-dimethylaminopropyl)-3-ethylcarbodiimide (EDC) or pentafluorophenyl, and in the presence of an organic base such as N-methylmorpholine or dimethylaminopyridine (DMAP). The reaction is usually carried out in the temperature range of −20° C. to ambient temperature. The reagent, 1-hydroxybenzotriazole, is often added to assist the reaction (see Chem. Ber. 103, 788, 2024 (1970), J. Am. Chem. Soc. 93, 6318 (1971), Helv. Chim. Acta. 56, 717, (1973)). Suitable solvents include DMF and dichloromethane.

A compound of the formula (1) in which $R^2$ in $Ar^{3'}$ is carboxy can be prepared by reacting a compound of the formula (5) with a compound of the formula (6) wherein $R^2$ in $Ar^{3'}$ is protected carboxy and subsequently removing the protecting group.

Optionally substituents in a compound of the formula (1) and (4) or intermediates in their preparation may be converted into other optional substituents. For example an alkylthio group may be oxidised to an alkylsulphinyl or alkylsulphonyl group, a nitro group reduced to an amino group, a hydroxy group alkylated to a methoxy group, or a bromo group converted to an alkylthio group.

Various substituents may be introduced into compounds of the formulae (1) and (4) and intermediates in this preparation, when appropriate, using standard methods known in the art. For example, an acyl group or alkyl group may be introduced into an activated benzene ring using Friedel-Crafts reactions, a formyl group by formulation with titanium tetrachloride and dichloromethyl ethyl ester, a nitro group by nitration with concentrated nitric acid concentrated sulphuric acid and bromination with bromine or tetra(n-butyl)ammonium tribromide.

Alternatively, a compound similar to a compound of the formula (12) but which contains a methyl group instead of —COOP group could be used as the starting material and both methyl groups oxidised to carboxylic acids, one selectively reduced to an alcohol with a reducing agent such as borane in THF, and the hydroxy converted to a leaving group.

It will be appreciated that, in certain steps in the reaction sequence to compounds of the formula (1), it will be necessary to protect certain functional groups in intermediates in order to prevent side reactions. Deprotection may be carried out at a convenient stage in the reaction sequence once protection is no longer required.

Biological activity was tested as follows:

(i) In-vitro Assay

The following stock solutions were used and the assays were conducted in 96 well plates: TRIS Buffer (500 mM TRIS, 50 mM $MgCl_2.6H_2O$, pH=8.0); Farnesyl pyrophosphate (6.4 mg/ml); Aprotinin (1.9 mg/ml); Ki-ras (0.5 mg/ml, stored at −80° C.); Acid ethanol (850 ml absolute ethanol+150 ml concentrated HCl).

Farnesyl protein transferase (FPT) was partially purified from human placenta by t ammonium sulphate fractionation followed by a single Q-Sepharose™ (Pharmacia, Inc) anion exchange chromatography essentially as described by Ray and Lopez-Belmonte (Ray K P and Lopez-Belmonte J (1992) Biochemical Society Transactions 20 494–497). The substrate for FPT was Kras (CVIM C-terminal sequence). The cDNA for oncogenic val12 variant of human c-Ki-ras-2 4B was obtained from the plasmid pSW11-1 (ATCC). This was then subcloned into the polylinker of a suitable expression vector e.g. pIC147. The Kras was obtained after expression in the E. coli strain, BL21. The expression and purification of c-KI-ras-2 4B and the val12 variant in E. coli has also been reported by Lowe et al (Lowe P N et al. J. Biol. Chem. (1991) 266 1672–1678). The farnesyl protein transferase enzyme preparation was stored at −80° C.

The farnesyl transferase solution for the assay contained the following: dithiothreitol (DTT)(0.6 ml of 7.7 mg/ml), TRIS buffer (0.6 ml), aprotinin (0.48 ml), distilled water (1.2 ml), farnesyl transferase (0.6 ml of the crude enzyme preparation prepared as described above), zinc chloride (12 $\mu$l of 5 mM). This was left at ambient temperature for 30 minutes. After this incubation 60 $\mu$l Ki-ras solution was added and the whole left to incubate for a further 60 minutes prior to use in the assay.

Assays were performed in 96 well plates as follows: 10 $\mu$l of test compound solution was added to each well. Then 30 $\mu$l farnesyl transferase solution (above) was added and the reaction started by addition of 10 $\mu$l radiolabelled farnesyl pyrophosphate solution. After 20 minutes at 37° C. the reaction was stopped with 100 $\mu$l acid ethanol (as described in Pompliano D L et al (1992) 31 3800–3807). The plate was then kept for 1 hour at 4° C. Precipitated protein was then collected onto glass fibre filter mats (B) using a Tomtec™ cell harvester and tritiated label was measured in a Wallac™1204 Betaplate scintillation counter. Test compounds were added at appropriate concentrations in DMSO (3% final concentration in test and vehicle control).

(ii) Intracellular Farnesylation Assay

HER313A cells (Grand et al, 1987 Oncogene 3, 305–314) were routinely cultured in Dulbecos Modified Essential Medium (DMEM) plus 10% foetal calf serum (FCS). For the assay HER313A cells were seeded at 200,000 cells/well in a volume of 2.5 ml in a 6 well tissue culture plate. After an overnight incubation at 37° C. in 10% $CO_2$ the medium was removed and replaced with methionine-free minimal essential medium (MEM) and the cells incubated as above for 2 hours. After this time the medium was removed and replaced by methionine-free MEM (1 ml) and test compound (1–3 $\mu$l). The plates were then incubated for a further 2 hours as described above and then 30 $\mu$Ci of $^{35}$S-methionine added to each well. The plate was then incubated overnight as described above. The medium was then removed and the cells were lysed with lysis buffer (1 ml) (composed of 1000 ml phosphate buffered saline, 10 ml trition X-100, 5 g sodium deoxycholate, 1 g sodium dodecylsulphate) containing aprotinin (10 μl/ml), the plate scrapped and then left for 10 minutes at 4° C. The lysate was then clarified by centrifugation. To 0.8 ml of the clarified lysate 80 μl of Y13-259 pan-Ras antibody (isolated from the hybridoma—American Tissue Culture Collection Accession Number CRL-1742) (final concentration approximately 1 μg/ml, the exact working concentration was optimised for each batch of antibody isolated) and protein G beads (30 μl of 0.5 μg/ml) were added and the mixture incubated overnight with constant agitation. The pellet was then collected by centrifugation, washed and separated by SDS PAGE using a 15% gel. Radioactive bands were detected using a phosphor imager system.

(iii) Morphology and Proliferation Assay

MIA PaCa 2 cells (American Tissue Culture Collection Accession Number: CRL-1420) were routinely cultured in Dulbecos Modified Essential Medium (DMEM) plus 10% FCS in a 162 cm² tissue culture flask. For the assay the cells were seeded at 16,000 cells/well, in 12 well plates, in DMEM containing 5% charcoal dextran treated stripped FCS (1 ml)(obtained from Pierce and Warriner). The cells were then incubated overnight at 37° C. in 10% $CO_2$. Test compound was then added (10 μl) and the cells incubated for 6 days as described above. On days 1, 2, 3 and 6 the cells were monitored for signs of morphological change and toxicity. On day 6 the cells were removed from the plate using trypsin/EDTA and counted to determine the proliferation rate.

Although the pharmacological properties of the compounds of the Formula (1) vary with structural change as expected, in general compounds of the Formula (1) possess an $IC_{50}$ in the above test in the range, for example, 0.0005 to 50 μM. Thus by way of example the compound of Example 2 herein has an $IC_{50}$ of approximately 0.001 μM. No physiologically unacceptable toxicity was observed at the effective dose for compounds tested of the present invention.

The invention will now be illustrated in the following nonlimiting Examples in which, unless otherwise stated:

(i) evaporations were carried out by rotary evaporation in vacuo and work-up procedures were carried out after removal of residual solids by filtration;

(ii) operations were carried out at ambient temperature, that is in the range 18–25° C. and under an atmosphere of an inert gas such as nitrogen or argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) C18 reverse phase silica separation;

(iv) yields are given for illustration only and are not necessarily the maximum attainable;

(v) the end-products of the Formula (1) have satisfactory microanalyses and their structures were confirmed by nuclear magnetic resonance (NMR) and mass spectral techniques; chemical shift values were measured on the delta scale; the following abbreviations have been used: s, singlet; d, doublet; t or tr, triplet; m, multiplet; br, broad;

(vi) intermediates were not generally fully characterised and purity was assessed by thin layer chromatographic, HPLC, infra-red (IR) or NMR analysis;

(vii) melting points are uncorrected and were determined using a Mettler SP62 automatic melting point apparatus or an oil-bath apparatus; melting points for the end-products of the Formula (1) were determined after crystallisation from a conventional organic solvent such as ethanol, methanol, acetone, ether or hexane, alone or in admixture; and (viii) the following abbreviations have been used:

| | |
|---|---|
| ADDP | 1,1'-(azodicarbonyl)dipiperidine |
| DEAD | diethyl azodicarboxylate |
| DMAP | 4-dimethylaminopyridine |
| DMF | dimethylformamide |
| EDC | 1-(3-dimethylaminopropyl)-3-ethyl-carbodiimide |
| HOBT | 1-hydroxybenzotriazole |
| Pd(dppb)Cl₂ | [1,4-bis(diphenylphosphino)butane]palladium(II) dichloride |
| MCPBA | m-chloroperoxybenzoic acid |
| NMM | N-methylmorpholine |
| TEA | triethylamine |
| TFA | trifluoroacetic acid |
| THF | tetrahydrofuran |

EXAMPLE 1

Methyl (2S)-2-{2-(4-fluorophenyl)-4-[2-(imidazol-1-yl)-1-4-fluorophenyl)ethoxymethyl]benzoylamino}-4-methlsulfanylbultyrate A mixture of 2-(4-fluorophenyl)-4-[2-(imidazol-1-yl)-1-(4-fluorophenyl)ethoxymethyl]benzoic acid (0.522 g; 1.2 mmol), methyl (2S)-2-amino-4-methylsulfanyl)butanoate hydrochloride (L-methionine methyl ester hydrochloride) (0.24 g; 1.2 mmol), HOBT (0.163 g; 1.2 mmol), EDC (0.23 g; 1.2 mmol) and N-methylmorpholine (0.132 ml; 1.2 mmol) in dichloromethane (15 ml) was stirred under an argon atmosphere for 5 hours. After evaporation to dryness, the residue was purified by flash column chromatography eluting with petroleum ether/ethanol (98:2). The resulting compound was dissolved in dichloromethane (2 ml), treated at 0° C. with a 3.8N solution of HCl in ether (0.265 ml) and diluted with ether (100 ml) to precipitate the hydrochloride salt which was filtered and dried to give the title compound.

Yield: 75% $^1$H NMR (DMSO d$_6$+CF$_3$COOD, 400 MHz) δ: 1.8–1.95 (2H, m); 2 (3H, s); 2.15–2.35 (2H, m); 3.64 (3H, s); 4.34–4.55 (5H, m); 4.9 (1H, m);7.1–7.7 (13H, m); 8.6 (1H, d); 9.05 (1H, s). Anal. Calculated for $C_{31}H_{31}F_2N_3O_4S$, $H_2O$, 0.9 HCl; C, 60.44; H, 5.28; N, 6.82; S, 5.20; Found: C, 60.07; H, 5.39; N, 6.69; S, 4.95; MS (ESI) m/z 580 (MH⁺).

The starting material was prepared as follows:

Triflic anhydride (170 ml; 1.01 mol) was added to a solution of methyl 2-hydroxy-4-methylbenzoate (153 g; 0.92 mol) in pyridine (1.5 l), at 0° C., The mixture was stirred at ambient temperature overnight. After evaporation of the pyridine, the residue was acidified to pH 3.5 with 6N HCl and extracted with ether. The organic phase was evaporated and the residue purified by flash column chromatography eluting with a gradient of 0–5% ethyl acetate/petroleum ether to give methyl 2-trifluoromethylsulfonyloxy-4-methylbenzoate (245 g; 90%).

$^1$H NMR (CDCl$_3$, 400 MHz) δ: 1.55 (3H,s); 2.45 (3H, s); 3.94 (3H, s); 7.09 (1H, s); 7.26 (1H, s); 7.98(1H, d).

Tetrakis(triphenylphosphine) palladium (9 g; 7.8 mmol) and ethanol (780 ml) was added to a suspension of methyl 4-methyl-2-trifluoromethanesulphonyloxybenzoate (58 g; 0.195 mol), 2M aqueous solution of sodium carbonate (250 ml; 0.5 mol), 4-fluorophenylboronic acid (30 g ; 0.214 mol)

and lithium chloride (16.5 g ; 0.39 mol) in toluene (1.65 ml), under an argon atmosphere, The mixture was refluxed for 4 hours, diluted with ethyl acetate (1 l) and washed with aqueous sodium hydroxide solution 1N (1 l). The organic phase was evaporated and the residue purified by flash column chromatography using ethyl acetate|petroleum ether (95:5) to give methyl 2-(4-fluorophenyl)-4-methylbenzoate (46.8 g; 99%).

$^1$H NMR (CDC$_3$, 400 MHz) δ: 2.41 (3H, s); 3.64 (3H, s); 7–7.03 (6H, m); 7.7 (1H, d).

A solution of methyl 2-(4-fluorophenyl)-4-methylbenzoate (54.18 g; 0.22 mol), N-bromosuccinimide (39.6 g; 0.22 mol), 2,2'-azobis(2-methylproprionitrile) (0.25 g; 1.5 mmol) and benzoylperoxide (0.25 g; 1 mmol) in tetrachloromethane (550 ml) was heated at reflux for 6 hours. The solid was filtered and the filtrate evaporated to give methyl 4-bromomethyl-2-(4-fluorophenyl)benzoate as an oil (79.7 g; 79%) which was used in the next step without purification.

$^1$H NMR (CDCl$_3$, 400 MHz) δ: 3.65 (3H, s); 4.51 (2H, s); 7–7.5 (6H, m); 7.82 (1H, m).

To a solution of 1-(4-fluorophenyl)-2-(imidazol-1-yl) ethanol (0.628 g; 3 mmol) in THF (30 ml) was added sodium hydride, under an argon atmosphere, (0.15 g; 3.6 mmol). After stirring for 10 minutes, methyl 4-bromomethyl-2-(4-fluorophenyl)benzoate (2 g; 6.09 mmol) was added. The mixture was stirred at ambient temperature overnight. After evaporation to dryness, the residue was extracted with ethyl acetate and purified by flash column chromatography eluting with dichloromethane/ethanol (97:3) to give methyl 2-(4-fluorophenyl)-4-[2-(imidazol-1-yl)-1-(4-(fluorophenyl) ethoxymethyl]benzoate as an oil (0.635 g; 46%).

$^1$H NMR (CDCl$_3$, 400 MHz) δ: 3.65 (3H, s); 4–4.6 (5H, m); 6.87 (1H, s); 6.98 (1H, s); 7–7.3 (10H, m); 7.41 (1H, d); 7.80 (1H, d).

Methyl 2-(4-fluorophenyl)-4-[2-(imidazol-1-yl)-1-(4-fluorophenyl)ethoxymethyl]benzoate (0.635 g; 1.41 mmol) in methanol (15 ml) was treated with 2N aqueous sodium hydroxide solution (1.77 ml; 3.54 mmol) at ambient temperature for 8 hours. After evaporation of the methanol, the residue was taken up in water, the pH adjusted to 4.8 with 2N HCl and extracted with dichloromethane to give 2-(4-fluorophenyl)-4-[2-(imidazol-1-yl)-1-(4-fluorophenyl) ethoxymethyl]benzoic acid after evaporation as a foam (0.522 g; 85%).

$^1$H NMR (CDCl$_3$, 400 MHz) δ: 4–4.25 (3H, m); 4.4–4.7 (2H, m); 6.9–7.5 (12H, m); 7.8 (2H, m).

EXAMPLE 2

(2S)-2-{2-(4-fluorophenyl)-4-[2-(imidazol-1-yl)-1-(4-fluorophenyl)ethoxymethyl]benzoylamino]-4-methylsulfanylbutyric acid A solution of methyl (2S)-2-{2-(4-fluorophenyl)-4-[2-(imidazol-1-yl)-1-(4-fluorophenyl)ethoxymethyl] benzoylamino}-4-methylsulfanyl butyrate (0.135 g; 0.23 mmol) in methanol (10 ml) was treated with 2N aqueous sodium hydroxide solution (0.24 ml) and heated at 60° C. for 4 hours. After evaporation of the methanol, the aqueous reaction mixture was acidified to pH 7.5 with 6N HCl and purified on reverse phase silica eluting with a gradient of 50–60% methanol/ammonium carbonate buffer (2 g/l, pH 7). The appropriate fractions were concentrated and freeze-dried to give the title compound as a solid.

Yield: 65%; $^1$H NMR (DMSO d$_6$, 400 MHz) δ: 1.7–1.9 (2H, m); 2 (3H, s); 2.15–2.35 (2H, m); 4.2–4.5 (5H, m); 4.8 (1H, m); 6.83 (1H, m); 7.1–7.6 (14H, m); 8.4 (1H, s). Anal. Calculated for C$_{30}$H$_{29}$F$_2$N$_3$O$_4$S, H$_2$O; C, 61.74; H, 5.35, N, 7.2; S, 5.49; Found: C, 61.97; H, 5.26; N, 7.14; S, 5.05; MS (ESI) m/z 566 (MH$^+$).

EXAMPLE 3

Tert-butyl (2S)-2-{2-(4-fluorophenyl)-4-[2-(imidazol-1-yl)-1-(4-fluorophenyl) ethoxymethylbenzoylamino}-4-methylsulfanylbutyrate Tert-butyl (2S)-2-{2-(4-fluorophenyl)4-[2-(imidazol-1-yl)-1-(4-fluorophenyl)ethoxymethylbenzoylamino}-4-methylsulfanylbutyrate was prepared by a similar method to that used for Example 1, but using tert-butyl (2S)-2-amino-4-methylsulfanyl)butanoate (L-methionine tert-butyl ester) in place of L-methionine methyl ester.

The compound was purified by flash column chromatography dichloromethane/ethanol, (98:2) and further purified on reverse phase silica eluting with a gradient of 60–80% methanol/ammonium carbonate buffer (2 g/l, pH 7).

Yield: 52%; $^1$H NMR (CDCl$_3$, 400 MHz) δ: 1.42 (9H, s); 1.7–2 (2H, m); 2.15–2.25 (2H, m); 4–4.3 (3H, m); 4.45–4.6 (3H, m); 6 (1H, m); 6.8–7.6(14H, m). Anal. Calculated for C$_{34}$H$_{37}$F$_2$N$_3$O$_4$S; C, 65.68; H, 6.0; N, 6.76; S, 5.16; Found: C, 65.33; H, 6.11; N, 6.66; S, 4.84; MS (ESI) m/z 622 (MH$^+$).

EXAMPLE 4

Methyl (2S)-2-{2-(4-fluorophenyl)-4-[2-(imidazol-1-yl)-1-(thiazol-2-yl)ethoxymethyl]benzoylamino}-4-methylsulfanylbutyrate The title compound was prepared using a similar method to that used for Example 1, but using 1-(thiazol-2-yl)-2-(imidazol-1-yl)-ethanol in place of 1-(4-fluorophenyl)-2-(imidazol-1-yl)-ethanol.

Yield: 76%; $^1$H NMR (DMSO d$_6$+AcOD) δ: 1.75–2 (2H, m); 2 (3H, s); 2.15–2.35 (2H, m); 3.64 (3H, s); 4.37 (1H, m); 4.65–4.9 (4H, m); 5.37 (1H, m); 7.15–7.95 (11H, m); 8.62(1H, d); 9.09 (1H, s). Anal. Calculated for C$_{28}$H$_{29}$FN$_4$O$_4$S$_2$, 0.8 H$_2$O, 1HCl; C, 54.28; H, 5.14; N, 9.04; S, 10.35; Found: C, 54.30; H, 5.16; N, 9.30; S; 10.24; MS (ESI) m/z 569 (MH$^+$).

EXAMPLE 5

(2S)-2-{2-(4-Fluorophenyl)-4-[2-(imidazol-1-yl)-1-(thiazol-2-yl)ethoxymethyl]benzoylamino}-4-methylsulfanyl butyric acid The title compound was prepared by a similar method to that used for Example 2.

Yield: 78%; $^1$H NMR (DMSO d$_6$+CF$_3$COOD 400 MHz) δ: 1.8–2 (2H, m); 2 (3H, s); 2.2–2.4 (2H, m); 4.3 (1H, m); 4.6–4.9 (4H, m); 5.35 (1H, m); 7.1–7.4 (6H, m); 7.5–7.7 (2H, m); 7.8 (1H, m); 7.9 (1H, m); 9.09 (1H, s). Anal. Calculated for C$_{27}$H$_{27}$FN$_4$O$_4$S$_2$, 0.5 H$_2$O; C, 57.53; H, 5.01; N, 9.94; S, 11.38; Found: C, 57.15; H, 4.95; N, 9.98; S, 10.73; MS (ESI) m/z 555 (MH$^+$).

EXAMPLE 6

Methyl (2S)-2-{2-(4-fluorophenethyl)-5-[2-(imidazol-1-yl)-1-(4-fluorophenyl)-ethoxymethyl] benzoylamino}-4-methylsulfanyl butyrate The title compound was prepared by a similar method to that used for Example 1, but using methyl 5-bromomethyl- 2-(4-fluorophenethyl) benzoate in place of methyl 4-bromomethyl-2-(4-fluorophenyl)benzoate.

Yield: 71%; $^1$H NMR (DMSO d$_6$+CF$_3$COOD, 400 MH) δ: 1.9–2.15 (2H, m); 2.05 (3H, s); 2.4–2.7 (2H, m); 2.75–3.1 (4H, m); 3.66 (3H, m); 4.25–4.7 (5H, m); 4.95 (1H, m); 7–7.30 (9H, m); 7.3–7.75 (4H, m); 9.04 (1H, s). Anal. Calculated for C$_{33}$H$_{35}$F$_2$N$_3$O$_4$S, 0.5 H$_2$O, 1HCl; C, 60.68; H, 5.71; N, 6.43; S, 4.91; Found: C, 60.29; H, 5.88; N, 6.37; S, 4.58; MS (ESI) m/z 608 (MH$^+$).

The starting material was prepared as follows:

A mixture of dimethyl 4-bromoisophthalate (54.75 g., 200.5 mmol), water (330 ml), tributylamine (55.63 g., 300.7 mmol), 4-fluorostyrene(55.63 g., 300.7 mmol) and bis (triphenylphoshine)palladium(II)chloride (2.81 g., 4.01 mmol) was heated at reflux with stirring under an inert atmosphere for 6 hours. The reaction was cooled to ambient temperature and acidified to pH 2 with 2M HCl (700 ml). The aqueous layer was removed and the residual solid washed with water (2 L), dissolved in dichloromethane (1 L) and passed through a pad of silica, eluting with more dichloromethane(2 L). Evaporation of the dichloromethane gave a solid, which was washed with iso-hexane(1 L) and dried to give methyl 4-[2-(4-fluorophenylethenyl]-3-methoxycarbonylbenzoate (56.75 g) as a pale yellow solid.

NMR data (CDCl$_3$) δ: 3.96 (6H, 2s), 7.01–7.10 (3H, m), 7.49–7.57 (2H, m), 7.80 (1H, d), 7.97 (1H, d), 8.16 (1H, dd), 8.60 (1H, s). MS m/e 315.3 (M+H)$^+$.

A mixture of methyl 4-[2-(4-fluorophenyl)ethenyl]-3-methoxycarbonylbenzoate (56.75 g, 180.6 mrol), ethyl acetate (900 ml), 10% palladium on carbon (6 g) was stirred under an hydrogen atmosphere for 6 hours. The catalyst was filtered and replaced with fresh catalyst (6 g). The reaction was then stirred under an hydrogen atmosphere for 16 hours. The catalyst was filtered and the filtrate evaporated to dryness to give, as a colourless gum, methyl 4-(4-fluorophenethyl)-3-methoxycarbonylbenzoate (55.00 g).

NMR data (CDCl$_3$) δ: 2.84–2.93 (2H, m), 3.25–3.33 (2H, m), 3.93 (6H, 2s), 6.90–7.00 (2H, m), 7.09–7.16 (2H, m), 7.22–7.28 (1H, m), 8.05 (9H, dd), 8.57 (1H, s). MS m/e 317.3 (M+H)$^+$.

A mixture of methyl 4-(4-fluorophenethyl)-3-methoxycarbonylbenzoate (51.00 g., 161.22 mmol), dioxane (650 ml), methanol (650 ml), sodium hydroxide (7.10 g., 177.35 mmol) and water (100 ml) was stirred at ambient temperature under an inert atmosphere for 16 hours. The reaction was evaporated to dryness, water (500 ml) added to the residue and the mixture extracted with diethylether. The organic extracts were dried and evaporated to dryness to give recovered methyl 4-(4-fluorophenethyl)-3-methoxycarbonylbenzoate (7 g). The aqueous layer was acidified to pH 2 with 2M HCl (300 ml) and extracted with ethyl acetate (300 ml). The organic extracts were dried, filtered and evaporated to dryness to give, as a white solid, 4-(4-fluorophenethyl)-3-methoxycarbonylbenzoic acid (42.00 g).

NMR data (DMSO d$_6$) δ: 2.77–2.85 (2H, m), 3.16–3.24 (2H, m), 3.85 (3H, s), 7.04–7.12 (2H, m), 7.17–7.25 (2H, m), 7.45 (1H, d), 8.00 (1H, dd), 8.535 (1H, s). MS m/e 301.4 (M-H)$^-$.

A mixture of 4-(4-fluorophenethyl)-3-methoxycarbonylbenzoic acid (16.5 g, 54.88 mmol), tetrahydrofuran (500 ml) and borane in tetrahydrofuran (1M. complex, 218 mls, 218 mmol) was stirred under an inert atmosphere at reflux for 6 hours. The reaction was cooled to ambient temperature and methanol (1 L) was added. It was then evaporated to dryness to give a dark oil which was purified by flash column chromatography using iso-hexane/ethyl acetate (1:1) as eluant to give, as a clear gum, methyl 2-(4-fluorophenethyl)-5-hydroxymethylbenzoate (13.10 g).

NMR data (CDCl$_3$) δ: 1.74 (1H, t), 2.82–2.92 (2H, m), 3.17–3.27 (2H, m), 3.91 (3H, s), 4.71 (2H, d), 6.91–6.99 (2H, m), 7.11–7.20 (3H, m), 7.41 (1H, d), 7.91 (1H, s). MS m/e 289 (M+H)$^+$.

A mixture of methyl 2-(4-fluorophenethyl)-5-hydroxymethylbenzoate (13.10 g., 45.43 mmol), carbon tetrabromide(18.08 g, 54.52 mmol) and triphenylphosphine (14.30 g, 54.52 mmol) in dichloromethane (400 ml) was stirred at ambient temperature for 4 hours. More carbon tetrabromide (7.54 g, 23.00 mmol) and triphenylphosphine (5.96 g, 23.00 mmo.) in dichloromethane (50 ml) were added. The reaction was applied directly to a silica flash column and eluted with iso-hexane/ethyl acetate (92.5:7.5) to give methyl 2-(4-fluorophenethyl)-5-bromomethylbenzoate (9.30 g) as a clear gum.

NMR data (CDCl$_3$) δ: 2.81–2.91 (2H, m), 3.19–3.27 (2H, m), 3.91 (3H, s), 4.48 (2H, s), 6.91–7.00 (2H, m), 7.12–7.17 (3H, m), 7.44 (1H, dd), 7.95 (1H, s). MS m/e's 351 and 353 (M+H)$^+$.

EXAMPLE 7

(2S)-2-{2-(4-fluorophenethyl)-5-[2-(imidazol-1-yl)-1-(4-fluorophenyl)ethoxymethyl]benzoylamino}-4-methylsulfanylbultyric acid The title compound was prepared by a similar method to that used for Example 2.

Yield: 73%; $^1$H NMR (DMSO d$_6$+CF$_3$COOD, 400 MHz) δ: 1.9–2.15 (2H, m), 2.04 (3H, s); 2.5–2.7 (2H, m); 2.75–3.1 (4H, m); 4.2–4.6 (5H, m); 4.91 (1H, m); 7–7.75 (13H, m); 9.03 (1H, s). Anal. Calculated for C$_{32}$H$_{33}$F$_2$N$_3$O$_4$S, H$_2$O; C, 62.83; H, 5.77; N, 6.87; S, 5.24; Found: C, 62.48; H, 5.66; N, 6.87; S, 5.06; MS (ESI) m/z 594 (MH$^+$).

EXAMPLE 8

Methyl (2S)-2-{2-(4-(fluorobenzyl)-5-[1-(4-fluorophenyl)-2-(imidazol-1-yl)ethoxymethyl] benzoylamino}-4-methylsulfanylbutyrate The title compound was prepared by a similar method to that used for Example 1, but using methyl 5-bromomethyl-2-(4-fluorobenzyl)benzoate in place of methyl 4-bromomethyl-2-(4-fluorophenyl)benzoate.

Yield: 48%; $^1$H NMR (CDCl$_3$, 400 MHz) δ: 2–2.25 (2H, m); 2 (3H, s); 2.45–2.65 (2H, m); 3.78 (3H, s); 4.1–4.9 (8H, m); 6.9–7.45 (14H, m); 9 (1H, d). Anal. Calculated for C$_{32}$H$_{33}$F$_2$N$_3$O$_4$S, 0.5 H$_2$O, 1HCl; C, 60.13; H, 5.52; N, 6.57; S, 5.02; Found: C, 60.00; H, 5.57; N, 6.61; S, 4.87; MS (ESI) m/z 594 (MH$^+$).

The starting material was prepared as follows:

A 2.0M solution of 4-fluorobenzyl zinc bromide in tetrahydrofuran (95 ml, 190 mmol; Negishi, E-i. and King, A. O., J.O.C.1977,42,1821) was added dropwise over 20 minutes to a stirred solution of dimethyl 4-bromoisophthalate (20.0 g, 73.2 mmol) and tris(dibenzylideneacetone) dipalladium (0) (0.67 g, 0.73 mmol) in tetrahydrofuran (270 ml) at ambient temperature under an inert atmosphere. During the addition the internal temperature rose to 40° C. The reaction mixture was stirred for 3 hours and then poured into 2M. HCl (1500 ml) cooled in an ice bath and the product extracted into ethyl acetate (3×700 ml). The extracts were washed with water (500 ml), brine (500 ml), dried, and the solvent evaporated under reduced pressure. The residue was taken up in a small quantity of dichloromethane, isohexane added, and the solid, which crystallised from the solution, filtered and dried to give methyl 4-(4-fluorobenzyl)-3-methoxycarbonylbenzoate (10.5 g)

NMR data (CDCl$_3$) δ: 3.87 (3H, s), 3.95 (3H, s), 4.40 (2H, s), 6.93–7.00 (2H, m), 7.06–7.15 (2H, m), 7.29 (1H, d), 8.07 (1H, dd), 8.58 (1H, d). MS m/e 303 (M+H)$^+$.

Methyl 4-(4-fluorobenzyl)-3-methoxycarbonylbenzoate (16.9 g, 56.0 mmol) in methanol (270 ml) was warmed slightly to achieve solution. 2.5M Sodium hydroxide (27 ml, 67.5 mmol) was added and the reaction mixture stirred at ambient temperature for 5 hours. The reaction mixture was poured into water (1200 ml), acidified with concentrated HCl and the product extracted into dichloromethane (3×400 ml). The combined extracts were washed with brine, dried and the solvent evaporated under reduced pressure to give a mixture of 4-(4-fluorobenzyl)-3-methoxycarbonylbenzoic acid and the isomeric monoester, as a cream solid (15.8 g).

NMR data (CDCl$_3$) δ: 3.85–3.98 (3H, m), 4.40–4.52 (2H, m), 6.94–7.02 (2H, m), 7.07–7.17(2H, m), 7.32–7.38 (1H, m), 8.15–8.19 (1H, m), 8.63–8.75 (1H, m); MS m/e 287 (M–H)$^-$.

A 1.0M solution of borane in tetrahydrofuran (100 ml, 100 mmol) was slowly added to a stirred solution of the monoester mixture (15.8 g, 54.7 mmol) at ambient temperature under an inert atmosphere. After the addition the reaction mixture was refluxed for 2 hours, cooled to ambient temperature and methanol (100 ml) added. The solvent was evaporated under reduced pressure and the product purified by column chromatography eluting with ethyl acetate/isohexane (35:65 and 40:60) to give methyl 5-hydroxymethyl-2-(4-fluorobenzyl)benzoate as a light yellow oil (9.3 g).

NMR data (CDCl$_3$) δ: 1.82 (1H, t), 3.82 (3H, s), 4.35 (2H, s); 4.68–4.74 (2H, m), 6.90–6.99 (2H, m), 7.05–7.13 (2H, m), 7.21 (1H, d), 7.46 (1H, dd), 7.90 (1H, d); MS m/e 275 (M+H)$^+$.

Triphenylphosphine (9.7 g., 37.0 mmol) and then carbon tetrabromide (12.3 g., 37.0 mmol) were added to a stirred solution of methyl 5-hydroxymethyl-2-(4-fluorobenzyl) benzoate (4.6 g., 16.8 mmol) in anhydrous ether (150 ml) at ambient temperature. After 4 hours the reaction was filtered and the filtrate concentrated under reduced pressure. The product was purified by column chromatography eluting with ethyl acetate/isohexane (5:95) to give methyl 5-bromomethyl-2-(4fluorobenzyl)benzoate as a colourless oil (5.05 g). NMR data (CDCl$_3$) δ: 3.83 (3H, s), 4.37 (2H, s), 4.50 (2H, s), 6.92–6.99 (2H, m), 7.06 7.13 (2H, m), 7.19 (1H, d). 7.43 (1H, dd), 7.95 (1H, d).

EXAMPLE 9

(2S)-2-{2-(4-fluorobenzyl)-5-[1-(4-fluorophenyl)-2-(imidazol-1-yl)ethoxymethyl]benzoylamino}-4methylsulfanylbutyric acid The title compound was prepared by a similar method to that used for Example 2.

Yield: 77%; $^1$H NMR (DMSO d$_6$+CF$_3$COOD, 400 MHz) δ: 1.9–2.15 (2H, m); 2.04 (3H, s); 2.4–2.7 (2H, m); 4–4.75 (7H, m); 4.9 (1H, m); 7–7.7 (13H, m); 9.02 (1H, s). Anal. Calculated for C$_{31}$H$_{31}$F$_2$N$_3$O$_4$S, 1.5 H$_2$O; C, 61.37; H, 5.65; N, 6.93; S, 5.29; Found: C, 61.31; H, 5.72; N, 7.17; S, 5.09; MS (ESI) m/z 580 (MH$^+$).

EXAMPLE 10

Methyl (2S)-2-{2-phenyl-4-[1-(4fluorophenyl)-2-(imidazol-1-yl)ethoxymethyl]benzoylamino}-4-methylsulfanylbutyrate The title compound was prepared by a similar method to that used for Example 1, but using methyl 4-bromomethyl-2-phenylbenzoate in place of methyl 4-bromomethyl-2-(4-fluorophenyl)benzoate.

Yield: 81%; $^1$H NMR (DMSO d$_6$+CF$_3$COOD, 400 MHz) δ: 1.75–2 (2H, m); 2 (3H, s); 2.15–2.30 (2H, m); 3.64 (3H, s,); 4.30–4.60 (5H, m); 4.94 (1H, m); 7.1–7.8 (14H, m); 9.03 (1H, s). Anal. Calculated for C$_{31}$H$_{32}$FN$_3$O$_4$S, 5.1 H$_2$O; C, 62.25; H, 5.56; N, 7.03; S, 5.36; Found: C, 61.90; H, 5.67; N, 7.05; S, 5.211; MS (ES}) m/z 562 (MH$^+$).

The starting material was prepared by a similar method to that used for 4-bromomethyl-2-(4-fluorophenyl)benzoate in Example 1.

EXAMPLE 11

(2S)-2-{2-phenyl-4-[1-(4-fluorophenyl)-2-(imidazol-1-yl)ethoxymethyl]benzoylamino}-4-methylsulfanylbutyric acid The title compound was prepared by a similar method to that used for Example 2.

Yield: 90%; $^1$H NMR (DMSO d$_6$+CF$_3$COOD, 400 MHz) δ: 1.8–2 (2H, m); 2 (3H, s); 2.1–2.35 (2H, m); 4.25–4.60 (5H, m); 4.9 (1H, m); 7.1–7.8 (14H, m); 9.07 (1H, s). Anal. Calculated for C$_{30}$H$_{30}$FN$_3$O$_9$S, 0.12 H$_2$O; C, 65.54; H, 5.54; N, 7.64; S, 5.83; Found: C, 65.13; H, 5.47; N, 7.71; S, 5.86; MS (ESI) m/z 548 (MH$^+$).

EXAMPLE 12

Methyl (2S)-2-{2-(4-fluorophenyl)-4-[1-(4-fluorophenyl)-2-(imidazol-1-yl)ethoxymethyl]benzoylamino}-4-methylsulfonylbutyrate A solution of methyl (2S)-2-{2-(4-fluorophenyl)-4-[1-(4-fluorophenyl)-2-(imidazol-1-yl)ethoxymethyl]benzoylamino}-4-methylsulfanylbutyrate (compound of Example 1) (0.604 g; 1.04 mmol) and 70% MCPBA (0.650 g; 2.6 mmol) in dichloromethane (15 ml) was stirred at ambient temperature for 5 hours. The solution was washed with saturated sodium bicarbonate and saturated sodium chloride solution and evaporated to dryness. The residue was purified on reverse phase silica eluting with a gradient of 60–70% methanol/ammonium carbonate buffer (2 g/l ; pH7). The appropriate fractions were concentrated and freeze-dried to give the title compound.

Yield: 63%.

The hydrochloride salt was prepared by addition of 3.86N HCl in ether (180 µl) to a solution of the above compound (0.32 g; 0.52 mmol) in dichloromethane (3 ml). The mixture was diluted with ether (100 ml) and the resulting precipitate was filtered and dried.

$^1$H NMR (DMSOd$_6$+CF$_3$COOD, 400 MHz) δ: 2–2.3 (2H, m); 2.9–3.2 (2H, m); 3.02 (3H, s); 3.72 (3H, s); 4.4–4.7 (5H, m); 5 (1H, m); 7.15–7.85 (13H, m); 8.85 (1H, d); 9.15 (1H, s). Anal. Calculated for C$_{31}$H$_{31}$F$_2$N$_3$O$_6$S, 0.9 HCl, 0.6 H$_2$O; C, 56.82; H, 5.09; N, 6.41; S, 4.99; Cl, 4.87; Found: C, 57.27; H, 5.55; N, 6.03; S, 4.57; Cl, 5.07; MS (ESI) m/z: 612 (MH$^+$).

EXAMPLE 13

(2S)-2-{2-(4-Fluorophenyl)-4-[1-(4-fluorophenyl)-2-(imidazol-1-yl)ethoxymethyl]benzoylamino}-4-methylsulfonylbutyric acid The title compound was prepared from Example 12 by a similar method to that used for Example 2.

Yield: 84%; $^1$H NMR (DMSOd$_6$+CF$_3$COOD, 400 MHz) δ: 1.9–2.3 (2H, m); 2.8–3.2 (2H, m); 2.96 (3H, s); 4.3–4.6

(5H, m); 4.96 (1H, m); 7.1–7.8 (13H, m); 8.8 (1H, d); 9.08 (1H, s). Anal. Calculated for $C_{30}H_{29}F_2N_3O_6S$, 1.2 $H_2O$; C, 58.19; H, 5.11; N, 6.79; S, 5.18; Found: C, 58.22; H, 5.24; N, 6.78; S, 4.93; MS (ESI) m/z: 598 ($MH^+$).

EXAMPLE 14 tert-Butyl (2S)-2-{2-(4-fluorophenyl)-4-[1-(4-fluorophenyl)-2-(imidazol-1-yl)ethoxymethyl] benzoylamino}-4-methylsulfonylbutyrate The title compound was prepared from Example 3 by a similar method to that used for Example 12.

Yield: 67%; $^1H$ NMR ($CDCl_3 + CD_3COOD$, 400 MHz) δ: 1.43 (9H, s). 2–2.4 (2H, m); 2.7–3 (2H, m); 2.90 (3H, s); 4.2–4.8 (6H, m); 6.95–7.4 (12H, m); 7.56 (1H, m); 8.34 (1H, s). Anal. Calculated for $C_{34}H_{37}F_2N_3O_6S$; C, 62.47; H, 5.7; N, 6.43; S, 4.9; Found: C, 62.31; H, 6.13; N, 6.26; S, 4.46; MS (ESI) m/z: 654 ($MH^+$).

EXAMPLE 15

N-Methylpiperidin-4-yl (2S)-2-{2-(4-fluorophenyl)-4-[1-(4-fluorophenyl)-2-(imidazol-1-yl) ethoxymethyl]benzoylamino}-4-methylsulfanylbutyrate The title compound was prepared from 2-(4-fluorophenyl)-4-[1-(4-fluorophenyl)-2-(imidazol-1-yl) ethoxymethyl]benzoic acid by a similar method to that used for Example 1 but using N-methylpiperidin-4-yl (2S)-2-amino-4-(methylsulfanyl)butanoate (L-methionine (N-methylpiperidin-4-yl)ester) in place of L-methionine methyl ester.

Yield: 72.5%; $^1H$ NMR ($CDCl_3$, 400 MHz) δ: 1.6–2.1 (6H, m); 2.03 (3H, s); 2.1–2.70 (6H, m); 2.27 (3H, s); 4.05–4.30 (3H, m); 4.45–4.80 (4H, m); 6.05 (1H, m); 6.8–7.6 (14H, m). Anal. Calculated for C, 65.24; H, 6.08; N, 8.45; S, 4.84; Found: C, 64.89; H, 6.33; N, 8.38; S, 4.54; MS (ESI) m/z: 663 ($MH^+$).

EXAMPLE 16

Tert-butyl (2S)-2-{2-(4-fluorophenyl)-4-[1-(thiazol-2-yl)-2-(imidazol-1-yl)ethoxymethyl] benzoylamino}-4-methylsulfanylbutyrate The title compound was prepared from 2-(4-fluorophenyl)4-[1-(thiazol-2-yl)-2-(imidazol-1-yl) ethoxymethyl]benzoic acid by a similar method to that used for Example 1 but using L-methionine tert-butyl ester in place of L-methionine methyl ester.

Yield: 63%; MP: 50–53° C.; $^1H$ NMR ($CDCl_3$, 400 MHz) δ: 1.42 (9H, s); 1.7–2.3 (4H, m); 2.04 (3H, s); 4.2–4.75 (5H, m); 5.01 (1H, m); 6.18 (1H, m); 6.9–7.5 (10H, m); 7.60 (1H, m); 7.82 (1H, m). Anal. Calculated for $C_{31}H_{35}FN_4O_4S_2$; C, 60.96; H, 5.78; N, 9.17; S, 10.50; Found: C, 60.57; H, 5.89; N, 9.41; S, 9.88; MS (ESI) m/z: 611 ($MH^+$).

EXAMPLE 17

Tert-butyl (2S)-2-{2-(4-fluorophenyl)-4-[1-(thiazol-2-yl)-2-(imidazol-1-yl)ethoxymethyl] benzoylaminol}-4-methylsulfonylbutyrate The title compound was prepared from 2-(4-fluorophenyl)-4-[1-(thiazol-2-yl)-2-(imidazol-1-(imidazol-1-yl)ethoxymethyl]benzoic acid by a similar method to that used for Example 1 but using the appropriate sulphonyl compound in place of the L-methionine methyl ester.

Yield: 76%; MP: 90–100° C.; $^1H$ NMR ($CDCl_3$, 400 MHz) δ: 1.43 (9H, s); 2–2.4 (2H, m); 2.6–2.9 (2H, m); 2.87 (3H, s); 4.20–4.60 (4H, m); 4.70 (1H, d); 4.99 (1H, m); 6.35 (1H, m); 6.85–7.45 (10H, m); 7.57(1H, m); 7.84 (1H, m). Anal. Calculated for $C_{31}H_{35}FN_4O_6S_2$; C, 57.93; H, 5.49; N, 8.72; S, 9.98; Found: C, 58.05; H, 5.87; N, 8.81; S, 9.92; MS (ESI) m/z: 643 ($MH^+$).

EXAMPLE 18

Methyl (2S)-2-{2-(4-fluorophenyl)-4-[1-(thiazol-2-yl)-2-(imidazol-1-yl)ethoxymethyl]benzoylamino}-4-methylsulfonylbutyrate The title compound was prepared from Example 4 by a similar method to that used for Example 12.

Yield: 71%; $^1H$ NMR ($CDCl_3$, 400 MHz) δ: 2–2.4 (2H, m); 2.7–3 (2H, m); 2.87 (3H, s); 3.71 (3H, s); 4.20–4.80 (5H, m); 5 (1H,m); 6.5 (1H, m); 6.93 (1H, d); 7.1–7.4 (9H, m); 7.56 (1H, m); 7.84 (1H, m). Anal. Calculated for $C_{28}H_{29}FN_4O_6S_2$, 0.4 $H_2O$; C, 55.32; H, 4.94; N, 9.22; S, 10.55; Found: C, 55.07; H, 5.11; N, 8.88; S, 10.24; MS (ESI) m/z: 601 ($MH^+$).

EXAMPLE 19

(2S)-2-{2-(4-Fluorophenyl)-4-[1-(thiazol-2-yl)-2-(imidazol-1-yl)ethoxymethyl]benzoylamino}-4-methylsulfonylbutyric acid The title compound was prepared from Example 18 by a similar method to that used for Example 2, but heating at ambient temperature for 1 hour instead of at 60° C. for 4 hours.

Yield: 85%; $^1H$ NMR ($DMSOd_6 + CF_3COOD$, 400 MHz) δ: 1.95–2.3 (2H, m); 2.85–3.15 (2H, m); 2.96 (3H, s); 4.35 (1H, m); 4.6–4.90 (4H, m); 5.40 (1H, m); 7.15–8 (11H, m); 9.11 (1H, s). Anal. Calculated for $C_{27}H_{27}FN_4O_6S_2$, 2 $H_2O$, 0.7 $CH_3COONH_4$; C, 50.41; H, 5.35; N, 9.73; S, 9.48; C, 50.74; H, 5.32; N, 9.37; S, 9.18; MS (ESI) m/z: 587 ($MH^+$).

EXAMPLE 20

N-Methylpiperidin-4-yl (2S)-2-{2-(4-fluorophenyl)-4-[1-(thiazol-2-yl)-2-(imidazol-1-yl)ethoxymethyl] benzoylamino}-4-methylsulfanylbutyrate The title compound was prepared by a similar method to that used for Example 1 but using L-methionine (N-methylpiperidin4-yl) ester in place of L-methionine methyl ester.

Yield: 50%; $^1HNMR$ $CDCl_3$, 400 MHz) δ: 1.65–2.1 (6H, m); 2.03 (3H, s); 2.1–2.7 (6H, m); 2.17 (3H, s); 4.25–4.80 (6H, m); 5.01 (1H, m); 6.25 (1H, m); 6.85–7.4 (10H, m); 7.6 (1H, m); 7.81 (1H, m). Anal. Calculated for $C_{33}H_{38}FN_5O_4S_2$, 0.7 $H_2O$; C, 59.65; H, 5.98; N, 10.54; S, 9.65; Found: C, 59.72; H, 5.90; N, 10.37; S, 9.16; MS (ESI) m/z: 652 ($MH^+$).

EXAMPLE 21 tert-Butyl (2S)-2-{2-(4-fluorophenethyl)-4-[1-(4-fluorophenyl)-2-(imidazol-1-yl)ethoxymethyl] benzoylamino}-4-methylsulfonylbutyrate The title compound was prepared from 2-(4-fluorophenethyl)-4-[1-(4-fluorophenyl)-2-(imidazol-1-yl) ethoxymethyl]benzoic acid by a similar method to that used for Example 1 using the appropriate sulphonyl tert-butyl ester (tert-butyl (2S)-2-amino-4-(methylsulfonyl)butanoate) in place of the L-methionine methyl ester.

Yield: 30%; $^1$H NMR (DMSOd$_6$, 400 MHz) δ: 1.40 (9H, s); 2.1–2.4 (2H, m); 2.7–3.05 (4H, m); 3.08 (3H, s); 3.3–3.4 (2H, m); 4.20–4.50 (5H, m); 6.85 (1H, s); 7–7.55 (14H, m); 8.75 (1H, m). Anal. Calculated for $C_{36}H_{41}F_2N_3O_6S$, 0.3 $H_2O$; C, 62.92; H, 6.10; N, 6.11; S, 4.67; Found: C, 62.57; H, 6.26; N, 6.06; S, 4.33; MS (ESI) m/z: 682 (MH$^+$).

EXAMPLE 22

Tert-butyl (2S)-2-{2-(4-fluorophenethyl)-4-[1-(4-fluorophenyl)-2-(imidazol-1-yl)ethoxymethyl]benzoylamino}-4-methylsulfanylbutyrate The title compound was prepared from 2-(4-fluorophenethyl)-4-[1-(4-fluorophenyl)-2-(imidazol-1-yl)ethoxymethyl]benzoic acid by a similar method to that used for Example 3.

Yield:31%; $^1$H NMR (CDCl$_3$, 400 MHz) δ: 1.50 (9H, s); 2.10 (3H, s); 2.05–2.35 (2H, m); 2.64 (2H, m); 2.85–3.15 (4H, m); 4–4.15 (3H, m); 4.4–4.55 (2H, m); 4.80 (1H, m); 6.8–7.45 (14H,). Anal. Calculated for $C_{36}H_{41}F_2N_3O_4S$, 0.3 $H_2O$; C, 65.99; H, 6.40; N, 6.41; S, 4.89; Found: C, 65.99; H, 6.78; N, 6.41; S, 4.55; MS (ESI) m/z: 650 (MH$^+$).

EXAMPLE 23

(2S)-2-{2-(4-Fluorophenethyl)-4-[1-(4-fluorophenyl)-2-(imidazol-1-yl)ethoxymethyl]benzoylamino}-4-methylsulfonylbutyric acid A solution of Example 21 (0.1 g; 0.15 mmol) in solution in dichloromethane (0.5 ml) and TFA (1 ml) was stirred at ambient temperature for 2 hours. After evaporation to dryness, the residue was puified on reverse phase silica eluting with a gradient of 50–60% methanol/ammonium carbonate buffer (2 g/l, pH 7). The appropriate fractions were concentrated and freeze dried to give the title compound.

Yield: 45%; $^1$H NMR (DMSOd$_6$+CF$_3$COOD, 400 MHz) δ: 2.1–2.4 (2H, m); 2.75–3.1 (2H, m); 2.99 (3H, s); 3.1–3.4 (4H, m); 4.25–4.60 (5H, m); 4.90 (1H, m); 7–7.75 (13 H, m); 9.03 (1H, s). Anal. Calculated for $C_{32}H_{33}F_2N_3O_6S$, 2 $H_2O$; C, 58.08; H, 5.64; N, 6.35; S, 4.85; Found: C, 57.88; H, 5.30; N, 6.27; S, 4.97; MS (ESI) m/z: 626 (MH$^+$).

EXAMPLE 24

Tert-butyl (2S)-2-{2-(4-fluorophenyl)-4-[1-(4-fluorophenyl)-2-(2-hydroymethylimidazol-1-yl)ethoxymethyl]benzoylamino}-4-methylsulfanylbutyrate The title compound was prepared by a similar method to that used for Example 1 but using L-methionine-t-butyl ester in place of L-methionine methyl ester.

Yield: 60%; $^1$HNMR (DMSO, 400 MHz) δ: 1.40 (9H, s); 1.7–2.3 (4H, m); 1.99 (3H, s); 4.15–4.50 (7H, m); 4.85 (1H, m); 5.26 (1H, m); 6.74 (1H, m); 7.05–7.5 (12H, m); 8.52 (1H, d). Anal. Calculated for $C_{35}H_{39}F_2N_3O_5S$; C, 64.5; H, 6.03; N, 6.45; S, 4.92; Found: C, 64.74; H, 6.05; N, 6.23; S, 4.57; MS (ESI): 652 (MH$^+$).

The starting material was prepared as follows:

A solution of 2-hydroxymethylimidazole (1.96 g ; 0.02 mole), imidazole (3.4 g; 0.05 mole), tert-butyldiphenylsilyl chloride (6.6 g; 0.024 mole) in DMF (20 ml) was stirred under an argon atmosphere for 16 hours. The mixture was extracted with ethyl acetate and purified by flash column chromatography eluting with a gradient 50–70% ethyl acetate/petroleum ether to give 2-(tert-butyldiphenylsilyloxymethyl)imidazole as a solid.

Yield: 82% $^1$H NMR (CDCl$_3$, 400 MHz) δ: 1.1 (9H, s); 4.85 (2H, s); 6.99 (2H, s); 7.3–7.5 (6H, m); 7.65 (4H, m).

A solution of 2-(tert-butyldiphenylsilyloxymethyl)imidazole (3.37 g; 0.01 mol), bromomethyl acetone (2.17 g; 0.01 mole) and TEA (1.67 ml; 0.012 mole) in ethyl acetate (40 ml) was heated at reflux under argon atmosphere for 6 hours. After filtration of the insoluble material and evaporation to dryness, the residue was purified by flash column chromatography eluting with ethyl acetate/petroleum ether (50:50) to give 1-(4-fluorobenzoylmethyl)-2-(tert-butyldiphenylsilyloxymethyl)imidazole.

Yield: 71% $^1$H NMR (CDCl$_3$, 400 MHz) δ: 0.96 (9H, s); 7.78 (2H, s); 5.53 (2H, s); 6.8–7.6 (14H, m); 7.95 (2H, m).

Sodium borohydride (0.41 g; 1.06 mmol) was added portionwise at 0° C. to a solution of 1-(4-fluorobenzoylmethyl)-2-(tert-butyldiphenylsilyloxymethyl)imidazole (4.81 g; 1.01 mmol) in methanol (100 ml). The mixture was stirred at ambient temperature for 16 hours. 12N HCl (0.84 ml) added and then evaporated to dryness and purified by flash column chromatography eluting with dichloromethane/ethanol (96:4) to give 1-[2-(4-fluorophenyl)-2-hydroxyethyl]-2-(tert-butyldiphenylsilyloxymethyl)imidazole.

Yield: 63% $^1$H NMR (CDCl$_3$, 400 MHz) δ: 1.10 (9H, s); 4.19 (2H, m); 4.61 (2H, s); 4.95 (1H, m); 6.8–7.8 (16H, m).

Methyl 2-(4-fluorophenyl)-4-{1-(4-fluorophenyl)-2-[2-(tert-butyldiphenylsilyloxymethyl)imidazol-1-yl]ethoxymethyl}benzoate was prepared by a similar method to that used for Example 1 but using 1-[2-(4-fluorophenyl)-2-hydroxyethyl]-2-(tert-butyldiphenylsilyloxymethyl)imidazole in place of 1-(4-fluorophenyl)-2-(imidazol-1-yl)ethanol.

Yield: 90% $^1$H NMR (CDCl$_3$, 400 MHz) δ: 1.01 (9H, s); 3.65 (3H, s); 4.1–4.45 (4H, m); 4.60 (3H, m); 6.90–7.8 (23H, m).

Methyl 2-(4-fluorophenyl)4-{1-(4-fluorophenyl)-2-[2-(tert-butyldiphenylsilyloxymethyl)imidazol-1-yl]ethoxymethyl}benzoate (4 g; 5.58 mmol) in methanol (50 ml) was treated with 2N aqueous sodium hydroxyde solution (5 ml; 11.1 mmol) at 80° C. for 7 hours. After evaporation of the methanol, the residue was taken up in water, the pH adjusted to with 6N HCl and extracted with dichloromethane/ethanol (95/5) to give 2-(4-fluorophenyl)-4-[1-(4-fluorophenyl)-2-(2-hydroxymethylimidazol-1-yl)ethoxymethyl]benzoic acid.

Yield: 83% NMR (DMSO+CF$_3$COOD) δ: 4.2–4.4 (4H, m); 4.5–5 (3H, m); 7–7.7 (13 H, m).

EXAMPLE 25

Methyl (2S)-2-{2-(4-fluorophenyl)-4-[1-(4-fluorophenyl)-2-(2-hydroxymethylimidazol-1-yl)ethoxymethyl]benzoylamino}-4-methylsulfanylbutyrate The title compound was prepared from 2-(4-fluorophenyl)-4-[1-(4-fluorophenyl)-2-(2-hydroxymethylimidazol-1-yl)ethoxymethyl]benzoic acid by a similar method to that used for Example 1.

Yield: 60% $^1$H NMR (CDCl$_3$, 400 MHz) δ: 1.7–2.3 (4H, m); 2.02 (3H, s); 3.68 (3H, s); 4.1–4.30 (3H, m); 4.45–4.8 (5H, m); 6.1–6.2 (1H, m); 6.84 (2H, m); 7.05–7.20 (6H, m);

7.22–7.4 (4H, m); 7.57 (1H, m). Anal. Calculated for $C_{32}H_{33}F_2N_3O_5S$; C, 63.04; H, 5.46; N, 6.89; S 5.26; Found: C, 63.40; H, 5.64; N, 6.64; S, 4.84; MS (ESI) m/z: 610 (MH$^+$).

EXAMPLE 26

(2S)-2-{2-(4-Fluorophenyl)-4-[1-(4-fluorophenyl)-2-(2-hydroxymethylimidazol-1-yl)ethoxymethyl]benzolamino}-4-methylsulfanylbutyric acid The title compound was prepared from Example 25 by a similar method to that used for Example 2.

Yield: 80% $^1$H NMR (CDCl$_3$+CF$_3$COOD, 400 MHz) δ: 1.8–2.5 (4H, m); 2.06 (3H, s); 4.2–4.4 (3H, m); 4.5–5 (5H, m); 7–7.4 (12H, m); 7.6 (1H, m). Anal. Calculated for $C_{31}H_{31}F_2N_3O_5S$, 0.5 H$_2$O; C, 61.58; H, 5.33; N, 6.95; S, 5.30; Found: C, 61.63; H, 5.55; N, 6.85; S, 4.91; MS (ESI) m/z: 596 (MH$^+$).

EXAMPLE 27

Tert-butyl (2S)-2-{2-(4-fluorophenyl)-4-[1-(4-fluorophenyl)-2-(2-hydroxymethylimidazol-1-yl)ethoxymethyl]benzoylaminol}-4-methylsulfonylbutyrate The title compound was prepared from 2-(4-fluoropbenyl)-4-[1-(4-fluorophenyl)-2-(2-hydroxymethylimidazol-1-yl)ethoxymethyl]benzoic acid and the appropriate tert-butyl ester by a similar method to that used for Example 1.

Yield: 42% $^1$H NMR (CDCl$_3$): 1.43 (9H, s); 1.9–2.4 (2H, m); 2.6–2.95 (2H, m); 2.86 (3H, s); 4.1–4.3 (3H, m); 4.4–54.7 (5H, m); 6.15–6.25 (1H, m); 6.85 (2H, m); 7.05–7.4 (10H, m); 7.55 (1H, m). Anal. Calculated for $C_{35}H_{39}F_2N_3O_7S$; C, 61.48; H, 5.75; N, 6.15; S, 4.69; Found: C, 60.99; H, 6.09; N, 6.04; S, 4.92; MS (ESI) m/z: 684 (MH$^+$).

EXAMPLE 28

Methyl (2S)-2-{2-(4-fluorophenyl)-4-[1-(4-fluorophenyl)-2-(imidazol-1-yl)ethoxymethyl]benzoalamino}-2-methyl-4-methylsulfanylbutyrate The title compound was prepared by a similar method to that used for Example 1 but using α-methyl-L-methionine methyl ester.

Yield: 60% $^1$H NMR (CDCl$_3$, 400 MHz) δ: 1.47 (3H, s); 1.9–2.6 (4H, m); 2.03 (3H, s); 3.70 (3H, s); 4.05–4.6 (5H, m); 6.34 (1H, s); 6.8–7.6 (14H, m). Anal. Calculated for $C_{32}H_{33}F_2N_3O_4S$, 0.3 H$_2$O C, 64.16; H, 5.65; N, 7.01; S, 5.35; Found: C, 63.95; H, 5.65; N, 6.84; S, 4.80; MS (ESI) m/z: 594 (MH$^+$).

EXAMPLE 29

(2S)-2-{2-(4-Fluorophenyl)-4-[1-(4-fluorophenyl)-2-(imidazol-1-yl)ethoxymethyl]benzoylamino}-2-methyl-4-methylsulfanylbuyric acid The title compound was prepared by a similar method to that used for Example 2.

Yield: 42% $^1$H NMR (CDCl$_3$, 400 MHz) δ: 1.57 (3H, d); 2.02 (3H, d); 2.05–2.3 (2H, m); 2.6–2.8 (2H, m); 4.05–4.25 (3H, m); 4.45–4.65 (2H, m); 6.8–7.35 (12H, m); 7.54 (1H, m); 7.86 (1H, s). Anal. Calculated for $C_{31}H_{31}F_2N_3O_4S$, 0.6 H$_2$O; MS (ESI) m/z: 580 (MH$^+$).

EXAMPLE 30

N-(4-Chlorobenzenesulfanyl)-(2S)-2-{2-(4-fluorophenyl)-4-[1-(4-florophenyl)-2-(imidazol-1-yl)ethoxymethyl]benzoylamino}-4-methylsulfanylbutyramide The title compound was prepared by a similar method to that used for Example 1 but using N-(4chlorobenzenesulfonyl)-(2S)-2-amino-4-methylsulfanylbutyramide.

Yield: 42% $^1$H NMR (CDCl$_3$+CD$_3$COOD, 400 MHz) δ: 1.6–2.2 (4H, m); 1.95 (3H, d); 4.15–4.35 (2H, m); 4.45–4.70 (3H, m); 6.9–7.5 (15H, m); 7.90 (2H, m); 8.42 (1H, d). Anal. Calculated for $C_{36}H_{33}ClF_2N_4O_5S_2$,0.3 H$_2$O; C, 58.04; H, 4.55; N, 7.52; S, 8.61; Found: C, 57.96; H, 4.70; N, 7.40; S, 8.27; MS (ESI) m/z: 739 (MH$^+$).

EXAMPLE 31

2(Morpholinomethyl)prop-2-yl (2S)-2-{2-(4-fluorophenethyl)-5-[1-(4-florophenyl)-2-(imidazol-1-yl)ethoxymethyl]benzoylamino}-4-metbylsulfanylbutyrate A mixture of 2-(4-fluorophenethyl)-5-[1-(4-fluorophenyl)-2-(imidazol-1-yl)ethoxymethyl]benzoic acid (0.462 g, 1 mmol), EDC (0.211 g, 1.1 mmol), 1-hydroxy-7-azabenzotriazole (0.148 g, 1.1 mmol), DMAP (0.122 g, 1 mmol) and 2-(morpbolinomethyl)prop-2-yl (2S)-2-amino-4-methylsulfanylbutyrate (0.29 g, 1 mmol) in dichloromethane (10 ml) was stirted at ambient temperature for 16 hours. The mixture was extracted with dichloromethane, evaporated to dryness and purified by flash column chromatography eluting with dichloromethane/ethanol (97:3) to give the title compound.

Yield: 60% $^1$H NMR (CDCl$_3$, 400 MHz) δ: 1.52 (6H,m); 2–2.34 (2H, m); 2.11(3H, m); 2.51–2.79 (8H, m); 2.80–3.14 (4H, m); 3.67 (4H, m); 3.98–4.17 (3H, m); 4.4–4.53 (2H, m); 4.77 (1H, m); 6.81–7.48 (14H, m). Anal. Calculated for $C_{40}H_{48}F_2N_4O_5S$ C, 65.37; H, 6.58; N, 7.60; S, 4.36; Found: C, 65.20; H, 6.96; N, 7.77; S, 4.69; MS (ESI) m/z: 735 (MH$^+$).

The starting material 2-(morpholinomethyl)prop-2-yl (2S)-2-amino-4-methylsulfanylbutyrate was prepared as follows.

A solution of N-(2-oxopropyl)morpholine (82 g, 0.57 mmol) in diethyl ether (400 ml) was added to a solution of 3M CH$_3$MgBr (500 ml, 1.5 ml) in anhydrous diethyl ether (21) and stirred at 0° C. under an argon atmosphere. The mixture was stirred at ambient temperature for 16 hours, treated with 12N HCl (50 ml) and extracted with ethyl acetate. The product was purified by flash column chromatography eluting with ethyl acetate to give N-(2-hydroxy-2-methylpropyl)morpholine.

Yield: 33% $^1$H NMR (CDCl$_3$, 400 MHz) δ: 1.05–1.4 (6H, m); 2.32 (2H, s); 2.55–2.72 (4H, m); 2.98 (1H, br); 3.6–3.82 (4H, m).

A solution of N-(2-hydroxy-2-methylpropyl)morpholine (9.8 g, 62 mmol), N-benzyloxycarbonyl-L-methionine (12.6 g, 44 mmol), bromo-tris-pyrrolidino-phosphonium hexafluorophosphate (25 g, 54 mmol), DMAP (5.4 g, 44 mmole) in dichloromethane (250 ml) was stirred, in the presence of 4 Å molecular sieves (5 g), at ambient temperature for 48 h. After evaporation to dryness, the mixture was taken up in diethyl ether and the insoluble material eliminated by filtration. The organic layer was washed with a saturated aqueous solution of sodium hydrogen carbonate and a saturated solution of brine, evaporated to dryness and purified by flash column chromatography eluting with dichloromethane/ethanol (98:2) to give 2-(morpholinomethyl)prop-2-yl (2S)-2-(benzyloxycarbonylamino)-4-methylsulfanylbutyrate (40%).

$^1$H NMR (CDCl$_3$, 400 MHz) δ: 1.51 (6H, m); 1.85–2.27 (2H, m); 2.09 (3H, s); 2.45–2.70 (8H, m); 3.66 (4H, m); 4.36 (1H, m); 5.10 (2H, m); 5.25–5.40 (1H, m); 7.3–7.5 (5H, m).

A solution of HCO$_2$NH$_4$ (5.6 g, 88.5 mmol) in water (10 ml) was added dropwise to a suspension of compound 2-(morpholinomethyl)prop-2-yl (2S)-2-(benzyloxycarbonylamino)-4-methylsulfanylbutyrate (7.5 g, 17.7 mmol) and 10% palladium on carbon (7.5g) in DMP (80 ml). The mixture was stirred at ambient temperature for 18 h. After filtration through Celite, the titrate was evaporated to dryness, neutralised with ammonia in diethyl ether to pH 9 and extracted with more ether. After evaporation the compound was purified by flash column chromatography eluting with a gradient of 1–5% ethanol/dichloromethane to give 2-(morpholinomethyl)prop-2-yl (2S)-2-amino-4-methylsulfanylbutyrate (50%).

$^1$H NMR (CDCl$_3$, 400 MHz) δ: 1.51 (6H, m); 1.6–2.08 (2H, m); 2.12 (3H, s); 2.50–2.80 (8H, m); 3.47 (1H, m); 3.62–3.77 (4H, m).

EXAMPLE 32

Methyl (2S)-2-{4-[1-(4-fluorophenyl)-2-(imidazol-1-yl)ethoxy]-2-(4-fluorophenyl)benzoylamino}-4-methylsulfanylbultyrate ADDP (0.404 mg; 1.53 mmol) was added to a solution of 1-(4-fluorophenyl)-2-(imidazol-1-yl) ethanol (0.3 g; 1.45 mmol), methyl (2S)-2-[2-(4-fluorophenyl)-4-hydroxybenzoylamino]-4-methylsulfanylbutyrate (0.49 g; 1.45 mmol) and triphenylphosphine (0.4 g; 1.52 mmol) in THF (8 ml). The mixture was stirred for 16 hours at ambient temperature. After evaporation to dryness, the residue was purified by flash column chromatography eluting with a gradient of 1–20% ethanol/dichloromethane. The product was further purified on reverse phase silica eluting with 60% methanol/ammonium carbonate buffer (2 g/l, pH 7). The appropriate fractions were evaporated, redissolved in dichloromethane (2 ml), treated at 0° C. with a 3.8 N HCl solution in diethyl ether, diluted with diethyl ether (100 ml) to precipitate the hydrochloride salt which was filtered and dried to give the title compound (25%).

$^1$H NMR (CDCl$_3$, 400 MHz) δ: 1.7–2.1 (2H, m); 2 (3H, s); 2.1–2.25 (2H, m); 3.65 (3H, s); 4.35 (2H, m); 4.60(1H, m); 5.36 (1H, m); 5.82 (1H, d); 6.7–7.5 (14H, m). MS (ESI) m/z 566 (MH$^+$).

The starting material was prepared as follows:

Triethylamine (29 ml; 0.206 mol) was added to a solution of methyl 4-methoxysalicylate (25.0 g; 0.137 mol) in dichloromethane (500 ml) and the solution cooled to 0° C. Trifluoromethanesulphonic anhydride (29 ml; 0.172 mol) was added dropwise and the reaction stirred at ambient temperature for 1 hour. Additional portions of triethylamine and triflic anhydride were added over 16 hours until HPLC showed absence of starting material. The reaction was washed with 2N HCl and the organic phase evaporated to give a brown oil. Purification by flash column chromatography eluting with ethyl acetate/iso-hexane (1:1) gave methyl 4-methoxy-2-trifluoromethylsulfonyloxybenzoate as a pale yellow oil (23.4 g).

Yield: 76% $^1$H NMR (CDCl$_3$, 300 MHz) δ: 3.88 (3H, s); 3.93 (3H, s); 6.79 (1H, d); 6.96 (1H, dd); 8.06(1H, d). MS (ESI) m/z 315(MH$^+$).

Saturated aqueous sodium hydrogen carbonate solution (50 ml) was added to a solution of methyl 4-methoxy-2-trifluoromethylsulfonyloxybenzoate (6.3 g; 0.02 mol) and 4-fluorobenzeneboronic acid (3.36 g; 0.024 mol) in DME (150 ml) at ambient temperature under an argon atmosphere. Tetrakis(triphenylphosphine) palladium (928 mg; 0.8 mmol) was then added and the reaction heated at reflux for 3.5 hours to give a homogeneous solution. After cooling to ambient temperature, the reaction was partitioned between ethyl acetate and water. The organic phase was washed with 2N HCl, water and brine, filtered through 1PS filter paper and the solvent removed in vacuo to give methyl 4-methoxy-2-(4-fluorophenyl)benzoate as a yellow oily solid (7.2 g) which was used without further purification.

$^1$H NMR (CDCl$_3$, 300 MHz) δ: 3.65 (3H, s); 3.87 (3H, s); 6.79 (1H, d); 6.91 (1H, dd); 7.08 (2H, dd), 7.25 (2H, dd), 7.90 (1H, d). MS (ESI) m/z 261 (MH$^+$).

To a solution of methyl 4-methoxy-2-(4-fluorophenyl) benzoate (9.8 g; 0.029 mol) in methanol (75 ml) was added 2N aqueous sodium hydroxide solution (45 ml) and the mixture heated at reflux for 1.5 h. The reaction was cooled to ambient temperature, filtered and the filtrate concentrated in vacuo to remove the methanol. The residual aqueous phase was washed with diethyl ether, acidified to pH 1 with concentrated HCl and extracted with ethyl acetate. The organic extracts were dried (MgSO$_4$) and the solvent removed in vacuo to give 4-methoxy-2-(4-fluorophenyl) benzoic acid as a white solid (7.7 g), which was used without further purification.

$^1$H NMR (DMSO d$_6$, 300 MHz) δ: 3.80 (3H, s); 6.80 (1H, d); 6.98 (1H, dd); 7.18 (2H, dd), 7.31 (2H, dd), 7.76 (1H, d). MS (ESI) m/z 247 (MH$^+$).

A solution of boron tribromide (0.066 mol) in dichloromethane (66 ml) was added dropwise to a solution of 4-methoxy-2-(4-fluorophenyl)benzoic acid (7.7 g; 0.029 mol) in dried dichloromethane (215 ml) under argon at 0° C. The reaction was stirred for 1 hour at 0° C. and allowed to warm to ambient temperature and stirred for a further 16 hours. It was then poured into ice water and extracted with firstly dichloromethane then with ethyl acetate. The combined organic extracts were washed with saturated aqueous sodium hydrogen carbonate and the aqueous phase acidified to pH 1 with concentrated HCl and extracted with ethyl acetate. The ethyl acetate extracts were dried (MgSO$_4$) and concentrated in vacuo to give 4-hydroxy-2-(4-fluorophenyl) benzoic acid as a yellow oil (4.5 g), which was used without further purification.

$^1$H NMR (DMSO d$_6$, 300 MHz) δ: 6.63 (1H, d); 6.80 (1H, dd); 7.15 (2H, dd), 7.26 (2H, dd), 7.71 (1H, d). MS (ESI) mn/z 233 (MH$^+$).

To a solution of 4-hydroxy-2-(4-fluorophenyl)benzoic acid (4.5 g; 0.019 mol) in DMF (90 ml) cooled to 0° C. under an argon atmosphere was added in sequence NMM (6.4 ml; 0.058 mol), L-methionine methyl ester hydrochloride (4.0 g; 0.020 mol), EDC (4.47 g; 0.023 mol) and HOBT (2.7 g; 0.020 mol) and the reaction warmed to ambient temperature and stirred for 3 hours. The DMF was removed in vacuo and the residue partitioned between ethyl acetate and water. The organic phase was washed with water and brine, filtered through PSI filter paper and concentrated in vacuo to give a yellow oil. Purification by flash column chromatography eluting with ethyl acetate/iso-hexane (1:1) gave methyl (2S)-2-[4-hydroxy-2-(4-fluorophenyl)benzoylamino]-4-methylsulfanylbutyrate as a white foam (5.7 g).

Yield: 51% (over 4 steps); $^1$H NMR (DMSO d$_6$, 300 MHz) δ: 1.80 (1H, m); 1.95 (1H, m); 2.03 (3H, s), 2.20 (2H, dd); 3.70(3H, s); 4.65 (1H, m); 5.97 (1H, d), 6.70(1H, d); 6.78 (1H, dd); 6.82 (1H, br s); 7.07 (2H, dd), 7.30 (2H, dd), 7.55 (1H, d). Anal. Calculated for C$_{19}$H$_{20}$FNO$_4$S; C, 60.46; H, 5.34; N, 3.71; S, 8.50; F, 5.03; Found: C, 60.1; H, 5.4; N, 3.6; S, 8.3; F, 5.2; MS (ESI) m/z 378 (MH$^+$).

EXAMPLE 33

(2S)-2-{4-[1-(4-Fluorophenyl)-2-(imidazol-1-yl) ethoxy]-2-(4-fluorophenyl)benzoylamino}-4-methylsulfanylbutyric acid A solution of methyl (2S)-2-{4-[1-(4-fluorophenyl)-2-(imidazol-1-yl)ethoxy]-2-(4-fluorophenyl)benzoylamino}-4-methylsulfanylbutyrate (0.037 g; 0.061 mmol) in methanol (3 ml) was treated with 2N aqueous sodium hydroxide solution (0.32 ml) and the mixture stirred at ambient temperature for 2 hours. After evaporation of the methanol, the aqueous residue was acidified to pH 7.5 with 6N HCl and purified on reverse phase silica eluting with a gradient of 50–60% methanol ammonium carbonate buffer (2 g/l, pH 7). The appropriate fractions were concentrated and freeze-dried to give the title compound as a solid.

Yield : 42%; $^1$H NMR (DMSO d$_6$, 400 MHz) δ: 1.7–2 (2H, m); 2 (3H, s); 2.1–2.3 (2H, m); 4.16 (1H, s); 4.42 (2H, m); 5.8 (1H, m); 6.8–7.7 (14H, m); 8.25 (1H, m). Anal. Calculated for C$_{29}$H$_{27}$F$_2$N$_3$O$_4$S, 0.9 H$_2$O; C, 61.34; H, 5.11; N, 7.4; S, 5.65; Found: C, 61.27; H, 4.75; N, 7.20; S, 5.36; MS (ESI) m/z 552 (MH$^+$).

EXAMPLE 34

Methyl (2S)-2-{5-[1-(4-fluorophenyl)-2-(imidazol-1-yl)ethoxy]-2-(4-fluorophenethyl)benzoylamino}-4-methylsulfanylbutyrate A mixture of 5-(1-(4-fluorophenyl)-2-(imidazol-1-yl)ethoxy)-2-(4-fluorophenethyl)benzoic aci d (570 mg,1.27 mmol), L-methionine methyl ester (510 mg, 2.5 mmol), 1-(3-dimethylaminopropyl)-3-ethylcarbodiimide hydrochloride EDC) (370 mg, 1.9 mmol )in dichloromethane (50 ml), was stirred at ambient temperature for 16 hours. It was then washed with aqueous citric acid (2×40 ml, 1 M), brine, dried (MgSO$_4$) and evapourated to dryness and the residue so obtained purified by chromatography on silica (40 gm Dynamax column, gradient elution with 2–6% methanol/dichloromethane). The relevant fractions were combined and evaporated to give 640 mg of a product which was re-dissolved in dichloromethane, washed with aqueous citric acid (4×30 ml, 1M), brine, dried and evaporated to give a residue. This was redissolved in dichloromethane (4 ml) at 0° C., treated with 1MHCl/Et$_2$O (10 ml), stirred for 2 hours, the solution evaporated to dryness and the residue triturated with ether to give the hydrochloride salt of the title compound as a white solid (343 mg). $^1$H NMR (CDCl$_3$ , 300 MHz) δ: 2–2.1 (4H,m); 2.15–2.32 (1H, m); 2.55 (2H,t); 2.72–2.82 (2H,m); 2.84–2.98 (2H, m); 3.78 (3H,d); 4.2–4.4 (2H,m); 4.78–4.86 (1H,m); 5.25 (–5.3 (1H,m); 6.34 (1H,d); 6.7 (1H,dd); 6.8–6.83 (1H,m); 6.84–7.00 (4H,m); 7.0–7.12 (5H,m); 7.2–7.3 (2H,m); 7.44 (1H,s). MS (ES+) m/z 594.3 (MH$^+$); Anal.calculated for C$_{32}$H$_{33}$F$_2$N$_3$O$_4$S.HCl.H$_2$O C, 59.3; H, 5.6; N, 6.5; S, 4.9; Found: C, 59.3; H, 5.5; N, 6.1; S, 5.2%.

EXAMPLE 35

(2S)-2-{5-[1-(4-Fluorophenyl)-2-(imidazol-1-yl) ethoxy]-2-(4-fluorophenethyl)benzoylamino}-4-methylsulfanylbutyric acid A solution of methyl (2S)-2-{5-[1-(4-fluorophenyl)-2-(imidazol-1-yl)ethoxy]-2-(4-fluorophenethyl) benzoylamino}-4-methylsulfanylbutyrate (140 mg, 0.24 mmol) in methanol (5 ml) was treated with sodium hydroxide (190 mg, 4.7 mmol) in water (1 ml) and the mixture stirred at ambient temperature for 6 hours. The mixture was acidified to PH1 with 1M HCl and evaporated to dryness. The residue was washed with water (3×2 mL) and the resulting gum was triturated with diethyl ether to give the title compound as a white solid (43 mg). $^1$H NMR (DMSO-d$_6$, 300 MHz) δ: 1.85–2.05 (5H,m); 2.4–2.6 (signed partially obscured by solvent signals, m); 2.6–2.75 (2H,m); 2.75–2.86 (2H,m); 4.4–4.48 (1H, m); 4.64.7 (2H,m); 5.82 (1H,t); 6.76–6.86 (2H,m); 6.96–7.08 (3H,m); 7.12–7.28 (4H,m); 7.44–7.5 (2H,dd); 7.62 (1H,s); 7.69 (1H,s); 8.58 (1H,t); 9.12 (1H,s). MS (ES+) m/z 580.3 (MH+) Anal.calculated for C$_{31}$H$_{31}$F$_2$N$_3$O$_4$S.HCl.0.9NaCl C, 55.7; H, 4.8; N, 6.3%; Found: C, 55.9; H, 4.8; N, 6.1%.

EXAMPLE 36 tert-Butyl (2S)-2-{5-[1-(4-fluorophenyl)-2-(imidazol-1-yl)ethoxy]-2-(4-fluorophenethyl) benzoylamino}-4-methylsulfanylbutyrate The title compound was prepared in 80% yield from 5-(1-(4-fluorophenyl)-2-(imidazol-1-yl)ethoxy)-2-(4-fluorophenethyl)benzoic acid and L-methionine tert-butyl ester by a similar method to that used for Example 34. $^1$H NMR (DMSO-d$_6$, 300 MHz) δ: 1.38 (9H,s); 1.88–2.0 (2H, m); 2.02 (3H,d); 2.62–2.75 (2H,m); 2.75–2.9 (2H,m); 4.32–4.42 (1H, m); 4.68 (2H,d); 5.83 (1H,m); 6.79–6.83 (2H,md); 6.95–7.1 (3H,m); 7.1–7.28 (4H,m); 7.45–7.52 (2H,dd); 7.61 (1H,s); 7.68 (1H,S); 8.62 (1H,t); 9.08 (1H,s). MS (ES+) m/z 636.4 (MH+); Anal.calculated for C$_{35}$H$_{39}$F$_2$N$_3$O$_4$S.2.7H$_2$O C, 61.4; H, 6.5; N, 6.1%; Found: C, 61.1; H, 6.2; N, 5.7%.

EXAMPLE 37

Cyclopentyl (2S)-2-{5-[1-(4-fluorophenyl)-2-(imidazol-1-yl)ethoxy]-2-(4-fluorophenethyl) benzoylamino}-4-methylsulfanylbutyrate The title compound was prepared in 72% yield from 5-(1-(4-fluorophenyl)-2-(imidazol-1-yl)ethoxy)-2-(4-fluorophenethyl)benzoic acid and cyclopentyl (2S)-2-amino-4-(methylsulfanyl)butanoate (L-methionine cyclopentyl ester) by a similar method to that used for Example 34.

$^1$H NMR (DMSO-d$_6$, 300 MHz) δ: 1.44–1.65 (6H,m); 1.7–1.86 (2H,m); 1.9–2.0 (2H,m); 2.02 (3H,d); 2.5–2.6 (signals partially obscured by solvent signals,m); 2.62–2.9 (4H, m); 4.4–4.5 (1H,dd); 4.65 (2H,d); 5.04–5.1 (1H,m); 5.82 (1H,bds); 6.78–6.84 (2H,m); 6.97–7.1 (3H,dd); 7.12–7.3 (4H,m); 7.42–7.5 (2H,m); 7.58 (1H,bds); 7.74 (1H,bds); 8.68 (1H,t); 8.98 (1H,bds). MS (ES+) m/z 648.4 (MH$^+$) Anal.calculated for C$_{36}$H$_{39}$F$_2$N$_3$O$_4$S.2.8H$_2$O C, 61.9; H, 6.4; N, 6.0; Found: C, 61.7; H, 6.0; N, 5.6.

EXAMPLE 38 tert-Butyl (2S)-2-{5-[1-(4-fluorophenyl)-2-(imidazol-1-yl)ethoxy]-2-(4-fluorophenethy) benzoylamino}-4-methylsulfonylbutyrate A mixture of 5-[(1-(4-fluorophenyl)-2-(imidazol-1-yl) ethoxy)]-2-(4-fluorophenethyl)benzoic acid (800 mg, 1.79 mmol), tert-butyl (2S)-2-amino-4-(methylsulfonyl) butanoate (L-methionine sulphone tert-butyl ester) (630 mg, 2.68 mmol), and DMAP (870 mg, 7.1 mmol), was treated with EDC.HCl (510 mg, 2.7 mmol) was stirred at ambient temperature for 16 hours. The reaction mixture was washed with aqueous citirc acid (1M, 2×), brine, dried (MgSO$_4$) and evaporated to dryness. The residue was purified by chromatography on silica (40 gm Dynamax column, gradient elution 2–10% methanol/dichloromethane) to give a gum which, when triturated with diethyl ether/iso-hexane, gave the title compound as a cream solid (889 mg, 74%).

$^1$H NMR (DMSO-d$_6$,+HOAc-d$_4$, 300 MHz) δ: 1.38 (9H, s); 2–2.25 (2H,m); 2.62–2.82 (4H,m); 2.97 (3H,d); 3.02–3.28 (2H,m); 4.36–4.42 (1H,dd); 4.6–4.67 (2H,d); 5.76–5.82 (1H,m); 6.78–6.84 (1H,m); 6.86–6.92 (1H,m); 6.92–7.05 (3H,m); 7.1–7.24 (4H,m); 7.4–7.58 (3H,m); 7.64–7.7 (1H,bds); 8.88–9.0 (1H,bds). MS (ES+) m/z 668.3 (MH+); Anal.calculated for C$_{35}$H$_{39}$F$_2$N$_3$O$_6$S.3H$_2$O C, 58.2; H, 6.2; N, 5.8; Found: C, 58.1; H, 6.0; N, 5.6.

The starting material was prepared as follows:

A mixture of methyl 2-bromo-5-methoxybenzoate (28.3 g, 115 mmol), 4-fluorostyrene (20.6 ml, 173.3 mmol), tert-n-butylamine (2.7 ml, 11.5 mmol), Pd[(o-tolyl)$_3$ P]$_2$ Cl$_2$ (0.9 g, 1.15 mmol), and NaHCO$_3$ (14.6 g, 173.3 mmol), and water (220 ml) was stirred and heated at reflux for 16 hours. The reaction mixture was diluted with water (200 ml) and extracted with ethyl acetate (2×400 ml). The extracts were washed with 2M HCl (100 ml), water (100 ml), brine (100 ml), dried (MgSO$_4$), filtered and evaporated to dryness. The brown gum obtained was purified by chromatography on silica (90 g, Biotage column), eluting with a gradient of ethyl acetate in iso-hexane (0%–20% ethyl acetate). The relevant fractions were combined and evaporated to give methyl 2-[2-(4-fluorophenyl)ethenyl]-5-methoxybenzoate, (43.5 g)

$^1$H NMR (CDCl$_3$, 250 MHz) δ: 3.86 (3H,s); 3.94 (3H,s); 6.86 (1H,d); 7.02 (1H,d); 7.04–7.12 (3H,m); 7.42–7.52 (3H,m); 7.64 (1H,d); 7.83 (1H,d). MS (ES+) m/z 287 (MH+).

Methyl 2-[2-(4-fluorophenyl)ethenyl]-5-methoxybenzoate (43 g, 150 mmol) in ethyl acetate (3.5L) was stirred with 10% Pd/C (4 g) under an atmosphere of hydrogen (pressure 5 bar), at ambient temperature for 18 hours. The spent catalyst was removed by filtration through a Celite pad, the pad was washed with ethyl acetate and the filtrate evaporated to dryness to give methyl 2-(4-fluorophenethyl)-5-methoxybenzoate (33.8 g, 80% yield).

$^1$H NMR (CDCl$_3$, 300 MHz) δ: 2.84 (2H, t); 3.16 (2H, t); 3.8 (3H, s); 3.88 (3H,s); 6.86–7.0 (3H,m); 7.06 (1H,d); 7.08–7.2 (2H, m); 7.43 (1H, d). MS (ES+) m/z 289 (MH+).

Methyl 2-(4-fluorophenethyl)-5-methoxybenzoate (33.8 g, 117 mmol) and pyridine hydrochloride (170 g) were heated at 220° C. for 2 hours. The black reaction mixture was cooled, poured into 2N HCl (1 L), and the pale-brown solid extracted with ethyl acetate (2×450 ml). The extracts were washed with 2N HCl (500 ml), brine (200 ml), dried (MgSO$_4$) and evaporated to give 2-(4-fluorophenethyl)-5-hydroxy benzoic acid (30 g, quantitative).

$^1$H NMR (DMSOd$_6$, 300 MHz) δ: 2.74 (2H, t); 3.04 (2H, t); 6.81 (1H, dd); 7.12 (3H,t); 7.15–7.24 (3H, m).

A solution of 2-(4-fluorophenethyl)-5-hydroxybenzoic acid (30 g, 115.4 mmol) in methanol (900 ml) and the stirred solution treated dropwise with sulphuryl chloride (1.6 ml, 19.6 mmol) stirred and heated at reflux for 16 hours. The mixture was evaporated to dryness, the residue dissolved in ethyl acetate (500 ml), washed with saturated aqueous NaHCO$_3$ (×2), water and brine. After drying (MgSO$_4$) the solution was evaporated to dryness to give a brown oil which when triturated with iso-hexane gave methyl 2-(4-fluorophenethyl)-5-hydroxybenzoate (21.02 g, 66%).

$^1$H NMR (CDCl$_3$, 300 MHz) δ: 2.84 (2H, t); 3.15 (2H,t); 4.8–5.2 (1H,broad); 7.85–7.0 (3H, m) 7.02 (1H,d); 7.12 (2H, dd); 7.39 (1H, d). MS (ES+) m/z 275 (MH+). Anal.calculated for C$_{16}$H$_{15}$FO$_3$ C, 70.06; H, 5.51; Found: C, 70.0; H, 5.6.

A mixture of 1-(4-fluorophenyl)-2-imidazol-1-yl)ethanol, (5.0 g, 24 mmol), methyl 2-(4-fluorophenethyl)-5-hydroxybenzoate, (7.3 g ,27 mmol), DEAD (4.2 ml,4.65 g, 27 mmol), and triphenyl phosphine (7.0 g, 27 mmol) in dry THF (150 ml) was stirred at ambient temperature for 16 hours. The reaction was evaporated to dryness and the residue purified by chromatography on silica (90 g Biotage column, gradient elution 1–20% methanol/dichloromethane). The appropriate fractions were combined and evaporated to dryness to give methyl 5-[1-(4-fluorophenyl)-2-imidazol-1-yl)ethoxy]-2-(4-fluorophenethyl)benzoate (13.46 g ). The material was used without further purification in the next reaction.

MS (ES+) m/z 463 (MH+).

Methyl {5-[1-(4-fluorophenyl)-2-imidazol-1-yl)ethoxy]-2-(4-fluorophenethyl) benzoate (13.46 g , ~29 mmol), was dissolved in methanol (100 ml) and stirred at ambient temperature, with 2N aqueous sodium hydroxide solution (73 ml, 146 mmol) for 4 days. The methanol was removed by evaporation and the residual aqueous solution adjusted to PH 7 with 2N HCl before being evaporated to dryness. The resulting white solid was purified by chromatography on silica (90 g Biotage column, gradient elution 2–20% methanol/dichloromethane) to give 5-[1-(4-fluorophenyl)-2-imidazol-1-yl)ethoxy]-2-(4-fluorophenethyl)benzoic acid (4.0 g), as a colourless foam.

$^1$H NMR (CDCl$_3$, 300 MHz) δ: 2.84 (2H, t); 3.16 (2H, t); 4.34 (2H,d); 5.26–5.37 (1H, m); 6.66 (1H, dd); 6.88 (3H,t); 7.0–7.18 (5H,m); 7.22–7.35 (2H, m); 7.54 (1H, d); 7.92 (1H, s). MS (ES–) m/z447 (MH–).

EXAMPLE 39

2-{5-[1-(4-Fluorophenyl)-2-(imidazol-1-yl)ethoxy]-2-(4-fluorophenethyl)benzoylamino}-4-methylsulfonylbutyric acid A solution of tert-butyl (2S)-2-{-5-[1-(4-fluorophenyl)-2-(imidazol-1-yl)ethoxy]-2-(4-fluorophenethyl) benzoylamino}-4-methylsulfonylbutyrate, (88 mg, 0.13 mmol) in TFA (2 ml), was stirred and cooled in an ice-bath for 3 hours. The TFA was removed by evaporation, the residue was dissolved in ethyl acetate and 1M HCl/diethylether (5 ml). Removal of the solvent gave a brown oil which on trituration with diethylether/iso-hexane (3×) gave the HCl salt of the title compound as a sticky white solid (40 mg).

$^1$H NMR (DMSO-d$_6$, 373° K., 250 MHz) δ: 2.1–2.42 (2H,m); 2.75–2.85 (2H,m); 2.85–2.94 (2H,m); 2.95 (3H,d); 3.05–3.35 (2H,m); 4.5–4.6 (1H, m); 4.62–4.68 (2H,m); 5.73 (1H,t); 6.78–6.88 (1H,dd); 6.9–7.1 (4H,m); 7.1–7.25 (4H, m); 7.3–7.65 (4H,m); 8.09 (1H,d); 8.59 (1H,bds). MS (ES+) m/z 612.3 (MH+).

EXAMPLE 40

Methyl (2S)-2-{5-[1-(thiazol-2-yl) -2-(imidazol-1-yl)ethoxy]-2-(4-fluorophenethyl)benzoylamino}-4-methylsulfanylbutyrate A mixture of 5-[1-(thiazol-2-yl)-2-(imidazol-1-yl) ethoxy]-2-(4-fluorophenethyl)benzoic acid (1.1 g, 2.52 mmol), L-methionine methyl ester. HCl (1.0 g, 5.0 mmol), DMAP (1.54 g, 12.6 mmol), in dichloromethane (40 ml) and EDC.HCl (0.72 g 3.8 mmol ) was stirred for 16 hours. The mixture was washed with 1M citric acid (×2) and with brine, dried (MgSO$_4$), evaporated to dryness and the residue obtained purified by chromatography on silica (40 gm Biotage column, gradient elution with 2–10% methanol/ dichloromethane). The appropriate fractions were combined and evaporated to give the title compound (0.14 gm, 64%).

$^1$H NMR (DMSO-d6, 300 MHz) δ: 1.94–2.04 (5H,m); 2.52–2.6 (2H,m); 2.65–2.85 (4H,m); 3.6 (3H,s); 4.52–4.65 (3H,m); 5.98–6.05 (1H, m); 6.82 (1H,s); 6.88–6.96 (2H,m); 7.0–7.2 (6H,m); 7.5 (1H,d); 7.76 (1H,d); 7.86 (1H,d); 8.64 (1H,t). MS (ES+) m/z 583.3 (MH+). Anal.calculated for $C_{29}H_{31}FN_4O_4S_2.0.3H_2O$ C, 59.2; H, 5.4; N, 9.5; Found: C, 59.2; H, 5.3; N, 9.3.

The starting material was prepared as follows:

A mixture of 2-bromo-1-(thiazol-2-yl)ethanone (2.5 g; 12 mmol), acetonitrile (70 ml) and imidazole (1.65 g; 24 mmol) was stirred at ambient temperature for 1 hour. The mixture was evaporated to dryness and the residue partitioned between dichloromethane and water. The organic phase was separated, washed with saturated brine and evaporated to give 2-(imidazol-1-yl)-1-(thiazol-2-yl)-ethanone as a brown solid (1.17 g; 50%).

MP: 109–112° C. $^1$H NMR (DMSO d$_6$, 400 MHz) δ: 5.6 (2H,s); 6.85–8.1 (5H,m).

2-(Imidazol-1-yl)-1-(thiazol-2-yl)ethanone was reduced with sodium borohydride in methanol to give 2-(imidazol-1-yl)-1-(thiazol-2-yl)ethanol in 60% yield.

$^1$H NMR (CDCl$_3$, 300 MHz) δ 4.15 (1H,dd); 4.57 (1H,dt); 5.2 (1H, dd); 6.75 (1H,s); 6.89 (1H,s); 7.32–7.41 (2H,m); 7.79 (1H,d). MS (ES+) m/z 196 (MH)+.

Methyl 5-[2-(imidazol-1-yl)-1-(thiazol-2-yl)ethoxy]-2-(4-fluorophenethyl)benzoate was prepared from 2-(imidazol-1-yl)-1-(thiazol-2-yl)ethanol and methyl 2-(4-fluorophenethyl)-5-hydroxybenzoate by the Mitsunobu methodology used for the preparation of methyl 5-[2-(2-methylimidazol-1-yl)-1-(4-fluorophenyl)ethoxy]-2-(4-fluorophenethyl)benzoate in Example 45.

$^1$H NMR (CDCl$_3$, 300 MHz) δ 2.8 (2H,t); 3.12 (2H,t); 3.88 (3H,s); 4.52 (1H,dd); 4.62 (1H,dd); 5.76 (1H, dd); 6.85–6.97 (4H,m); 7.0–7.15 (4H,m); 7.34 (1H,d); 7.45 (1H, d); 7.48(1H,s); 7.86 (1H,d). MS (ES+) m/z 452 (MH)+. Methyl 5-[2-(imidazol-1-yl)-1-(thiazol-2-yl)ethoxy]-2-(4-fluorophenethyl)benzoate was hydrolysed using aqueous sodium hydroxide solution to give 5-[2-(imidazol-1-yl)-1-(thiazol-2-yl)ethoxy]-2-(4-fluorophenethyl)benzoic acid.

$^1$H NMR (CDCl$_3$, 300 MHz) δ 2.85 (2H,t); 3.2 (2H,t); 4.54 (1H,dd); 4.68 (1H,dd); 5.8211H,dd); 6.86.8–7.04 (5H, m); 7.04–7.16 (3H,m); 7.36 (1H,d); 7.59 (1H,d); 7.88 (2H,t). MS (ES+) m/z 438 (MH)+.

EXAMPLE 41

(2S)-2-{5-[1-(Thiazol-2-yl)-2-(imidazol-1-yl) ethoxy]-2-(4-fluorophenethyl)benzoylamino}-4-methylsulfanylbutyric acid Methyl (2S)-2-{5-[1-(2-thiazolyl) -2-(imidazol-1-yl) ethoxy]-2(4-fluorophenethyl)benzoylamino}-4-methylsulfanylbutyrate (140 mg, 0.24 mmol) was dissolved in methanol (3 ml), and treated with NaOH (190 mg, 4.8 mmol) in H$_2$O (1 ml). After 4 hours at ambient temperature, the miuture was acidified to PH 1 with 1M HCl and the mixture evaporated to dryness. The residue was washed with water (3×2 ml) and the resulting gum triturated with iso-hexane to give the HCl salt of the title compound (94 mg, 69%) as a white solid.

$^1$H NMR (DMSO-d$_6$, HOAc-d$_4$, 300 MHz) δ: 1.84–2.1 (5H,m); 2.5–2.6 (signals partially obscured by the solvent signals, m); 2.65–2.78 (2H,m); 2.78–2.9 (2H,m); 4.4–4.51 (1H,dd); 4.8–4.98 (2H, m); 6.18–6.24 (1H,m); 6.8–7.04 (4H,m); 7.06–7.2 (3H,m); 7.59 (1H,s); 7.74 (1H,d); 7.86 (1H,d); 9.14 (1H,m). MS (ES+) m/z 569.2 (MH+). Anal. calculated for $C_{32}H_{37}F N_4O_6S_2.HCl.1.1H_2O.0.5NaCl$: C, 51.4; H, 5.0; N, 8.6; Found: C, 51.5; H, 4.7; N, 8.5.

EXAMPLE 42 tert-Butyl (2S)-2-{5-[1-(thiazol-2-yl) -2-(imidazol-1-yl)ethoxy]-2-(4-fluorophenethyl)benzoylamino}-4-methylsulfanylbutyrate The title compound was prepared in 42% yield from 5-[1-(thiazol-2-yl)-2-(imidazol-1-yl)ethoxy-2-(4-fluorophenylethyl)benzoic acid and L-methionine tert-butyl ester by a similar method to that used for Example 40.

$^1$H NMR (DMSO-d$_6$, 300 MHz) δ: 1.39 (9H,s); 1.9–2.0 (2H,m); 2.02 (3H,s); 2.5–2.6 (2H,m); 2.68–2.78 (2H,m); 2.78–2.9 (2H, m); 4.36–4.45 (1H,m); 4.58–4.7 (2H,m); 6.0–6.05 (1H,m); 6.86–6.96 (2H,m); 6.98–7.08 (2H,t); 7.1–7.2 (4H,m); 7.5–7.65 (2H,m); 7.73 (1H,d); 7.86 (1H,d); 8.63 (1H,t). MS (ES+) m/z 625.3 (MH+). Anal.calculated for $C_{32}H_{37}FN_4O_4S_2.1.25C_6H_8O_7$ (Citric acid) C, 54.9; H, 5.5; N, 6.5; Found: C, 54.9; H, 5.5; N, 6.7.

EXAMPLE 43 tert-Butyl (2S)-2-{5-[1-(thiazol-2-y)-2-(imidazol-1-yl)ethoxy]-2-(4-fluorophenethyl)benzoylamino}-4-methylsulfonylbutyrate The title compound was prepared in 75% yield from 5-[1-(thiazol-2-yl)-2-(imidazol-1-yl)ethoxy]-2-(4-fluorophenethyl)benzoic acid and L-methionine sulphone tert-butyl ester by similar methodology to that used for Example 40.

$^1$H NMR (DMSO-d$_6$, HOAc$_4$, 300 MHz) δ: 1.37 (9H,s); 2.0–2.26 (2H,m); 2.6–2.8 (4H,dd); 2.75–2.94 (3H,m); 2.98 (3H,d); 3.1–3.38 (3H,m); 4.354.44 (1H,m); 4.7–4.84 (2H, m); 6.1–6.18 (1H,dd); 6.9–7.05 (3H,m); 7.08–7.2 (4H,m); 7.24 (1H,s); 7.48 (1H,s); 7.74 (1H,d); 7.88 (1H,d); 8.4 (1H,s); 8.72 (1H,t). MS (ES+) m/z 657.3 (MH+). Anal.calculated for $C_{28}H_{29}FN_4O_4S_2.1.2C_6H_8O_7$ (Citric acid).2.6H$_2$O C, 50.4; H, 5.6; N, 6.0; Found: C, 50.1; H, 5.4; N, 6.3.

EXAMPLE 44

(2S)-2-{5-[1-(Thiazol-2-yl)-2-(imidazol-1-yl) ethoxy]-2-(4-fluorophenethyl)benzoylamino}-4-methylsulfonylbutyric acid Treatment of tert-butyl (2S)-2-{5-[1-(thiazol-2-yl) -2-(imidazol-1-yl)ethoxy]-2(4-fluorophenethyl) benzoylamino}-4-methylsulfonylbutyrate with TFA by a similar method to that used for Example 39 gave the HCl salt of the title compound in 73% yield.

$^1$H NMR (DMSO-d$_6$, 250 MHz) δ: 2.0–2.3 (2H,m); 2.45–2.55 (partially obscured by the solvent signals, m); 2.55–2.9 (7H,m); 2.94 (3H,d); 3.1–3.28 (2H,m); 4.48–4.5 (1H,m); 4.82–4.94 (2H,m); 6.2–6.3 (1H,m); 6.88–7.02 (4H, m); 7.05–7.2 (3H,m); 7.62 (1H,t); 7.75 (2H,m); 7.86 (1H,d); 8.64–8.72 (1H,t); 9.16(1H,m). MS (ES−) m/z 599.1 (MH−). Anal.calculated for $C_{28}H_{29}FN_4O_6S_2.HCl$ 0.4H$_2$O0.1.0C$_6$H$_8$O$_7$ (Citric acid). C, 45.3; H, 5.1; N, 6.2; Found: C, 45.2; H, 4.7; N, 6.1.

EXAMPLE 45

Methyl (2S)-2-{5-[1-(4-fluorophenyl)-2-(2-methylimidazol-1-yl)ethoxy]-2-(4-fluorophenethyl)benzoalamino}-4-methylsulfanylbutarate The title compound was obtained from 2-(4-fluorophenethyl)-5-methoxybenzoic acid and L-methionone methyl ester in 54% yield by a similar method to that used for Example 40.

$^1$H NMR (DMSO-d$_6$, 300 MHz) δ: 1.87–2.08 (5H,m); 2.54 (3H,s); 2.58–2.9 (6H,m); 3.6 (3H,s); 4.44–4.65 (3H,m); 5.76–5.84 (1H, m); 6.78–6.82 (2H,m); 6.95–7.06 (3H,m); 7.1–7.2 (4H,m); 7.4–7.58 (3H,m); 7.6 (1H,d); 8.72 (1H,t). MS (ES+) m/z 608.4 (MH+).

The starting material was prepared as follows:

A mixture of 2-methylimidazole (8.0 g, 97.5 mmol) and 4-fluorophenacyl bromide (21.16 g, 97.5 mmol) dissolved in ethyl acetate (40 ml) at ambient temperature was treated with tiethylamine (16.4 ml, 117 mmol) and the cloudy mixture heated at reflux for 16 hours. The mixture was cooled to ambient temperature and diluted with ethyl acetate and water, washed with water and brine, dried and evaporated to dryness. The residue was recrystallised (3×) from dichloromethane/methanol/isohexane to give 1-(4-fluorophenyl)-2-(2-methylimidazol-1-yl)ethanone (1, 9.0 g, 42%).

$^1$HNMR (DMSO d$_6$, 300 MHz) δ: 2.12 (3H,s); 5.64 (2H, s); 6.72 (1H,s); 6.96 (1H,s); 7.34 (2H,t); 8.12 (2H,dd). MS (ES+) m/z 219 (MH)+.

A cooled (ice-bath) solution of 1-(4-fluorophenyl)-2-(2-methylimidazol-1-yl)ethanone (9.0 g, 41.3 mmol) in methanol (60 ml) was treated portionwise with sodium borohydride (1.56 g; 41.3 mmol) and the mixture stirred at ambient temperature for 16 hours. Most of the methanol was removed and water and ethyl acetate added. The organic layer was separated, the aqueous extracted with ethyl acetate (2×) and the combined organic extracts washed with water, brine, dried filtered and evaporated to give a residue which was triturated with diethyl ether to give 1-(4-fluorophenyl)-2-(2-methylimidazol-1-yl)ethanol (7.7 g, 84%).

$^1$H NMR (CDCl$_3$, 300 MHz ) δ 2.14 (3H,s); 3.98 (2H,d); 4.88 (1H,t); 6.74 (1H,s); 6.8 (1H,s); 7.04 (2H, t); 7.21–7.32 (2H,m). MS (ES+) m/z 221 (MH)+.

DEAD (1.95 g, 12 mmol) added to a mixture of 1-(4-fluorophenyl)-2-(2-methylimidazol-1-yl)ethanol (2.48 g, 11 mmol), methyl 2-(4-fluorophenethyl)-5-hydroxybenzoate (3.4 g, 12 mmol), and triphenyl phosphine (3.3 g, 12 mmol), in THF (60 ml). The mixture was cooled in an ice-bath. After stirring for 16 hours the mixture was evaporated to dryness and the residue purified by chromatography on silica (90b Biotage column, gradient elution 1–20% methanol/dichloromethane). Appropriate fractions were collected and evaporated to give methyl 5-[1-(4-fluorophenyl)-2-(2-methylimidazol-1-yl)ethoxy]-2-4-fluorophenethyl)benzoate (4.2 g, ~75%) which was used without further purification.

$^1$H NMR (CDCl$_3$, 300 MHz) δ 2.21 (3H,s); 2.76 (2H, t); 3.08 (2H,t); 4.12–4.32 (1H,m); 5.3 (1H,t); 6.72–6.8 (1H, m); 6.84–6.98 (5H,m); 7.0–7.14 (4H,m); 7.16–7.24 (2H,m); 7.3 (1H,d). MS (ES+) m/z 477 (MH)+; 279 (MH)+ for Ph$_3$O.

Methyl 5-[1-(4-fluorophenyl)-2-(2-methylimidazol-1-yl)ethoxy]-2-(4-fluorophenethyl)benzoate (4.2 g, ~8.8 mmol) was hydrolysed with aqueous sodium hydroxide solution under the usual conditions to give 5-[1-(4-fluorophenyl)-2-(2-methylimidazol-1-yl)ethoxy]-2-(4-fluorophenethyl)benzoic acid (1.84 g, ~45% ) as a colourless gum.

$^1$HNMR (DMSO d$_6$, 300 MHz) δ 2.52 (3H,s); 2.68 (2H,t); 3.0 (2H, dd); 4.48–2.04 (2H,m); 5.76–5.86 (1H,m); 6.9–6.98 (1H, m); 7.0–7.28(9H,m); 7.48 (2H,t); 7.62 (1H,d). MS (ES+) m/z 463 (MH)+.

EXAMPLE 46

(2S)-2-{5-[1-(4-Fluorophenyl)-2-(2-methylimidazol-1-yl)ethoxy]-2-(4-fluorophenethyl)benzoylamino}-4-methylsulfanylbutyric acid Treatment of methyl (2S)-2-{5-[1-(4-fluorophenyl)-2-(2-methylimidazol-1-yl)ethoxy]-2-(4-fluorophenethyl)benzoylamino}-4-metbylsulfanylbutyrate with aqueous sodium hydroxide followed by the usual isolation procedure gave the hydrochloride salt of the title compound as a white solid in 64% yield.

$^1$H NMR (DMSO-d$_6$, 300 MHz) δ: 1.9–2.05 (5H,m); 2.57 (3H,s); 2.6–2.72 (2H,m); 2.75–2.85 (2H,m); 4.4–4.7 (3H, m); 5.78–5.86 (1H, m); 6.78–6.84 (2H,m); 6.95–7.08 (3H, m); 7.14–7.28 (4H,m); 7.45–7.55 (3H,m); 7.66 (1H,s); 8.58 (1H,t). MS (ES+) m/z 592 (MH+).

EXAMPLE 47 tert-Butyl (2S)-2-{4-[1-(4-fluorophenyl)-2-(imidazol-1-yl)ethoxy]-2-(4-fluorophenyl)benzoylamino}-4-methylsulfanylbutyrate The title compound was prepared, in 33% yield, from 5-(1-(4-fluorophenyl)-2-(imidazol-1-yl)ethoxy)-2-(4-fluorophenyl)benzoic acid and L-methionine tert-butyl ester by a similar method to that used for Example 38.

$^1$H NMR (DMSO-d$_6$, HOAc-d$_4$, 300 MHz) δ: 1.34 (9H,s); 1.64–1.8 (2H,m); 1.92 (3H,d); 2.04–2.28 (2H,m); 2.6–2.74 (4H,dd); 4.08–4.18 (1H, m); 4.48 (2H,bds); 5.82 (1H,bds); 6.82–6.94 (2H,m); 7.04–7.2 (6H,m); 7.2–7.38 (4H,m); 7.4–7.52 (2H,m). MS (ES+) m/z 608.3 (MH+). Anal.calculated for C$_{33}$H$_{35}$F$_2$N$_3$O$_4$S.0.9C$_6$H$_8$O$_7$ (Citric acid). 1.4H$_2$O C, 57.2; H, 5.6; N, 5.2; Found: C, 57.1; H, 5.2; N, 5.3.

The starting material was prepared as follows:

Sulphuryl chloride (4.4 ml) was carefully added to a solution of 4-hydroxy-2-(4-fluorophenyl)benzoic acid (20.8 g, 0.0896 mol) (from Example 32) in methanol (220 ml) and the mixture heated at reflux for 16 hours. The solvent was removed under reduced pressure and the residue partitioned between ethyl acetate and aqueous NaHCO$_3$ (pH ~8). The organic phase was washed with water, brine, dried (MgSO$_4$), filtered and evaporated to give a sticky brown solid which, on trituration with isohexane, gave methyl 4-hydroxy-2-(4-fluorophenyl)benzoate (14.34 g, 65% yield).

$^1$H NMR (CDCl$_3$, 300 MHz) δ 3.64 (3H,s); 5.56 (1H,s); 6.74 (1H,d); 6.84 (1H,dd); 7.03–7.12 (2H,m); 7.16–7.28 (2H,m); 7.84 (1H,d). MS (ES+) m/z 247 (MH)+.

Methyl 4-[2-(imidazol-1-yl)-1-(4-fluorophenyl)ethoxy]-2-(4-fluorophenyl)benzoate was prepared from methyl 2-(4-fluorophenyl)-4-hydroxybenzoate and 2-(imidazol-1-yl)-1-(4-fluorophenyl)ethanol using the Mitsunobu reaction as described for the preparation of methyl 5-[2-(2-methylimidazol-1-yl 1-(4-fluorophenyl/ethoxy]-2-(4-fluorophenethyl)benzoate.

$^1$H NMR (CDCl$_3$, 300 MHz) δ 3.6 (3H,s); 4.25–4.44 (2H,m); 5.4 (1H,t); 6.7–6.78 (2H,m); 6.92 (1H,s); 7.07.3 (10H,m); 7.44 (1H,s); 7.76 (1H,d). MS (ES+) m/z 435 (MH)+.

4-[2-(imidazol-1-yl)-1-(4-fluorophenyl)ethoxy]-2-(4-fluorophenyl) benzoic acid was prepared from methyl 4-[2-(imidazol-1-yl)-1-(4-fluorophenyl)ethoxy]-2-(4- fluorophenyl)benzoate by treatment with aqueous hydroxide in methanol and used without further purification.

¹HNMR (DMSO d$_6$, 300 MHz) δ 4.7(2H,d); 6.02 (1H,t); 6.82–6.94 (2H,m); 7.1–7.26(6H,m); 7.47(2H,dd); 7.62–7.68 (2H, m); 7.77 (1H,s); 9.16 (1H,s). MS (ES+) m/z 421 (MH)+.

EXAMPLE 48 tert-Butyl (2S)-2-{4-[1-(4-fluorophenyl)-2-(imidazol-yl)ethoxy]-2-(4-fluorophenyl)benzoylamino}-4-methylsulfonylbutyrate The title compound was prepared, in 59% yield, from 5-(1-(4-fluorophenyl)-2-(imidazol-1-yl)ethoxy)-2-(4-fluorophenethyl)benzoic acid and L-methionine sulphone tert-butyl ester by a similar method to that used for Example 34.

¹H NMR (DMSOd$_6$+HOAc d$_4$ 300 MHz) δ: 1.36 (9H,s); 1.8–1.94 (1H, m); 1.96–2.12 (1H, m), 2.62–2.8 (1H,m ); 2.86 (3H, d); 2.9–3.0 (1H,m); 4.1–4.2 (1H, m); 4.64 (2H, d); 5.9 (1H,m); 6.8–6.9 (2H,m); 7.05–7.3 (8H,m); 7.4–7.5 (3H, m); 7.64 (1H, m); 8.84 (1H, m). MS (ES+) m/z 640.3 (MH+). Anal.calculated for $C_{33}H_{35}F_2N_3O_6S.3.6H_2O$ C, 56.3; H, 6.00; N, 6.00; Found: C, 56.1; H, 5.60; N, 5.80.

EXAMPLE 49

2-{4-[1-(4-Fluorophenyl)-2-(imidazol-1-yl)ethoxy]-2-(4-fluorophenyl)benzoylamino}-4-methylsulfonylbutiric acid A solution of tert-butyl (2S)-2-{4-[1-(4-fluorophenyl)-2-(imidazol-1-yl)ethoxy]-2(4-fluorophenyl)benzoylamino}-4-methylsulfonylbutyrate (94 mg, 0.15 mmol) in TFA (4 ml) was stirred in an ice-bath for 3 hours. The TFA was evaporated under reduced pressure, the residue dissolved in the minimum amount of ethyl acetate/methanol, and 1M HCl/diethyl ether (5 ml) added. The pale yellow precipitate obtained was triturated with iso-hexane, filtered, washed with iso-hexane and dried under vacuum to give the title compound (29 mg).

¹H NMR (DMSOd$_6$, 373K, 250 MHz) δ: 1.9–2.27 (2H, m); 2.82–3.1 (5H,m); 3.65 (3H,s); 4.25–4.45 (1H,m); 4.69 (2H,d); 5.94 (1H,t); 6.82–6.98 (2H,m); 7.05–7.25 (4H,m); 7.26–7.4 (3H,m); 7.4–755 (3H,m); 7.6 (1H,s); 7.88 (1H,d); 8.76 (1Hbds). MS (ES+) m/z 584.2 (MH+) for the acid, 598.2 (MH+) for the methyl ester.

EXAMPLE 50

Methyl (2S)-2-{5-[2-(4-methylimidazol-1-yl)-1-(thiazol-2-yl)ethoxy]-2-(4-fluorophenethyl)benzoylamino}-4-methylsulfanylbutyrate A mixture of 5-[2-(4-methylimidazol-1-yl)-1-(thiazol-2-yl)ethoxy]-2-(4-fluorophenethyl)benzoic acid (0.4 g; 0.89 mM), L-methionine methyl ester hydrochloride (0.27 g, 1.35 mM) and DMAP (0.54 g, 4.43 mM) was stirred until solution and EDC (0.026 g, 1.35 mM) in dichloromethane was added and the mixture stirred for 18 hours. It was purified on silica using dichloromethane then methanol/dichloromethane (5:95) as eluant to give the title product (0.47 g, 89%) as a foam.

¹H NMR (CDCl$_3$, 300 MHz) δ: 2.09 (3H,d); 2.15 (3H,d); 2.12 (1H,m); 2.25 (1H,m); 2.60 (2H,m); 2.81 (2H, m); 2.95 (2H,m); 3.68 (3H,d); 4.42 (1H,dq); 4.55 (1H,dt); 4.84 (1H, m); 5.71 (1H,m); 6.50 (1H,dd); 6.65 (1H,s); 6.82 (1H,q); 6.91 (3H,m); 7.07 (3H,m); 7.38 (2H,m), 7.85 (1H,d). MS (ES+) m/z 597.4 (M+1 of $C_{30}H_{33}FN_4O_4S_2$ 596+1=597).

The starting material was prepared as follows:

A mixture of 4-methylimidazole (8.2 g, 0.1M), anhydrous potassium carbonate (13.8 g, 0.1M), potassium hydroxide (5.6 g, 0.1 M) and tetrabutylammonuim chloride (1.13 g, 3.51 mM) in methylene chloride (170 ml) at 0° C. was treated with ethyl 2-bromoacetate (8.35 g, 50 mM). The mixture was stirred at 0° C. for 1 hour and at ambient temperature, for 18 hours. It was then filtered and evaporated to dryness. The product was purified on silica using ethylacetate as eluant to give ethyl 4-methylimidazol-1-ylacetate and ethyl 5-methylimidazol-1-ylacteate (6.89 g, 82%) as a 2:1 mixture.

¹H NMR (CDCl$_3$, 300 MHz) δ: 1.39 (t, 3H), 2.16 (s, 3H), 5-Me, 2.23 (s, 3H), 4-Me, 4.24 (2M, q), 4.58 (s, 2H), 5-Me isomer 4.60 (s, 2H), 4-Me isomer, 6.65 (s, 1H) 4-Me isomer, 6.80 (s, 1H), 5-Me isomer, 7.37 (s, 1H), 4-Me isomer, 7.42 (s, 1H), 5-Me isomer.

A solution of n-butyl lithium (1.6 M in hexanes) (21.7 ml, 34.72 mM) in dry diethylether (25 ml) was treated slowly with a solution of 2-bromothiazole (2.84 ml, 31.5 mM) in dry diethyl ether (50 ml) at such a rate that the temperature did not exceed −65° C. A solution of ethyl 4-and 5-methylimidaol-1-ylacetate (6.89 g, 41 mM) in dry diethyl ether (25 ml) was then added. The mixture was stirred at −70° C. for 1½ hours, allowed to warm to ambient temperature over 3 hours and stirred for a further 18 hours. Saturated ammonium chloride solution (120 ml) was added slowly with stirring and the diethyl ether layer separated. The aqueous layer was extracted with diethyl ether and the combined organic extractions dried (MgSO$_4$) and evaporated to give a brown oil (5.85 g). This was purified on silica using isohexane/ethyl acetate as eluant to give 2-(4-methylimidazol-1-yl)-1-(thiazol-2-yl)ethanone (1.98 g, 30%) as an oil which crystallised on standing.

¹H NMR (CDCl$_3$, 300 MHz), δ: 2.26 (s, 3H), 5.49 (s, 2H), 6.69 (s, 1H), 7.44 (s, 1H), 7.80 (d, 1H), 8.07 (d, 1H). MS m/z 208.0 ($C_9H_9N_3OS$ of M$^+$+1 requires 208).

A solution of 2-(4-methylimidazol-1-yl)-1-(thiazol-2-yl)ethanone (1.96 g, 9.47 mM) in methanol (30 ml) was cooled in an ice bath, treated with NaBH$_4$ (0.358 g, 9.47 mM) and stirred for 18 hours. Ethyl acetate (60 ml) was then added, and the mixture washed with saturated aqueous NaHCO$_3$ solution, water, brine, dried (MgSO$_4$) and evaporated to give the product (0.56 g). The aqueous layer was reextracted with ethyl acetate to give an additional product. The product was purified on silica eluting with methanol/dichloromethane (10:90) to give 2-(4-methylimidazol-1-yl)-1-(thiazol-2-yl)ethanol (1.35 g, 68%).

¹H NMR (DMSO-d$_6$, 300 MHz), δ: 2.03 (s, 3H), 3.15 (d, 1H), 4.08 (q, 1H), 4.34 (dd, 1H), 5.05 (m, 1H), 6.76 (s, 1H), 7.34 (s, 1H), 7.64 (t, 1H), 7.98 (t, 1H). MS m/z 210.2 ($C_9H_{11}N_3OS$ of M$^+$+1 requires 210).

A stirred mixture of 2-(4-methylimidazol-1-yl)-1-(thiazol-2-yl)ethanol (1.35 g, 6.46 mM), methyl 2-(4-fluorophenethyl)-5-hydroxybenzoate (1.95 g, 7.1 mM) and triphenylphosphine (1.86 g, 7.1 mM) in dry THF was cooled in an ice bath, and treated with DEAD (1.24 g, 7.1 mM). The mixture was allowed to warm to ambient temperature, stirred for 18 hours and evaporated to dryness. The product was purified on silica using methanol/dichloromethane (3→10%) as eluant to give methyl 5-[2-(4-methylimidazol-1-yl)-1-(thiazol-2-yl)ethoxy]-2-(4-fluorophenethyl)benzoate (1.45 g, 48%).

This was then dissolved in methanol (19 ml) treated with 2M NaOH (9.4 ml), stirred for 18 hours, evaporated to dryness, redissolved in water (25 ml) and concentrated HCl added dropwise until pH 6. The mixture was extracted with ethyl acetate (3×30 ml), which was then washed with brine, dried (MgSO$_4$) and evaporated to dryness. The residue was purified on silica using methanol/dichloromethane (10→20%) to give 5-[2-(4-methylimidazol-1-yl)-1-(thiazol-2-yl)ethoxy]-2-(4-fluorophenethyl)benzoate as a white foam on evaporating to dryness (0.96 g, 68%).

$^1$H NMR (CDCl$_3$, 300 Mz), δ 2.21 (3H s), 2.85 (2H, t), 3.18 (2H, t), 4.44 (1H, q), 4.59 (1H, dd), 5.75 (1H, dd). 6.58 (1H, s), 6.80–6.94 (3H, m), 6.97 (1H, d), 7.12 (2H, dd), 7.37 (1H, d), 7.54 (1H, d), 7.85 (2H, d). MS, m/z 450.3 (C$_{24}$H$_{22}$FN$_3$O$_3$S=451 M$^-$ requires 451).

EXAMPLE 51 tert-Butyl (2S)-2-{5-[2-(4-methyimidazol-1-yl)-1-(thiazol-2-yl)ethoxy]-2-(4-fluorophenethyl)benzoylamino}-4-methylsulfonylbutyrate A mixture of 5-[2-(4-methylimidazol-1-yl 1-(thiazol-2-yl)ethoxy]-2-(4-fluorophenethyl)benzoate (0.56 g, 1.24 mM), L-methionine tert-butyl ester (1.02 g, 3.73 mM), EDC (0.48 g, 2.5 mM), N-methylmorpholine (0.68 ml, 7.31 mM) and 1-hydroxybenzotriazole (0.25 g, 1.85 mM) was stirred in dry DMF (22 ml) for 17 hours. It was then evaporated to dryness and the residue dissolved in dichloromethane, washed with saturated aqueous NaHCO$_3$ and purified on silica eluting with methanol/dichloromethane (5:95) to give the title compound as a white foam (0.68 g, 82%).

$^1$H NMR (CDCl$_3$, 300 MHz) δ: 1.50 (9H, s), 2.14 (3H, d), 2.30 (1H, m), 2.52 (1H, m), 2.81 (2H, t), 2.92 (3H+2H, s+m), 3.12 (1H, m), 3.27 (1H, m), 4.22 (1H, m), 4.55 (1H, dd), 5.72 (1H, m), 6.64 (2H, t), 6.80–6.94 (4H, m), 7.00–7.13 (3H, m), 7.37 (1H, t), 7.42 (1H, d), 7.84 (1H, d). MS m/z 669.3 (C$_{33}$H$_{39}$FN$_4$O$_6$S$_2$=670–1, M–=669).

EXAMPLE 52

(2S)-2-{5-[2-(4-Methylimidazol-1-yl)-1-(thiazol-2-yl)ethoxy]-2-(4-fluorophenethyl)benzoylamino}-4-methylsulfanylbutyric acid A mixture of Example 50 (70 mg, 0.12 mM), and 2M sodium hydroxide solution (0.7 ml, 0.7 mM) in methanol (2 ml) was stirred for 18 hours. It was then evaporated to dryness and dissolved in diethyl ether. Hydrochloric acid (1M) was added to pH 1 and then excess NH$_4$OH (0.8%) was added to pH 10. The mixture was evaporated to dryness, extracted with dichloromethane, filtered and evaporated to give the title product as a foam (44.4 mg, 65%).

$^1$H NMR (CDCl$_3$, 300 MHz) δ:2.06 (3H, d), 2.13 (1H, m), 2.22 (3H, d), 2.33 (1H, m), 2.61 (2H, m), 2.72 (2H, m), 2.92 (2H, m), 4.51 (2H, m), 4.77 (1H, m), 5.74 (1H, m), 6.30 (1H, d), 6.73 (1H, qd), 6.86 (2H, t), 6.93–7.08 (5H, m), 7.37 (1H, m), 7.83 (1H, m), 7.92 (1H, d). MS m/z 581.3 (C$_{29}$H$_{31}$FN$_4$O$_4$S$_2$=582–1=581 for M–).

EXAMPLE 53 tert-Butyl (2S)-2-{2-(4-fluorophenethyl)-5-[1-(4-fluorophenyl)-2-(1-methylimidazol-5-yl)ethoxy]benzoylamino}-4-methylsulfanylbutyrate A mixture of L-methionine-tert-butyl ester (0.240 g), (8) (0.175 g.), DMAP (0.237 g.), EDC (0.149 g.) and DMF (10 ml.) was stirred under an inert atmosphere for 16 hrs. The DMF was evaporated off and the residue partitioned between 1M aqueous citric acid (10 ml) and dichloromethane (10 ml). The organic layer was separated, dried and applied directly to a silica flash column which was then eluted with ethyl acetate/methanol (9:1). The product was converted to the hydrochloride salt to give tert-butyl (2S)-2-{2-(4-fluorophenethyl)-5-[1-(4-fluorophenyl)-2-(1-methylimidazol-5-yl)ethoxy]benzoylamino}-4-methylsulfanylbutyrate as a white solid (0.145 g.).

$^1$H NMR(DMSO-d$_6$) δ 1.4(9H, s), 1.96(2H, m), 2.05(3H, s), 2.5(2H, m), 2.7(2H, m), 2.8 (2H, m), 3.3(2H, m), 3.8(3H, s), 4.4(1H, m), 5.7(1H, m), 6.8–7.66(12H, m), 8.6(1H, dd), 9.0(1H, s). Anal. Calculated allowing for 1HCl, 0.5H$_2$O: C, 62.2; H, 6.2; N, 6.0. Found: C, 62.3; H, 6,6; N, 5.7. MS(MH$^+$) 650.

EXAMPLE 54 tert-Butyl (2S)-2-{2-(4-fluorophenethyl)-5-[1-(4-fluorophenyl)-2-(1-methylimidazol-5-yl)ethoxy]benzoylamino}-4-methylsulfonylbutyrate tert-Butyl (2S)-2-{2-(4-fluorophenethyl)-5-[1-(4-fluorophenyl)-2-(1-methylimidazol-5-yl)ethoxy]benzoylamino}-4-methylsulfonylbutyrate was prepared using a similar method to that used for Example 53 except using L-methionine-sulphone-tert-butyl ester instead of L-methionine tert-butyl ester.

$^1$H NMR(DMSO-d$_6$) δ 1.39(9H, s), 2.16(2H, m), 2.7(2H, m), 2.85(2H, m), 3.0(3H, d), 3.25(4H, m), 3.8(3H, s), 4.4(1H, m), 5.7(1H, m), 6.82–7.55(12H, m), 8.68(1H, dd), 8.93(1H, s). MS(MH$^+$) 682. Anal. Calculated allowing for 1HCl, 1.5 H$_2$O: C, 58.0; H, 6.0; N, 5.6. Found: C, 58.2; H, 6.0; N, 5.4.

The starting material was prepared as follows:

A mixture of 1-(4-fluorophenyl)-2-(1-methylimidazol-5-yl)ethanone (1.3 g.), sodium borohydride (0.25 g.) and methanol (50 ml.) was stirred at ambient temperature for 2 hours under an inert atmosphere. The methanol was evaporated away and water (30 ml.) added to the residue. The mixture was filtered and the solid washed with more water and dried to give 1-(4-fluorophenyl)-2-(1-methylimidazol-5-yl)ethanol (1.18 g.).

$^1$H NMR(DMSO-d$_6$) δ 2.84(2H, s), 3.4(3H, s), 4.75(1H, m), 5.43(1H, d), 6.56(1H, s), 7.2(2H, m), 7.32(2H, m), 7.48(1H,s). MS(MH$^+$) 221.

DEAD (0.85 g.) was added over 10 minutes to a solution of 1-(4-fluorophenyl)-2-(1-methylimidazol-5-yl)ethanol (0.9 g.), methyl 2-(4-fluorophenethyl)-5-hydroxybenzoate and triphenylphosphine (1.3 g.) in tetrahydrofuran (30 ml.), cooled to 15° C. under an inert atmosphere. The reaction was then stirred at ambient temperature for a further 16 hours. The THF was evaporated away and the residue dissolved in dichloromethane and applied directly to a silica flash column which was then eluted with firstly ethyl acetate then ethyl acetate/methanol (9:1) to give 2-(4-fluorophenethyl)-5-[1-(4-fluorophenyl)-2-(1-methylimidazol-5-yl)ethoxy]benzoate as a colourless gum (1.5 g.).

$^1$H NMR(CDCl$_3$) δ 2.78(2H, m), 3.1(3H, m), 3.23(1H, m), 3.4(3H, s), 3.85(3H, s), 5.29 (1H, t), 6.75–7.75(13H, m). MS(MH$^+$) 477.4.

A mixture of 2-(4-fluorophenethyl)-5-[1-(4-fluorophenyl)-2-(1-methylimidazol-5-yl)ethoxy]benzoate (1.5 g.), sodium hydroxide (0.62 g.), methanol (200 ml.) and water (30 ml.) was stirred at reflux for 16 hours. The mixture was then cooled, the methanol evaporated away and the residue diluted with water (100 ml.). It was then washed with dichloromethane and the aqueous phase separated, acidified with 1M aqueous citric acid (25 ml.) and extracted with dichloromethane. The extracts were dried and evaporated to dryness to give 2-(4-fluorophenethyl)-5-[1-(4-fluorophenyl)-2-(1-methylimidazol-5-yl)ethoxy]benzoic acid as a white foam (1.1 g).

EXAMPLE 55 tert-Butyl (2S)-2-{2-(4-fluorophenyl)-4-[1-(4-fluorophenyl)-2-(1-methylimidazol-5-yl)ethoxymethyl]benzoylamino}-4-methylsulfanylbutyrate and tert-Butyl (2S)-2-{2-(4-fluoropheny)-4-[1-(4-fluorophenyl)-2-(1-methylimidazol-5-yl)ethoxymethyl]benzoylamino}-4-methylsulfonylbutyrate The title compounds were synthesised from 2-(4-fluorophenyl)-4-[1-(4-fluorophenyl)-2-(1-methylimidazol-5-yl)ethoxymethyl]benzoic acid using a similar method to that described in Example 53.

tert-butyl (2S)-2-{2-(4-fluorophenyl)-4-[1-(4-fluorophenyl)-2-(1-methylimidazol-5-yl)ethoxymethyl]benzoylamino}-4-methylsulfanylbutyrate:

$^1$H NMR(DMSO-$d_6$) δ 1.39(9H, s), 1.82(2H, m), 1.99 (3H, s), 2.21(2H, m), 3.14(2H, m), 3.7(3H, s), 4.2(1H, m), 4.4(2H, s), 4.78(1H, m), 7.1–7.55(12H, m), 8.5(1H, d), 8.91(1H, s). Anal. Calculated allowing for 1HCl, 1H$_2$O C, 60.8; H, 6.1; N, 6.1. Found: C, 60.8; H, 5.8; N, 5.9. MS(MH$^+$) 636.4.

tert-butyl (2S)-2-{2-(4-fluorophenyl)-4-[1-(4-fluorophenyl)-2-(1-methylimidazol-5-yl)ethoxymethyl]benzoylamino}-4-methylsulfonylbutyrate:

$^1$H NMR(DMSO-$d_6$) δ 1.4(9H, s), 2.0(1H, m), 2.1(1H, m), 2.7–3.5(4H, m), 2.92(3H, s), 3.72(3H, s), 4.28(1H, m), 4.41(2H, s), 4.8(1H, m), 7.1–7.58(12H, m), 8.7(1H, d), 8.97(1H, s), 14.35(1H, br.s). Anal. Calculated allowing for 1HCl, 1.5H$_2$O C, 57.4; H, 5.7; N, 5.7. Found: C, 57.6; H, 5.8; N, 5.6. MS(MH$^+$) 668.3.

The starting material was prepared as follows:

Sodium hydride (0.089 g., 60% dispersion in oil) was added to a suspension of 1-(4-fluorophenyl)-2-(1-methylimidazol-5-yl)ethanol (0.27 g.) in THF (50 ml.) and DMF (7 ml.) stirred under an inert atmosphere. The mixture was stirred for a fulher 30 minutes. A solution of methyl 4-bromomethyl-2-(4-fluorophenyl)benzoate (0.432 g.) in THF(20 ml.) was then added followed by tetrabutylammonium iodide (0.045 g.) and the mixture stirred for a further 30 minutes. It was then poured into ice/saturated ammonium chloride solution and extracted with ethyl acetate. The extracts were dried, evaporated to dryness and the product purified by flash column chromatography eluting with firstly ethyl acetate, then ethyl acetate/methanol (9:1) to give 2-(4-fluorophenyl)-4-[1-(4-fluorophenyl)-2-(1-methylimidazol-5-yl)ethoxymethyl]benzoate as a colourless gum (0.38 g.).

2-(4-Fluorophenyl)-4-[1-(4-fluorophenyl)-2-(1-methylimidazol-5-yl)ethoxymethyl]benzoate was hydrolysed to give 2-(4-fluorophenyl)-4-[1-(4-fluorophenyl)-2-(1-methylimidazol-5-yl)ethoxymethyl]benzoic acid, using a similar method to that used to prepare 2-(4-fluorophenethyl)-5-[1-(4-fluorophenyl)-2-(1-methylimidazol-5-yl)ethoxy]benzoic acid in Example 54.

EXAMPLE 56

(2S)-2-{2-(4-Fluorophenyl)-6-[1-(4-fluorophenyl)-2-(imidazol-1-yl)ethoxy]pyrid-3-olyamino}-4-methylsulfanylbutyric acid A solution of tert-butyl (2S)-2-{2-(4-fluorophenyl)-6-[1-(4-fluorophenyl)-2-(imidazol-1-yl)ethoxy]pyrid-3-oylamino}-4-methylsulfanylbutyrate (0.1 g.) in TFA(20 ml.) was stirred at ambient temperature under an inert atmosphere for 30 minutes. The TFA was evaporated away and the residue was converted to the hydrochloride salt to give (2S)-2-{2-(4-fluorophenyl)-6-[1-(4-fluorophenyl)-2-(imidazol-1-yl)ethoxy]pyrid-3-oylamino}-4-methylsulfanylbutyric acid as a white solid (0.092 g.).

$^1$H NMR(DMSO$_6$) δ 1.95(2H, m), 2.1(3H, d), 2.3(1H, m), 2.48(1H, m), 4.4(1H, m), 4.9(2H, m), 6.65(1H, m), 7.06(1H, d), 7.2–7.5(4H, m), 7.55–7.8(5H, m), 7.85(1H, d), 7.9(1H, m), 8.74(1H, dd), 9.29(1H, d). Anal. Calculated allowing for 2HCl, 0.25Et2O: C, 54.0; H, 4.7; N, 8.7; S, 5.0. Found: C, 54.5; H, 4.7; N, 9.0; S, 5.3. MS(MH$^+$) 553.3.

The starting materialwas prepared as follows:

Thionyl chloride (3.8 g.) was added dropwise, over 10 minutes, to a solution of 2-chloropyridin-3-carboxylic acid HCl salt (1.0 g.) in methanol, stirred under an inert atmosphere and cooled in an ice/salt bath. The reaction was stirred for a further 5 days at ambient temperature. The methanol was evaporated away and the residue treated with saturated sodium bicarbonate solution and extracted with ethyl acetate. The extracts were dried and evaporated to dryness to give methyl 2-chloropyridin-3-carboxylate as a colourless liquid (0.9 g.)

$^1$H NMR(DMSO-$d_6$) δ 3.87(3H, s), 7.57(1H, dd), 8.25 (1H, dd), 8.6(1H, dd). MS(MH$^+$) 172.

A mixture of methyl 2-chloropyridin-3-carboxylate (6.8 g.), 4-fluorobenzeneboronic acid (7.2 g.), 1M. aqueous sodium carbonate (40 ml.), Pd(dppb)Cl$_2$(1.2 g.), ethanol(10 ml.) and toluene(150 ml.) was stirred at reflux under an inert atmosphere for 5 hr. The reaction was then cooled, the oganic layer separated, the aqueous extracted with toluene and then the Icombined extracts dried and evaporated to dryness. The product was purified by flash column chromatography eluting wth ethyl acetate/iso-hexane(9:1,8:2,7:3) to give methyl 2-(4-fluorophenyl)pyridin-3-carboxylate as a white solid(7.5 g.)

$^1$H NMR(DMSO-$d_6$) δ 3.71(3H, s), .7.1(2H, t), 7.32(1H, dd), 7.52(2H, m), 8.1(1 H, dd), 8.76(1H, dd). MS(MH$^+$) 232.

A mixture of methyl 2-(4-fluorophenyl)pyridin-3-carboxylate (10.5 g.) and MCPBA (12.33 g., 65%) in dichloromethane was stirred at 0° C. for 1 hour and then at ambient temperature for 2 hours. It was then washed with saturated sodium bicarbonate solution (300 ml.), dried and applied directly to a silica flash column which was eluted firstly with ethyl acetate/iso-hexane (1:1), ethyl acetate and ethyl acetate/methanol (9:1) to give 2-(4-fluorophenyl)-3-(methoxycarbonyl)pyridine-1-oxide as a white solid (10.5 g.).

$^1$H NMR(CDCl$_3$) δ: 3.63(3H, s), 7.18(2H, t), 7.31(1H, dd), 7.41(2H, t), 7.66(1H, d), 8.42 (1H, d). (1H, d). MS(MH$^+$) 248.

A solution of 2-(4-fluorophenyl)-3-(methoxycarbonyl)pyridine-1-oxide (10.5 g.) in acetic anhydride (500 ml.) was stirred at reflux for 17 hr., cooled, evaporated to dryness and the residue partitioned between saturated sodium bicarbonate solution and ethyl acetate. The organic layer was separated, dried and evaporated to dryness. The gum obtained was dissolved in methanol (400 ml.), treated with a solution of potassium carbonate (11.7 g.) in water (100 ml) and stirred at ambient temperature for 2 hours. The methanol was evaporated off, the aqueous residue diluted with more water (200 ml.) and the mixture filtered to give methyl 2-(4-fluorophenyl)-6-hydroxypyridin-3-carboxylate (8.0 g.) as a brown solid.

$^1$H NMR(CDCl$_3$) δ 3.62(3H, s), 6.46(1H, d), 7.14(2H, t), 7.4(2H, dd), 7.98(1H, d), 10.93(1H, br.s). MS(MH$^+$) 248.2.

Methyl 2-(4-fluorophenyl)-6-hydroxypyridin-3-carboxylate was reacted with 2-(imidazol-1-yl)-1-(4-fluorophenyl)ethanol by the procedure described for the preparation of 2-(4-fluorophenethyl)-5-[1-(4-fluorophenyl)-2-(1-methylimidazol-5-yl)ethoxy]benzoate to give methyl 2-(4-fluorophenyl)-6-[1-(4-fluorophenyl)-2-(imidazol-1-yl)ethoxy]pyridin-3-carboxylate.

$^1$H NMR(CDCl$_3$) δ: 3.68(3H, s), 4.32(1H, dd), 4.44(1H, dd), 6.31(1H, t), 6.82(1H, d), 6.83(1H, s), 7.08(5H, m), 7.38(1H, s), 7.69(4H, m), 8.07(1H, d). MS(MH$^+$) 436.4.

Methyl 2-(4-fluorophenyl)-6-[1-(4-fluorophenyl)-2-(imidazol-1-yl)ethoxy]pyridin-3-carboxylate was hydrolysed using sodium hydroxide to 2-(4-fluorophenyl)-6-[1-(4-fluorophenyl)-2-(imidazol-1-yl)ethoxy]pyridin-3-carboxylic acid.

$^1$H NMR(DMSO-d$_6$) δ 4.48(1H, dd), 4.58(1H, dd), 6.37 (1H, dd), 6.86(1H, s), 6.94(1H, d), 7.22(5H, m), 7.43(4H, m), 7.65(1H, s), 8.05(1H, d). MS(MH$^+$) 422.1.

2-(4-Fluorophenyl)-6-[1-(4-fluorophenyl)-2-(imidazol-1-yl)ethoxy]pyridin-3-carboxylic acid was converted to tert-butyl (2S)-2-{2-(4-fluorophenyl)-6-[1-(4-fluorophenyl)-2-(imidazol-1-yl)ethoxy]pyrid-3-oylamino}-4-methylsulfanylbutyrate by a similar method to that described for the preparation of tert-butyl (2S)-2-{2-(4-fluorophenethyl)-5-[1-(4-fluorophenyl)-2-(1-methylimidazol-5-yl)ethoxy]benzoylamino}-4-methylsulfanylbutyrate.

$^1$H NMR(DMSO$_6$) δ: 1.39(9H, d), 1.8(2H, m), 2.0(3H, d), 2.18(1H, m), 2.35(1H, m), 4.25(1H, m), 4.76(2H, m), 6.55 (1H, m), 6.98(1H, d), 7.12–7.38(4H, m), 7.42–7,7(5H, m), 7.74(1H, d), 7.8(1H, m), 8.62(1H, dd), 9.15(1H, d). MS(MH$^+$) 609.3. Anal. Calculated allowing for: 2.0 HCl, 0.25 i.hexane: C, 57.2; H, 5.6; N, 8.0; S, 4.6. Found: C, 57.5; H, 5.5; N, 8.2; S, 4.9.

EXAMPLE 57 tert-Butyl (2S)-2-{2-(4-fluorophenyl)-6-[1-(4-fluorophenyl)-2-(1-methylimidazol-5-yl)ethoxymethyl]pyrid-3-oyamino}-4-methybulfanylbutyrate 2-(4-Fluorophenyl)-6-[1-(4-fluorophenyl)-2-(1-methylimidazol-5-yl)ethoxymethyl]pyrid-3-carboxylic acid (0.39 g) and L-methionine-tert-butyl-ester.HCl (0.42 g) were dissolved in DMF (50 ml) then DMAP (0.63 g), EDC (0.25 g) and HOBT (0.12 g) were added under an inert atmosphere at ambient temperature. After 16 hours the solution was evaporated under reduced pressure, the residue obtained was diluted with 1M citric acid (10 ml) and extracted with 2% methanol/dichloromethane (1×100 ml, 1×60 ml). The combined extracts were dried, filtered and concentrated under reduced pressure to give a yellow oil. Purification by flash column chromatography eluting with methanol/ethyl acetate (9:1) gave tert-butyl (2S)-2-{2-(4-fluorophenyl)-6-[1-(4-fluorophenyl)-2-(1-methylimidazol-5-yl)ethoxymethyl]pyrid-3-oylamino}-4-methylsulfanylbutyrate as a colourless foam (0.34 g).

$^1$H NMR (CDCl$_3$) δ 1.43 (9H, s), 1.82–1.95 (2H, m), 2.04 (3H, s), 2.20–2.29 (2H, m), 2.88–2.99 (1H, m), 3.02–3.14 (1H, m), 3.20 (2H, s), 4.41–4.49 (1H, m), 4.55–4.66 (3H, m), 6.48 (1H, dd), 6.76 (1H, s), 7.00–7.15 (4H, m), 7.23–7.31 (4H, m), 7.58–7.66 (2H, m), 7.90(1H, dd). Anal. Calculated allowing for 0.5 H$_2$O: C, 63.2; H, 6.1; N, 8.7; Found: C, 63.0; H, 5.8; N, 8.7; MS (MH$^+$) 637.4.

The starting material was prepared as follows:

Methyl iodide (10.33 ml) was added to a stirred suspension of 2-chloro-6-nicotinic acid (22.8 g) and potassium carbonate (36.8 g) in DMF (190 ml), under an inert atmosphere at ambient temperature. After stirring vigorously for 16 hours the suspension was filtered and the solid residue washed with 10% methanol/dichloromethane (100 ml). The filtrate was then concentrated under reduced pressure and the residue diluted with water (250 ml), extracted with dichloromethane (3×150 ml) and the combined extracts dried and concentrated under reduced pressure. Purification by bulb to bulb distillation (140° C. @0.05 mmHg) gave methyl 2-chloro-6-nicotinoate as a white solid (23.6 g).

$^1$H NMR (CDCl$_3$) δ 2.50 (3H, s), 3.85 (3H, s), 7.10 (1H, d), 8.00 (1H, d). MS(MH$^+$) 186.

Methyl 2-chloro-6-nicotinoate (23.1 g) and 4-fluorobenzeneboronic acid (22.6 g) were dissolved in ethanol (25 ml) and toluene (350 ml) and Pd(dppb)Cl$_2$ (3.76 g) were added under an inert atmosphere. An aqueous solution of 1M, sodium carbonate (124 ml) was added and the suspension heated at reflux for 4 hours and cooled to ambient temperature. The organic layer was separated and the aqueous layer extracted with dichloromethane (3×100 ml). The combined organic extracts were dried, filtered and concentrated under reduced pressure to give a yellow oil. Purification by flash column chromatography eluting with ethyl acetate/iso-hexane (4:6) gave methyl 2-(4-fluorophenyl)-6-methylpyridin-3-carboxylate as a pale yellow solid (27.8 g).

$^1$H NMR (CDCl$_3$) δ 2.64 (3H, s), 3.68 (3H, s), 7.05–7.14 (2H, m), 7.18 (1H, d), 7.45–7.53 (2H, m), 8.03 (1H, d). MS(MH$^+$) 246.

Methyl 2-(4-fluorophenyl)-6-methylpyridin-3-carboxylate (17.3 g) was dissolved in dichloromethane (600 ml), the solution cooled to 0° C. and MCPBA (24.3 g) added in portions over 25 minutes. The solution was then warmed to ambient temperature and stirred for 16 hours washed with saturated aqueous sodium bicarbonate (500 ml), dried and concentrated under reduced pressure. The residue was purified by flash column chromatography, eluting with methanol/ethyl acetate (1:12) to give 2-(4-fluorophenyl)-3-(methoxycarbonyl)-6-methylpyridine-1-oxide as a pale yellow oil which crystallised on standing (18.6 g).

$^1$H NMR (CDCl$_3$) δ 2.58 (3H, s), 3.62 (3H, s), 7.11–7.18 (2H, m), 7.33–7.42 (3H, m), 7.63 (1H, d). MS(MH$^+$) 261.

Methane sulfonyl chloride (7.11 ml) was added to a stirred solution of 2-(4-fluorophenyl)-3-(methoxycarbonyl)-6-methylpyridine-1-oxide (12.0 g) in toluene (300 ml) and the mixture heated at reflux under an inert atmosphere for 16 hours. The solution was partially concentrated under reduced pressure and then applied directly to a silica flash column and eluted with ethyl acetate/iso-hexane (1:5) to give methyl 2-(4-fluorophenyl)-6-chloromethylpyridin-3-carboxylate as a white crystalline solid (13.6 g).

$^1$H NMR (CDCl$_3$) δ 3.72 (3H, s), 4.72 (2H, s), 7.08–7.16 (2H, m), 7.49–7.58 (3H, m), 8.14 (1H, d). MS(MH$^+$) 280.

Sodium hydride (0.096 g) was added to a stirred solution of 1-(4-fluorophenyl)-2-(1-methylimidazol-5-yl)ethanol (0.53 g) in DMF (20 ml) under an inert atmosphere at ambient temperature. After 30 minutes the solution was cooled to −40° C. and a solution of methyl 2-(4-fluorophenyl)-6-chloromethylpyridin-3-carboxylate (0.67 g) in DMF (5 ml) added before warming to 0° C. over 90 minutes. Saturated aqueous ammonium chloride (1 ml) was added and the suspension concentrated under reduced pressure to give a yellow residue. Saturated brine (15 ml) was added and the mixture extracted with 3% methanol/dichloromethane (5×25 ml). The combined extracts were dried, and concentrated under reduced pressure. Purification by flash column chromatography eluting with methanol/dichloromethane (1:12) gave methyl 2-(4-fluorophenyl)-6-[1-(4-fluorophenyl)-2-(1-methylimidazol-5-yl)ethoxymethyl]pyrid-3-carboxylate as a yellow gum (0.30 g).

$^1$H NMR (CDCl$_3$) δ: 2.95–3.17 (2H, m), 3.38 (3H, s), 3.71 (3H, s), 4.45–4.65 (3H, m), 6.86 (2H, s), 6.97–7.16 (4H, m), 7.21–7.33 (3H, m), 7.36 (1H, s), 7.40–7.50 (2H, m), 8.09 (1H, d). MS(MH$^+$) 464.

A mixture of methyl 2-(4-fluorophenyl)-6-[1-(4-fluorophenyl)-2-(1-methylimidazol-5-yl)ethoxymethyl]pyrid-3-carboxylate (0.47 g), sodium hydroxide (0.20 g), water (6 ml) and methanol (30 ml) was heated at reflux for 3 hours and then cooled to ambient temperature. The mixture was concentrated under reduced pressure, 1M citric acid (6 ml) and water (6 ml) were added and the mixture extracted with 5% methanol/dichloromethane (3×50 ml). The extracts were dried and concentrated under reduced pressure to give 2-(4-fluorophenyl)-6-[1-(4-fluorophenyl)-2-(1-methylimidazol-5-yl)ethoxymethyl]pyrid-3-carboxylic acid as a yellow gum (0.39 g). MS(MH$^+$) 450.

EXAMPLE 58 tert-Butyl (2S)-2-{3-(4-fluorophenethyl)-6-[1-(4-fluorophenyl)-2-(1-methylimidazol-5-yl)ethoxy]pyrid-2-oylamino}-4-methylsulfanalbutyrate 3-(4-Fluorophenethyl)-6-[1-(4-fluorophenyl)-2-(1-methylimidazol-5-yl)ethoxy]pyridin-2-carboxylic acid (0.61 g) and L-methionine-tert-butyl-ester.HCl (0.64 g) were dissolved in dichloromethane (50 ml) then DMAP (0.96 g) and EDC (0.38 g) were added under an inert atmosphere at ambient temperature. After stirring for 16 hours the solution was washed with 1M citric acid (60 ml) and the organic layer dried and concentrated under reduced pressure. Purification on a silica flash column eluting with ethyl acetate gave tert-butyl (2S)-2-{3-(4-fluorophenethyl)-6-[1-4-fluorophenyl)-2-(1-methylimidazol-5-yl)ethoxy]pyrid-2-oylamino}-4-methylsulfanylbutyrate as a colourless foam (0.27 g).

$^1$H NMR (CDCl$_3$) δ: 1.54 (9H, d), 1.75–1.98 (2H, m), 2.05 (3H, s), 2.12–2.29 (1H, m), 2.33–2.63 (1H, m), 2.76–2.88 (2H, m), 3.06–3.30 (4H, m), 3.42 (3H, s), 4.63–4.73 (1H, m), 6.05–6.21 (1H, m), 6.76–7.03 (5H, m), 7.06–7.16 (2H, m), 7.26–7.42 (4H, m), 8.06–8.14 (1H, m). Anal. Calculated allowing for 1.5 HCl: C, 59.6; H, 5.9; N, 7.9. Found: C, 59.8; H, 5.9; N, 7.7; MS(MH$^+$) 651.

The starting material was prepared as follows:
Methyl 3-(trifluoromethanesulfonyloxy)pyridin-2-carboxylate was prepared in two steps from 2-hydroxypicolinic acid using the procedure of Subramanyam, C.; Chattarjee, S.; Mallamo, J. P. Tetrahedron Len., 1996, 37, 459.
Methyl 3-hydroxypyridin-2carboxylate:

$^1$H NMR (CDCl$_3$) δ: 4.08 (3H, s), 7.40 (2H, m), 8.28 (1H, dd). MS(MH$^+$) 154.
Methyl 3-(trifluoromethanesulfonyloxy)pyridin-2-carboxylate:

$^1$H NMR (CDCl$_3$) δ: 4.07 (3H, s), 7.61 (1H, dd), 7.74 (1H, dd), 8.76 (1H, d). MS(MH$^+$) 286.
Tributylamine (24.6 ml) was added to a stirred mixture of methyl 3-(trifluoromethanesulfonyloxy)pyridin-2-carboxylate (19.6 g), bis (triortho-tolylphosphine)palladium (II) chloride (1.08 g), copper (I) iodide (0.1 3 g) and 4-fluorostyrene (12.3 ml) in DMF (300 ml). The solution was heated under an inert atmosphere at 90° C. for 26 hours then cooled to ambient temperature and concentrated under reduced pressure. The residue was dissolved in dichloromethane (300 ml), the solid filtered and the filtrate washed with 1M. citric acid (3×100 ml), saturated aqueous sodium bicarbonate (150 ml), dried and concentrated under reduced pressure. The brown oil obtained was pre-absorbed onto silica then purified on a silica flash column eluting with ethyl acetate/iso-hexane (4:6) to give methyl 3-[2-(4-fluorophenyl)ethenyl]pyridin-2-carboxylate as a pale yellow solid (12.4 g).

$^1$H NMR (CDCl$_3$) δ:4.02 (3H, s), 7.01 (1H, d), 7.04–7.11 (2H, m), 7.46 (1H, dd), 7.49–7.56 (2H, m), 7.83 (1H, d), 8.05 (1H, d), 8.59 (1H, d). MS(MH$^+$) 258.

A suspension of 10% palladium on carbon (2.5 g) and methyl 3-[2-(4-fluorophenyl)ethenyl]pyridin-2-carboxylate (12.4 g) in ethyl acetate (200 ml) was stirred vigorously under an hydrogen atmosphere at ambient temperature for four hours. The suspension was filtered through Celite and the filtrate concentrated under reduced pressure to give methyl 3-(4-fluoropbenethyl)pyridin-2-carboxylate as a mobile, pale yellow oil (11.72 g).
NMR data (CDCl$_3$) δ 2.89 (2H, dd), 3.21 (2H, dd), 3.97 (3H, s), 6.89–7.00 (2H, m), 7.06–7.16 (2H, m), 7.33 (1H, dd), 7.49 (1H, d), 8.58 (1H, dd). MS(MH$^+$) 260.

Methyl 3-(4-fluorophenethylpyridin-2-carboxylate (11.7 g) was dissolved in dichloromethane (600 ml), cooled to 0° C. and MCPBA (14.7 g) added in portions over 20 minutes. The solution was then warmed to ambient temperature and stirred for 16 hours. The mixture was washed with saturated aqueous sodium bicarbonate (2×200 ml), dried and then concentrated under reduced pressure. The residue was purified on a silica flash column eluting with mehanol/dichloromethane (1:12) to give 3-(4-fluorophenethyl-2-(methoxycarbonyl)pyridine-1-oxide as a pale yellow oil which was crystallised from diethyl ether (10.5 g).

$^1$H NMR (CDCl$_3$) δ 2.77–2.92 (4H, m), 4.03 (3H, s), 6.91–7.01 (3H, m), 7.03–7.09 (2H, m), 7.16 (1H, d), 8.14 (1H, d). MS(MH$^+$) 276.

A solution of 3-(4-fluorophenethyl)-2-(methoxycarbonyl)pyridine-1-oxide (7.96 g) in DMF (100 ml) and trifluoroacetic anhydride (40.9 ml) was stirred under an inert atmosphere at ambient temperature for 24 hours. The reaction mixture was concentrated under reduced pressure, diluted with saturated aqueous sodium bicarbonate (150 ml) and extracted with dichloromethane (3×100 ml). The combined organic extracts were dried and concentrated under reduced pressure and the residue purified on a silica flash column eluting with methanol/dichloromethane (1:9) to give methyl 3-(4-fluorophenethyl)-6-hydroxypyridin-2-carboxylate as a cream solid (7.7 g).

$^1$H NMR (CDCl$_3$) δ 2.80 (2H, dd), 3.08 (2H, dd), 3.95 (3H, s), 6.71 (1H, d), 6.92–7.01 (2H, m), 7.06–7.11 (2H, m), 7.28 (1H, d), 9.63 (1H, br. s). MS(MH$^+$) 276.

DEAD (0.85 ml) was added dropwise over 2 minutes to a stirred suspension of methyl 3-(4-fluorophenethyl)-6-hydroxypyridin-2-carboxylate (1.0 g), 2-(1-methylimidazol-5-yl)-1-(4-fluorophenyl)ethanol (0.80 g) and triphenylphosphine (1.43 g) in THF (70 ml) under an inert atmosphere at ambient temperature. After stirring for 16 hours the solution was concentrated under reduced pressure and loaded directly onto a silica flash column eluting with methanol/dichloromethane (1:20) to give methyl 3-(4-fluorophenethyl)-6-[1-(4-fluorophenyl)-2-(1-methylimidazol-5-yl)ethoxy]pyridin-2-carboxylate as a colourless oil (1.56 g).

$^1$H NMR (CDCl$_3$) δ: 2.81 (2H, dd), 3.01–3.12 (3H, m), 3.35 (1H, dd), 3.91 (3H, s), 6.21 (1H, t), 6.68–6.81 (2H, m), 6.87–7.20 (5H, m), 7.26–7.37 (3H, m), 7.40–7.45 (1H, m). MS(MH$^+$) 478.

A mixture of methyl 3-(4-fluorophenethyl)-6-[1-(4-fluorophenyl)-2-(1-methylimidazol-5-yl)ethoxy]pyridin-2-carboxylate (1.56 g), sodium hydroxide (0.65 g), water (12 ml) and methanol (80 ml) was heated at reflux for 16 hours and then cooled to ambient temperature. The mixture was concentrated under reduced pressure, 1M citric acid (17 ml) added and the mixture extracted with 10% methanol/dichloromethane (1×50 ml, 2×30 ml). The extracts were dried and concentrated under reduced pressure to give 3-(4-fluorophenethyl)-6-[1-(4-fluorophenyl)-2-(1-methylimidazol-5-yl)ethoxy]pyridin-2-carboxylic acid as a pale yellow foam (1.22 g).

EXAMPLE 59

Cyclopentyl (2S)-2-{3-(4-fluorophenethyl)-6-[1-(4-fluorophenyl)-2-(1-methylimidazol-5-yl)ethoxy]pyrid-2-oylamino}-4-methylsulfanylbutyrate The title compound was prepared from 3-(4-fluorophenethyl)-6-[1-(4-fluorophenyl)-2-(1-methylimidazol-5-yl)ethoxy]pyridin-2-carboxylic acid by a similar route to that described for the preparation of tert-butyl (2S)-2-{3-(4-fluorophenethyl)-6-[1-(4-fluorophenyl)-2-(1-methylimidazol-5-yl)ethoxy]pyrid-2-oylamino}-4-methylsulfanylbutyrate but using L-methionine cyclopentyl ester rather than L-methionine-tert-butyl ester.

$^1$H NMR (CDCl$_3$) δ: 1.58–1.81 (7H, m), 1.84–1.99 (3H, m), 2.03–2.16 (1H, m) overlapping 2.07 (3H, d), 2.17–2.43 (3H, m), 2.58 (1H, m), 2.81 (2H, m), 3.08–3.37 (4H, m), 3.39 (3H, s), 4.64–4.78 (1H, m), 5.28 (1H, m), 6.05–6.18 (1H, m), 6.76–7.03 (6H, m), 7.11 (2H, m), 7.34 (3H, m), 8.10 (1H, m). Anal. Calculated allowing for 0.5 H$_2$O: C, 64.4; H, 6.1; N, 8.3. Found: C, 64.4; H, 6.1 N, 8.2; MS(MH$^+$) 663.

The starting material was prepared as follows:

A mixture of N-tert-butoxycarbonyl L-methionine (30 g.), cyclopentanol (31 g.), DMAP (44 g.), EDC (30 g.) and dichloromethane (200 ml.) was stirred under an inert atmosphere for 16 hours. It was then washed with 1M. aqueous citric acid (200 ml.), saturated sodium carbonate solution (100 ml.) and brine, dried and evaporated to dryness to give N-tert-butoxycarbonyl L-methionine cyclopentyl ester as a gum(36 g.).

$^1$H NMR(CDCl$_3$) δ: 1.44(9H, s), 1.52–2.0(9H, m), 2.0–2.2(1H, m), 2.1(3H, s), 2.54(2H, m), 4.34(1H, m), 5.1(1H, br.s), 5.2(1H, m). MS(MH$^+$) 318.

A mixture of N-tert-butoxycarbonyl L-methionine cyclopentyl ester (53 g.), TFA (200 ml.), triethylsilane (39 g.) and dichloromethane (2 L.) was stirred at ambient temperature for 2 hours, evaporated to dryness and then converted to the hydrochloride salt to give L-methionine cyclopentyl ester as a white crystalline solid (40.5 g.).

$^1$H NMR(DMSO-d$_6$) δ: 1.47–1.95(8H, m), 1.95–2.2(2H, m), 2.05(3H, s), 2.45–2.75(2H, m), 4.0(1H, t), 5.18(1H, m), 8.7(3H, br.s). MS(MH$^+$) 218.

EXAMPLE 60

(2S)-2-{2-(4-Fluorophenethyl)-5-[1-(thiazol-2-yl)-2-(1-methylimidazol-5-yl)ethoxy]benzoylamino}-4-methylsulfanylbutyric acid A mixture of tert-butyl (2S)-2-{2-(4-fluorophenethyl)-5-[1-(thiazol-2-yl)-2-(1-methylimidazol-5-yl)ethoxy]benzoylamino}-4-methylsulfanylbutyrate (0.050 g, 0.078 mmol) in TFA was stirred at ambient temperature under a nitrogen atmosphere for 4 hours. The TFA was evaporated away and the residues basified with saturated sodium bicarbonate solution, reacidified with 2NHCl to pH6 and extracted with dichloromethane. The extracts were dried and evaporated to dryness. The residue was dried under high vacuum to give the title compound as a white solid (0.040 g, 89%).

$^1$H NMR (CDCl$_3$+DMSO-d$_6$) δ: 2.05–2.15 (5H, m), 2.15–2.20 (1H, m), 2.20–2.30 (1H, m), 2.59–2.68 (2H, m), 2.81–2.90 (2H, d), 2.95–3.03 (2H, d), 3.50–3.61 (2H, m), 3.86–3.95 (3H, s), 4.73–4.83 (1H, m), 5.90–6.01 (1H, m), 6.83–6.96 (3H, m), 7.01–7.17 (4H, m), 7.18–7.28 (1H, m), 7.35–7.47 (3H, m), 7.83–7.87 (1H, s), 9.08–9.13 (1H, m). Anal. Calculated allowing for 5.5 HCl: C, 44.47; H, 4.70; N, 7.15; S, 8.19; Found: C, 44.40; H, 4.70; N, 7.10; S, 7.80; MS (MH$^+$). 583.3.

The starting material was prepared as follows:

A mixture of 2-thiazole carboxaldehyde (25 g, 221 mmol), triethylorthoformate (46 mls, 41 g, 276 mmol) and para-toluenesulphonic acid (1.52 g, 9 mmol) in ethanol (200 ml) was sured for 16 hours under a nitrogen atmosphere at ambient temperature. A further amount of para-toluenesulphonic acid (2 g, 11 mmol) was added and the reaction stirred for another 16 hours. The mixture was treated with sodium bicarbonate to pH 9, stirred for a further 5 minutes and then filtered and the filtrate evaporated to dryness to give 2-(1,1-diethoxymethyl)thiazole as a clear oil, which was used without flirher purification (41 g, 99%).

$^1$H NMR (CDCl$_3$) δ: 1.28 (6H, t), 3.60–3.80 (4H, m), 5.74 (1H, s), 7.34 (1H, d), 7.80 (1H, d). MS (MH$^+$). 187.4.

Boron trifluoride etherate (21 g, 18 ml, 148 mmol) was added dropwise to a mixture of 2-(1,1-diethoxymethyl) thiazole (27.6 g 148 mmol) and triethyl phosphite (24.5 g, 25 mls, 148 mmol) in dichloromethane (300 ml) and the mixture refluxed for 12 hours under a nitrogen atmosphere. The reaction was allowed to cool to ambient temperature, treated with water (100 ml) and stirred for a further 10 minutes. The organic phase was separated, dried, filtered and evaporated to dryness. Purification by flash column chromatography eluting with ethyl acetate and ethyl acetate/methanol (9:1 and 4:1) gave diethyl ethoxy(1,3-thiazol-2-yl)methyl phosphonate as a brown oil, (7 g, 30%).

$^1$H NMR (CDCl$_3$) δ:1.23–1.36(9H, m), 3.65–3.73 (2H, m), 4.07–4.30 (4H, m), 5.05 (1H, d), 7.42 (1H, d), 7.80 (1H, d). MS (MH$^+$). 280.2.

A solution of n-butyl lithium (1.6M in hexane) (30 ml, 47 mmol) was added dropwise over 5 minutes to a solution of diethyl ethoxy(1,3-thiazol-2-yl)methyl phosphonate (15.21 g, 55 mmol) in tetrahydofaran (400 ml) cooled to −78° C. under a nitrogen atmosphere and the mixture was then stirred for a further 10 minutes. A solution of 1-methyl-1H-imidazole-5-carboxaldehyde (4) (4 g, 36 mmol) in tetrahydrofuran (20 ml) was then added over 10 minutes to the reaction which was then stirred for a further 20 minutes, after the addition was completed. The reaction was treated with water (50 ml), allowed to warm to ambient temperature, acidified with hydrochloric acid (10N, 50 ml) and refluxed for 18 hours under a nitrogen atmosphere. The reaction was cooled to ambient temperature, basified with saturated aqueous sodium bicarbonate to pH 8, the tetrahydrofuran evaporated and the aqueous residues extracted with ethyl acetate (2×250 ml). The combined organic extracts were washed with brine, dried and evaporated to dryness. Pification by column flash column chromatography eluting with ethyl acetate/methanol (9:1 and 4:1) gave 2-(1-methylimidazol-5-yl)-1-(thiazol-2-yl)thanone as a yellow solid, (7.3 g, 907%).

¹H NMR (CDCl₃) δ: 3.65 (3H, s), 4.48 (2H, s), 7.00 (1H, s), 7.45 (1H, s), 7.73 (1H, s), 8.05 (1H, s). MS (MH⁺). 208.

Sodium borohydride (0.56 g, 14.9 mmol) was added to a solution of 2-(1-methylimidazol-5-yl)-1-(thiazol-2-yl)ethanone in methanol (150 ml) and the mixture stirred under a nitrogen atmosphere at ambient temperature for 2 hours. The reaction was evaporated to dryness and the resulting gum was treated with water (15 ml) and stirred for 30 minutes to give a solid precipitate which was filtered and dried to give 2-(1-methylimidazol-5-yl)-1-(thiazol-2-yl)ethanol (2.67 g, 95%).

¹H NMR (CDCl₃) δ: 2.88–2.99 (1H, q), 3.11–3.20 (1H, dd), 3.28 (2H, s), 3.51 (3H, s), 4.96–5.04 (1H, m), 6.36 (1H, s), 6.59 (1H, s), 7.60 (1H, d), 7.73 (1H, s). MS (MH⁺). 210.3.

A mixture of methyl 2-(4-fluorophenethyl)-5-hydroxybenzoate (1.83 g, 6.7 mmol), 2-(1-methylimidazol-5-yl)-1-(thiazol-2-yl)ethanol (1.40 g, 6.68 mmol) and triphenylphosphine (2.10 g, 8.0 mmol) in tetrahydrofuran (25 ml) was stirred at ambient temperature under a nitrogen atmosphere. DEAD (1.39 g, 1.25 ml 8.0 mmol) was added dropwise to the solution. (The reaction was maintained at ambient temperature ±2° C.). The orange solution was then stirred at ambient temperature under a nitrogen atmosphere for 16 hours. The tetrahydrofuran solution was evaporated to dryness to give an oil. Purification by flash column chromatography eluting with ethyl acetate, ethyl acetate/methanol (9:1 and 4:1) gave methyl 2-(4-fluorophenethyl)-5-[2-(1-methylimidazol-5-yl)-1-(thiazol-2-yl)ethoxy]benzoate (2.07 g, 67%) as a clear oil.

¹H NMR (CDCl₃) δ: 2.76 (2H, t), 3.10 (2H, t), 3.30–3.45 (2H, m), 3.60 (3H, s), 5.70–5.75 (1H, m), 6.90–7.50 (10 H, m), 7.77 (1H, d). MS (MH⁺). 466.4.

A mixture of methyl 2-(4-fluorophenethyl)-5-[2-(1-methylimidazol-5-yl)-1-(thiazol-2-yl)ethoxy]benzoate (2.07 g, 4.4 mmol) and sodium hydroxide (0.89 g, 22.23 mmol) in methanol (100 ml) and water (9 ml) was stirred under a nitrogen atmosphere at reflux for 18 hours, cooled to ambient temperature and the methanol evaporated off. The residue was treated with aqueous citric acid (1M, 40 ml) and extracted with dichloromethane. The organic extracts were dried and evaporated to dryness to give 2-(4-fluorophenethyl)-5-[2-(1-methylimidazol-5-yl)-1-(thiazol-2-yl)ethoxy]benzoic acid as a white foam, (1.48 g, 75%).

¹H NMR (CDCl₃) δ: 2.83 (2H, t), 3.20 (2H, t), 3.27–3.53 (2H, m),3.56 (3H, s),4.30–4.60 (1H, br), 5.70–5.80 (1H, m), 6.83–7.16 (7H, m), 7.30–7.66 (3H, m), 7.80 (1H, d). MS (MH⁺). 452.4.

A mixture of 2-(4-fluorophenethyl)-5-[2-(1-methylimidazol-5-yl)-1-(thiazol-2-yl)ethoxy]benzoic acid (0.74 g, 1.63 mmol), DMAP (1.0 g, 8.2 mmol), L-methionine tert-butyl ester HCl (1.0 g, 4.92 mmol), EDC (0.63 g, 3.27 mmol) and HOBT (0.22 g, 1.63 mmol) in DMF (50 ml) was stirred at ambient temperature under a nitrogen atmosphere for 16 hours. The reaction was evaporated to dryness and washed with aqueous citric acid (1M, 20 ml) and extracted with dichloromethane (20 ml). The extracts were washed with saturated brine and dried and applied directly onto a silica flash column which was eluted with ethyl acetate/methanol (9:1 and 4:1) to give tert-butyl (2S)-2- {2-(4-fluorophenethyl)-5-[1-(thiazol-2-yl)-2-(1-methylimidazol-5-yl)ethoxy]benzoylamino}-4-methylsulfanylbutyrate. The product was dissolved in ethyl acetate and treated with 1M ethereal HCl (10 ml). The resulting solid was isolated by centrifuging, flirther washing with diethyl ether and finally drying under high vacuum to give tert-butyl (2S)-2-{2-(4-fluorophenethyl)-5-[1-(thiazol-2-yl)-2-(1-methylimidazol-5-yl)ethoxy]benzoylamino}-4-methylsulfanylbutyrate as a white solid, (0.57 g, 54% Yield.

¹H NMR (CDCl₃) δ: 1.45–1.53 (9H, s), 1.99–2.10 (1H, m), 2.08 (3H, s), 2.16–2.31 (1H, m), 2.51–2.63 (2H, t), 2.78–2.97 (2H, m), 2.92–3.00 (2H, m), 3.30–3.4 (2H, m), 3.57 (3H, s), 4.66–4.78 (1H, m), 5.68–5.73 (1H, m), 6.47–6.55 (1H, t), 6.77–7.13 (8H, m), 7.40–7.45 (2H, m), 7.80 (1H, d). Anal. Calculated allowing for: 2 HCl 2H₂O C, 53.00; H, 6.07; N, 7.49; S, 8.58; Found: C, 53.00; H, 6.20; N, 7.00; S, 8.70; MS (MH⁺). 439.4.

EXAMPLE 61

(2S)-2-{2-(4-Fluorophenethyl)-5-[1-(thiazol-2-yl)-2-(1-methylimidazol-5-yl)ethoxy]benzoylamino}-4-methylsulfonylbutyric acid (2S)-2-{2-(4-Fluorophenethyl)-5-[1-(thiazol-2-yl)-2-(1-methylimidazol-5-yl)ethoxy]benzoylamino}-4-methylsulfonylbutyric acid was prepared from tert-butyl (2S)-2-{2-(4-fluorophenethyl)-5-[1-(thiazol-2-yl)-2-(1-methylimidazol-5-yl)ethoxy]benzoylamino}-4-methylsulfonylbutyrate by a similar method to that used for Example 60.

¹H NMR (CDCl₃+DMSO-d₆) δ: 2.48–2.56 (1H, m), 2.78–2.99 (2H, m), 2.92–3.03 (4H, m), 3.25–3.34 (1H, m), 3.51–3.60 (1H, m), 3.88–3.97 (3H, s), 5.93–6.05 (1H, m), 6.05–6.15 (1H, m), 6.88–6.98 (3H, m), 7.03–7.18 (3H, m), 7.25–7.54 (3H, m), 7.68–7.95 (2H, m), 8.93–9.04 (1H, m). Anal. Calculated allowing for 1 H₂O, 4 HCl : C, 44.73; H, 4.79; N, 7.20; S, 8.2; Found: C, 44.90; H, 5.00; N, 6.80; S, 7.00; MS (MH⁺). 615.3.

The starting material was prepared as follows:

A mixture of 2-(4-fluorophenethyl)-5-[2-(1-methylimidazol-5-yl)-1-(thiazol-2-yl)ethoxy]benzoic acid (0.74 g, 1.63 mmol), DMAP (1.40 g, 11.5 mmol), L-methionine sulphone tert-butyl ester HCl (1.34 g, 4.92 mmol), EDC (0.63 g, 3.27 mmol) and HOBT (0.22 g, 1.63 mmol) in DMF (50 ml) was stirred at ambient temperature under a nitrogen atmosphere for 16 hours. The reaction was evaporated to dryness and washed with aqueous citric acid (1M, 20 ml) and extracted with dichloromethane (20 ml). The extracts were washed with saturated brine, dried and evaporated to dryness. Purification by flash column chromatography eluting with dichloromethane/methanol (95:5, 9:1/85:15) gave a gum. This was redissolved in ethyl acetate and treated with 1M ethereal HCl (10 ml). The resulting solid precipitate was isolated by centrifuging, further washing with diethyl ether and drying under high vacuum to give tert-butyl (2S)-2-{2-(4-fluorophenethyl)-5-[1-(thiazol-2-yl)-2-(1-methylimidazol-5-yl)ethoxy]benzoylamino}-4-methylsulfonylbutyrate as a white solid, (0.66 g, 60% Yield).

¹H NMR (CDCl₃) δ: 1.51(9H, s), 2.22–2.38 (1H, m), 2.46–2.61 (1H, m), 2.77–2.88 (2H, m), 2.92 (3H, s), 2.92–3.04 (2H, m), 3.08–3.42 (6H, m), 3.58 (3H, s), 4.65–4.77 (1H, m), 5.66–5.73 (1H, m), 6.77–7.13 (11H, m), 7.25–7.35 (3H, m), 7.42–7.51 (1H, m), 7.76–7.83 (1H, m). Anal. Calculated allowing for 2 HCl : C, 53.29; H, 5.56; N, 7.53; S, 8.62; Found: C, 53.00; H, 5.60; N, 8.10; S, 7.80; MS (MH⁺). 671.4.

EXAMPLE 62 tert-Butyl (2S)-2-{2-(4-fluorophenethyl)-[1-(thiazol-2-yl)-2-(1-methylimidazol-5-yl)ethoxymethyl]benzoylamino}-4-methblsulfanylbutyrate A mixture of 2-(4-fluorophenethyl)-5-[1-(thiazol-2-yl)-2-(1-methylimidazol-5-yl)ethoxymethyl]benzoic acid (0.47 g, 1.06 mmol) (from Example 63), DMAP (0.62 g, 5.05 mmol), L-methionine tert-butyl ester HCl (0.62 g, 3.02 mmol), EDC (0.39 g, 2.02 mmol) and HOBT (0.137 g, 1.01 mmol) in DMF (25 ml) was stirred at ambient temperature under a nitrogen atmosphere for 16 hours. The reaction was evaporated to dryness and washed with aqueous citric acid (1M, 10 ml) and extracted with dichloromethane (20 ml). The extracts were washed with saturated brine, dried and filtered. Purification by flash column chromatography eluting with dichloromethanel methanol (95:5, 9:1 and 85:15) gave a gum. This was dissolved in ethyl acetate and treated with 1M ethereal HCl (10 ml). The resulting solid precipitate was isolated by centrifuging, further washing with diethyl ether and drying under high vacuum to give tert-butyl (2S)-2-(2-(4-fluorophenethyl)-5-[1-(thiazol-2-yl)-2-(1-methylimidazol-5-yl)ethoxymethyl]benzoylamino}-4-methylsulfanylbutyrate as a white solid, (0.366 g, 55%).

$^1$H NMR (CDCl$_3$) δ: 1.51(9H, s), 1.92–2.08 (1H, m), 2.15–2.33 (1H, m), 2.59–2.70 (2H, m), 2.85–2.98 (5H, m), 3.00–3.23 (4H, m), 3.46 (3H, d), 4.34 (1H, d), 4.52 (1H, dd), 4.70–4.83 (1H, m), 4.83–4.90 (1H, m), 6.77 (1H, d), 6.99–7.08 (3H, m), 7.12–7.21 (5H, m), 7.38 (1H, d), 7.80 (1H, d). Anal. Calculated allowing for: 2.75 H$_2$O,1 HCl C, 55.27; H, 6.48; N, 7.58; S, 8.68; Found: C, 55.00; H, 6.70; N, 7.50; S, 9.00; MS (MH$^+$). 653.4.

EXAMPLE 63 tert-Butyl (2S)-2-{2-(4-fluorophenethyl)-5-[1-(thiazol-2-yl)-2-(1-methylimidazol-5-yl) ethoxymethyl]benzoylamino}-4-methslsulfonylbutyrate A mixture of 2-(4-fluorophenethyl)-5-[1-(thiazol-2-yl)-2-(1-methylimidazol-5-yl)ethoxymethyl]benzoic acid (0.47 g, 1.01 mmol), DMAP (0.86 g, 7.07 mmol), L-methionine sulphone tert-butyl ester HCl (0.83 g, 3.03 mmol), EDC (0.39 g, 2.02 mmol) and HOBT (0.138 g, 1.01 mmol) in DMF (25 ml) was stirred at ambient temperature under a nitrogen atmosphere for 16 hours. The reaction was evaporated to dryness and washed with aqueous citric acid (1M, 10 ml) and extracted with dichloromethane (20 ml). The extracts were washed with saturated brine and dried. Purification by flash column chromatography eluting with dichloromethane/methanol (95:5, 9:1 and 85:15) gave a gum. This was dissolved in ethyl acetate and treated with ethereal HCl (10 ml). The resulting solid precipitate was isolated by centrifuging, further washing with diethyl ether and drying under high vacuum to give tert-butyl (2S)-2-{2-(4-fluorophenethyl)-5-[1-(thiazol-2-yl)-2-(-methylimidazol-5-yl)ethoxymethyl]benzoylamino}-4-metbylsulfonylbutyrate as a white solid, (0.506 g, 73%).

$^1$H NMR (CDCl$_3$) δ: 1.51 (9H, s), 2.30–2.65 (2H, m), 2.87–3.43 (7H, m), 2.94 (3H, s), 3.45 (3H, s), 4.30 (1H, d), 4.65(1H, dd), 4.70–4.87 (2H, m), 6.73 (1H, d), 6.89–7.02 (2H, m), 7.10–7.20 (4H, m), 7.25 (2H, d), 7.34–7.55 (2H, m), 7.83 (1H, d). Anal. Calculated ailowing for 2 H$_2$O, 1.5 HCl: C, 52.65; H, 6.04; N, 7.22; S, 8.27; Found: C, 53.00; H, 6.30; N, 7.20; S, 8.30; MS (MH$^+$). 685.4.

The starting material was synthesised as follows:

Sodiumn hydride, 60% dispersion in mineral oil (0.44 g, 11 mmol) was washed with iso-hexane and was suspended in DMF (25 ml). A solution of2-(1-methylimidazol-5-yl)-1-(thiazol-2-yl)ethanol (2.10 g, 10 mmol) in DMF (75 ml) was added dropwise and the mixture stirred under a nitrogen atmosphere at ambient temperature for 10 minutes. A solution of methyl 5-bromomethyl-2-(4-fluorophenethyl) benzoate (3.51 g, 10 mmol) in DMF (50 ml) was added dropwise to the reaction followed by tetrabutylammonium iodide (0.37 g, 1 mmol) and the mixture was then stirred at ambient temperature for 16 hours. The reaction was evaporated to dryness and the residue treated with water (100 ml) and extracted with dichloromethane (100 ml). The extracts were washed with saturated brine dried and evaporated to dryness. Purification by flash column chromatography eluting with dichloromehiane/methanol (95:5 and 9:1) gave methyl 2-(4-fluorophenethyl)-5-[1-(thiazol-2-yl)-2-(1-methylimidazol-5-yl)ethoxymethyl]benzoate as a yellow gum, (3.32 g, 69%).

$^1$H NMR (CDCl$_3$) δ: 2.85 (2H, t), 3.12–3.30 (4H, m), 3.50 (3H, s), 3.93 (3H, s), 4.45 (1H, d), 4.62 (1H, d), 4.90–4.97 (1H, m),6.87 (1H, s), 6.95–7.05 (3H, m), 7.13 (3H, m), 7.40 (2H, d), 7.80 (2H, m). MS (MH$^+$). 480.4.

A mixture of methyl 2-(4-fluorophenethyl)-5-[1-(thiazol-2-yl)-2-(1-methylimidazol-5-yl)ethoxymethyl]benzoate (3.32 g, 6.92 mmol), sodium hydroxide (1.38 g, 34.61 mmol) in methanol (150 ml) and water (15 ml) was stirred under a nitrogen atmosphere at reflux for 18 hours, cooled to ambient temperature and the methanol evaporated off. The residue was treated with aqueous citric acid (1M, 40 ml) and extracted with dichloromethane. The organic extracts were dried and evaporated to dryness to give 2-(4-fluorophenethyl)-5-[1-(thiazol-2-yl)-2-(1-methylimidazol-5-yl)ethoxymethyl]benzoic acid as a yellow foam (2.85, 88%).

$^1$H NMR (CDCl$_3$) δ: 2.85–2.98 (2H, m), 3.04–3.34 (4H, m), 3.53 (3H, s), 4.34 (1H, d), 4.72 (1H, d), 4.89 (1H, dd), 6.95–7.05 (2H, m), 7.04–7.22 (4H, m), 7.33–7.45 (2H, m), 7.57 (1H, s), 7.83 (2H, d), 8.00 (1H, br). MS (MH$^+$). 466.4.

EXAMPLE 64 tert-Butyl (2S)-2-{2-(4-fluorophenyl)-4-[1-(thiazol-2-yl)-2-(1-methylimidazol-5-yl)ethoxymethyl] benzoylamino}-4-methylsulfanylbutyrate A mixture of 2-(4-fluorophenyl)-4-[1-(thiazol-2-yl)-2-(1-methylimidazol-5-yl)ethoxymethyl]benzoic acid (0.44 g, 1.07 mmol) (from Example 65), DMAP (0.62 g, 5.03 mmol), L-methionine tert-butyl ester HCl (0.62 g, 5.03 mmol), EDC (0.39 g, 2.01 mmol) and HOBT (0.138 g, 1.01 mmol) in DMF (25 ml) was stirred at ambient temperature under a nitrogen atmosphere for 16 hours. The reaction was evaporated to dryness, the residue treated with aqueous citric acid (1M, 10 ml) and then extracted with dichloromethane (20 ml). The extracts were washed with saturated brine, dried and applied directly to a silica flash column eluting with dichloromethane/methanol (95:5, 9:1 and 85:15) to give a gum. This was dissolved in ethyl acetate and treated with ethereal 1M HCl (10 ml). The resulting solid was isolated by centrifuging, further washing with diethyl ether and drying under high vacuum to give tert-butyl (2S)-2-{2-(4-fluorophenyl)-4-[1-(thiazol-2-yl)-2-(1-methylimidazol-5-yl)ethoxymethyl]benzoylamino}-4-methylsulfanylbutyrate as a white solid, (0.373 g, 59%).

$^1$H NMR (DMSO-d$_6$) δ: 1.49 (9H, s), 1.80–2.00 (2H, m), 2.06 (3H, s), 2.20–2.40 (2H, m), 3.13–3.31 (4H, m), 4.22–4.32 (1H, m), 4.70 (2H, q), 5.11 (1H, q), 6.63 (1H, s), 7.20–7.30 (2H, m), 7.30–7.51(7H, m), 7.80 (1H, d), 7.80 (1H, d), 7.89 (1H, d), 8.53 (1H, d). Anal. Calculated allowing for: 1.5 H$_2$O, 1.5 HCl C, 54.40; H, 5.92; N, 7.93; S, 9.08; Found: C, 54.40; H, 6.00; N, 7.80; S, 9.00; MS (MH$^+$). 625.4.

EXAMPLE 65 tert-Butyl (2S)-2-{2-(4-fluorophenyl)-[1-(thiazol-2-yl)-2-(1-methylimidazol-5-yl)ethoxymethyl] benzoylamino}-4-methylsulfonylbutyrate A mixture of 2-(4-fluorophenyl)-4-[1-(thiazol-2-yl)-2-(1-methylimidazol-5-yl)ethoxymethyl]benzoic acid (0.44 g, 1.07 mmol), DMAP (0.61 g, 5.04 mmol), L-methionine tert-butyl ester HCl (0.71 g, 3.03 mmol), EDC (0.39 g, 2.01 mmol) and HOBT (0.138 g, 1.01 mmol) in DMF (25 ml) was stirred at ambient temperature under a nitrogen atmosphere for 16 hours. The reaction was evaporated to dryness and washed with aqueous citric acid (1M, ml) and extracted with dichloromethane (20 ml). The extracts were washed with saturated brine, dried and filtered. Purification by flash column chromatography eluting with dichloromethane/methanol (95:5, 9:1 and 85:15) gave a gum. This was dissolved in ethyl acetate and treated with ethereal 1M HCl (10 ml). The resulting solid was isolated by centrifuging, further washing with diethyl ether and drying under high vacuum to give tert-butyl (2S)-2-{2-(4-fluorophenyl)-4-[1-(thiazol-2-yl)-2-(1-methylimidazol-5-yl)ethoxymethyl]benzoylamino}-4-methylsulfonylbutyrate as a white solid, (0.406 g, 62%).

$^1$H NMR (DMSO-$d_6$) δ: 1.40 (9H, s),1.82–2.02 (1H, m), 2.02–2.12 (1H, m), 2.73–2.89 (1H, m), 2.93 (3H, s), 2.95–3.10 (2H, m), 3.10–3.25 (2H, m), 3.45 (3H, s), 4.18 4.28 (1H, m),4.63 (2H, q), 5.02 (1H, q0, 6.60 (1H, s), 7.10–7.25 (2H, m),7.25–7.50 (7H, m), 7.71 (1H, d), 7.81 (1H, d), 8.79 (1H, d). Anal. Calculated allowing for 1.5 HCl, 1.5 H$_2$O: C, 52.04; H, 5.66; N, 7.59; S, 8.68; Found: C, 51.90; H, 5.40; N, 7.40; S, 8.70; MS (MH$^+$). 657.4.

The starting material was prepared as follows:

Sodium hydride 60% dispersion in mineral oil (0.17 g, 4.34 mmol) was washed with iso-hexane and was suspended in DMF (25 ml). A solution of 2-(1-methylimidazol-5-yl)-1-(thiazol-2-yl)ethanol (0.83 g, 3.94 mmol) in DMF (30 ml) was added dropwise and the mixture stirred under a nitrogen atmosphere at ambient temperature for 10 minutes. A solution of methyl 4-bromomethyl-2-(4-fluorophenyl)benzoate (1.28 g, 3.94 mmol) in DMF (25 mL) was added dropwise to the reaction followed by tetra butyl ammonium iodide (0.15 g, 0.394 mmol) and the mixture was then stirred under a nitrogen atmosphere at ambient temperature for 16 hours. The reaction was evaporated to dryness, the residue treated with water (20 ml) and extracted with dichloromethane (50 ml). The extracts were washed with saturated brine, dried and filtered. Purification by flash column chromatography, eluting with dichloromethane/methanol (95:5 and 9:1) gave methyl 4-[1-(thiazol-2-yl)-2-(1-methylimidazol-5-yl)ethoxymethyl]-2-(4-fluorophenyl)benzoate (1.45 g, 82%) as a yellow gum.

$^1$H NMR (CDCl$_3$) δ: 3.10–3.25 (2H, m), 3.49 (3H, s), 3.66 (3H, s), 4.50 (1d), 4.98 (1H, q), 6.86 (1H, s), 7.03–7.13 (2H, m), 7.17–7.30 (4H, m), 7.32 (1H, s), 7.47 (1H, d), 7.78 (1H, d), 7.78–7.83 (1H, m). MS (MH$^+$). 451.

A mixture of methyl 4-[1-(thiazol-2-yl)-2-(1-methylimidazol-5-yl)ethoxymethyl]-2-(4-fluorophenyl)benzoate (1.45 g, 3.21 mmol) and sodium hydroxide (0.64 g, 16.05 mmol) in methanol (75 ml) and water (7 ml) was stirred under a nitrogen atmosphere at reflux for 18 hours, cooled to ambient temperature and the methanol evaporated off. The residue was treated with aqueous citric acid (1M, 5 ml) and extracted with dichloromethane. The organic extracts were dried and evaporated to dryness to give 2-(4-fluorophenyl)-4-[1-(thiazol-2-yl)-2-(1-methylimidazol-5-yl)ethoxymethyl]benzoic acid as a white foam, (0.877 g, 63%).

$^1$H NMR (CDCl$_3$) δ: 2.94–3.11 (2H, m), 3.43 (3H, s), 4.33 (1H, d), 4.66 (1H, d), 4.84 (1H, dd), 6.72 (1H, s), 6.89–7.13 (5H, m), 7.22–7.32 (3H, m), 7.55 (1H, s), 7.70–7.76 (2H, m). MS (MH$^+$). 438.4.

What is claimed is:
1. A compound of Formula (1):

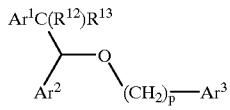

Formula (1)

wherein Ar$^1$ represents:

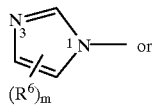

(A)

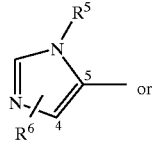

(B)

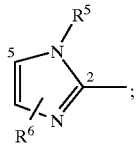

(C)

R$^5$ is hydrogen, C$_{1-4}$alkyl, phenylC$_{1-4}$alkyl;
R$^6$ is hydrogen, C$_{1-4}$alkyl, hydroxyC$_{1-4}$alkyl, haloC$_{1-4}$alkyl, dihaloC$_{1-4}$alkyl, C$_{1-4}$alkoxy, C$_{1-4}$alkoxyC$_{1-4}$alkyl, sulfanylC$_{1-4}$alkyl, aminoC$_{1-4}$alkyl, N-(C$_{1-4}$alkyl)aminoC$_{1-4}$alkyl, N,N-di(C$_{1-4}$alkyl)aminoC$_{1-4}$alkyl or phenylC$_{1-4}$alkyl;
m is 0,1 or 2;
R$^{12}$ and R$^{13}$ are independently hydrogen or C$_{1-4}$ alkyl;
Ar$^2$ is phenyl;
p is 0 or 1;
Ar$^3$ is pyridinyl, the ring being substituted on ring carbon atoms by R$^2$ and —(CH$_2$)$_n$R$^3$ and wherein Ar$^3$ is attached to Ar$^1$C(R$^{12}$)R$^{13}$CH(Ar$^2$)O— by a ring carbon atom;
R$^2$ is a group of the Formula (2):

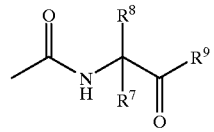

Formula (2)

wherein R$^7$ is hydrogen or C$_{1-4}$alkyl, R$^8$ is —(CH$_2$)$_q$—R$^{10}$ wherein q is 0–4 and R$^{10}$ is C$_{1-4}$alkylsulfanyl, C$_{1-4}$alkylsulfinyl, C$_{1-4}$alkylsulfonyl, hydroxy, C$_{1-4}$alkoxy, carbamoyl, N-C$_{1-4}$alkyl carbamoyl, N,N-(diC$_{1-4}$alkyl)carbamoyl, C$_{1-4}$alkyl, phenyl, thienyl, or C$_{1-4}$alkanoylamino, R$^9$ is hydroxy, C$_{1-6}$alkoxy, C$_{3-9}$cycloalkyloxy, heterocyclyloxy, heterocyclylC$_{1-4}$alkoxy or —NH—SO$_2$-R$^{11}$ wherein R$^{11}$ represents, trifluoromethyl, C$_{1-4}$alkyl, phenyl, heteroaryl, arylC$_{1-4}$alkyl or heteroarylC$_{1-4}$alkyl;

or $R^2$ represents a lactone of Formula (3):

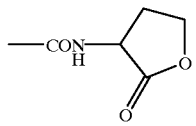
Formula (3)

the group of Formula (2) or (3) having L or D configuration at the chiral alpha carbon in the corresponding free amino acid;

n is 0, 1 or 2;

$R^3$ is phenyl or heteroaryl; phenyl and heteroaryl rings in $R^3$, $R^5$, $R^6$, $R^9$, $R^{11}$ and $Ar^2$ are independently optionally substituted on ring carbon atoms in by up to three substituents selected from $C_{1-4}$alkyl, halogen, hydroxy, $C_{1-4}$alkoxy, $C_{1-4}$alkoxycarbonyl, $C_{1-4}$alkanoyl, $C_{1-4}$alkanoyloxy, amino, $C_{1-4}$alkylamino, di($C_{1-4}$alkyl)amino, $C_{1-4}$alkanoylamino, nitro, cyano, carboxy, thiol, $C_{1-4}$alkylsulfanyl, $C_{1-4}$alkylsulfinyl, $C_{1-4}$alkylsulfonyl, $C_{1-4}$alkanesulphonamido, N-($C_{1-4}$alkylsulphonyl)-N-$C_{1-4}$alkylamino, aminosulfonyl, N-($C_{1-4}$alkyl)aminosulfonyl, N,N-di($C_{1-4}$alkyl)aminosulfonyl, carbamoyl, N-($C_{1-4}$alkyl)carbamoyl, N,N-(di$C_{1-4}$alkyl)carbamoyl, carbamoyl$C_{1-4}$alkyl, N-($C_{1-4}$alkyl)carbamoyl$C_{1-4}$alkyl, N,N-(di$C_{1-4}$alkyl)carbamoyl$C_{1-4}$alkyl, hydroxy$C_{1-4}$alkyl and $C_{1-4}$alkoxy$C_{1-4}$alkyl and on ring NH groups (replacing hydrogen) by $C_{1-4}$alkyl, $C_{1-4}$alkanoyl, $C_{1-4}$alkylsulfonyl, halo$C_{1-4}$alkyl, difluoromethyl or trifluoromethyl;

wherein, in each of $R^3$, $R^9$ and $R^{11}$, each said heterocyclyl group is a 5- or 6-membered monocyclic ring containing 1 to 3 heteroatoms selected from nitrogen, oxygen and sulfur, and each said heteroaryl group is a 5–10 membered monocyclic heteroaryl ring containing up to 3 heteroatoms selected from nitrogen, oxygen and sulphur;

or a pharmaceutically-acceptable salt, prodrug or solvate thereof.

2. A compound according to claim 1 wherein $Ar^1$ is of the formula (A) or (B):

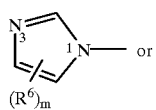
(A)

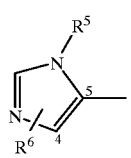
(B)

wherein $R^5$ is hydrogen or methyl; $R^6$ is hydrogen, $C_{1-4}$alkyl, hydroxy$C_{1-4}$alkyl, amino$C_{1-4}$alkyl, fluoro$C_{1-4}$alkyl, difluoro$C_{1-4}$alkyl, $C_{1-4}$alkoxy or $C_{1-4}$alkoxy$C_{1-4}$alkyl and m is as defined in claim 1.

3. A compound according to either claim 1 or claim 2 wherein $Ar^2$ is phenyl optionally substituted on ring carbon atoms by $C_{1-4}$alkyl, halo, nitro, cyano or $C_{1-4}$alkoxy$C_{1-4}$alkyl.

4. A compound according to claim 1 or claim 2 wherein $Ar^3$ is pyridyl, the ring being substituted on ring carbon atoms by $R^2$ and —$(CH_2)_nR^3$ and wherein $Ar^3$ is attached to $Ar^1C(R^{12})R^{13}CH(Ar^2)O$— by a ring carbon atom.

5. A compound according to claim 4 wherein, when n is 0, the pyridyl ring is substituted by $R^2$ in the 4-position and —$(CH_2)_nR^3$ in the 3- or 5-position and when n is 1 or 2, the pyridyl ring is substituted by $R^2$ in the 3- or 5-position and —$(CH_2)_nR^3$ in the 4-position and wherein the positions indicated are relative to the point of attachment of $Ar^3$ to —$(CH_2)_p$—.

6. A compound according to claim 1 or claim 2 wherein $R^2$ is of the formula (2):

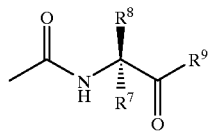

wherein $R^7$ is hydrogen or methyl;

$R^8$ —$(CH_2)_q$—$R^{10}$ wherein q is 1 or 2; $R^{10}$ is $C_{1-4}$alkylsulfanyl, $C_{1-4}$alkylsulfinyl, $C_{1-4}$alkylsulfonyl, hydroxy or $C_{1-4}$alkoxy;

$R^9$ is hydroxy, $C_{1-4}$alkoxy, $C_{3-9}$cycloalkyloxy, heterocyclyloxy or heterocyclyl$C_{1-4}$alkoxy or of the formula —$NHSO_2R^{11}$ wherein $R^{11}$ is phenyl; wherein NH groups in heterocyclic groups in $R^9$ are optionally substituted by methyl, ethyl, acetyl, propionyl, fluoromethyl, difluoromethyl or trifluoromethyl and ring carbon atoms in phenyl or heteroaryl groups in $R^{11}$ are optionally substituted by methyl, halo, $C_{1-4}$alkanoyl, nitro, cyano, $C_{1-4}$alkylsulfinyl, $C_{1-4}$alkylsulfonyl, carbamoyl, $C_{1-4}$alkylcarbamoyl or di$C_{1-4}$alkylcarbamoyl;

or wherein $R^2$ is of the formula (3) as defined in claim 1.

7. A compound according to claim 1 or claim 2 wherein $R^3$ is phenyl, pyridyl or thiazolyl and ring carbon atoms in $R^3$ are optionally substituted by $C_{1-4}$alkyl, halo, $C_{1-4}$alkoxy, nitro, cyano or $C_{1-4}$alkoxy$C_{1-4}$alkyl and a ring NH group in a heteroaryl group in $R^3$ is optionally subtituted by $C_{1-4}$alkyl.

8. A compound according to claim 1 or claim 2 wherein $R^{12}$ and $R^{13}$ are independently hydrogen or methyl.

9. A compound which is:

(2S)-2-{2-(4-fluorophenyl)-6-[1-(4-fluorophenyl)-2-(imidazol-1-yl)ethoxy]pyrid-3-oylamino}-4-methylsulfanylbutyric acid;

tert-butyl (2S)-2-{2-(4-fluorophenyl)-6-[1-(4-fluorophenyl)-2-(1-methylimidazol-5-yl)ethoxymethyl]pyrid-3-oylamino}-4-methylsulfanylbutyrate;

tert-butyl (2S)-2-{3-(4-fluorophenethyl)-6-[1-(4-fluorophenyl)-2-(1-methylimidazol-5-yl)ethoxy]pyrid-2-oylamino}-4-methylsulfanylbutyrate; or cyclopentyl (2S)-2-{3-(4-fluorophenethyl)-6-[1-(4-fluorophenyl)-2-(1-methylimidazol-5-yl)ethoxy]pyrid-2-oylamino}-4-methylsulfanylbutyrate;

or a pharmaceutically-acceptable salt thereof.

10. A process for preparing a compound of the Formula I or a pharmaceutically acceptable salt, prodrug or solvate thereof, which process comprises:

deprotecting a compound of the formula (4):

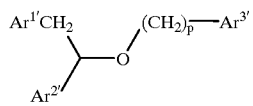

(4)

wherein $Ar^{1'}$ is $Ar^1$ as defined in claim 1 or protected $Ar^1$, $Ar^{2'}$ is $Ar^2$ as defined in claim 1 or protected $Ar^2$ and $Ar^{3'}$ is $Ar^3$ as defined in claim 1 or protected $Ar^3$; wherein at least one protecting group is present; and thereafter if necessary:
  (i) forming a pharmaceutically-acceptable salt,
  (ii) forming a prodrug, and/or
  (iii) forming a solvate.

11. A process for preparing a compound of the Formula I or a pharmaceutically-acceptable salt, prodrug or solvate thereof, which process comprises:
  (i) reacting a compound of the formula (5) with a compound of the formula (6):

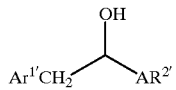

(5)

or (ii) converting one value of $R^9$ in $R^2$ into another value of $R^9$
or (iii) reacting a compound in which $R^2$ in $Ar^{3'}$ is carboxy with a compound of the formula (7):

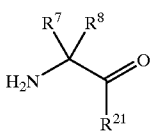

(7)

wherein p, $R^7$ and $R^8$ are as defined in claim 1, $Ar^{1'}$, $Ar^{2'}$, $Ar^{3'}$ $R^7$ and $R^8$ are as defined in claim 15, $R^{21}$ is $R^9$ as defined in claim 1 or a carboxy protecting group and when p is 1, L is a leaving group, and when p is 0, L is hydroxy; and thereafter if necessary:
  (i) removing any protecting groups;
  (ii) forming a pharmaceutically-acceptable salt, prodrug or solvate thereof.

12. A pharmaceutical composition which comprises a compound according to claim 1, 2 or claim 10 and a pharmaceutically-acceptable carrier.

13. A method of treating a disease or medical condition mediated through farnesylation of CAAX-containing proteins which comprises administering to a warm-blooded animal an effective amount of a compound according to claim 1, 2 or 9.

14. The method of claim 13 wherein said disease or medical condition is a carcinoma of the bladder, breast, colon, kidney, liver, lung, ovary, pancreas, stomach, cervix, thyroid or skin.

15. The method of claim 13 wherein said disease or medical condition is a hematopoietic tumor of lymphoid lineage selected from acute lymphocytic leukemia, B-cell lymphoma and Burketts lymphoma.

16. The method of claim 13 wherein said disease or medical condition is a hematopoietic tumor of myeloid lineage selected from acute and chronic myelogenous leukemias and promyelocytic leukemia.

17. The method of claim 13 wherein said disease or medical condition is a tumor of mesenchymal origin selected from fibrosarcoma and rhabdomyosarcoma.

18. The method of claim 13 wherein said disease or medical condition is a tumor selected from melanoma, seminoma, tetratocarcinoma, neuroblastoma and glioma.

* * * * *